(12) United States Patent
Mathew

(10) Patent No.: US 11,339,221 B2
(45) Date of Patent: May 24, 2022

(54) BISPECIFIC ANTIBODY CONSTRUCTS AND METHODS OF USE

(71) Applicant: Tufts Medical Center, Inc., Boston, MA (US)

(72) Inventor: Paul Mathew, Brookline, MA (US)

(73) Assignee: Tufts Medical Center, Inc., Boston, MA (US)

( * ) Notice: Subject to any disclaimer, the term of this patent is extended or adjusted under 35 U.S.C. 154(b) by 0 days.

(21) Appl. No.: 16/759,964

(22) PCT Filed: Oct. 30, 2018

(86) PCT No.: PCT/US2018/058146
§ 371 (c)(1),
(2) Date: Apr. 28, 2020

(87) PCT Pub. No.: WO2019/089544
PCT Pub. Date: May 9, 2019

(65) Prior Publication Data
US 2020/0277382 A1  Sep. 3, 2020

Related U.S. Application Data

(60) Provisional application No. 62/580,079, filed on Nov. 1, 2017.

(51) Int. Cl.

| *A61K 39/395* | (2006.01) |
| *A61K 39/00* | (2006.01) |
| *C07K 16/00* | (2006.01) |
| *C07K 16/46* | (2006.01) |
| *C07K 16/28* | (2006.01) |
| *A61P 35/00* | (2006.01) |
| *C12N 15/63* | (2006.01) |

(52) U.S. Cl.
CPC .......... *C07K 16/2842* (2013.01); *A61P 35/00* (2018.01); *C12N 15/63* (2013.01); *A61K 2039/505* (2013.01); *C07K 2317/24* (2013.01); *C07K 2317/31* (2013.01); *C07K 2317/33* (2013.01); *C07K 2317/52* (2013.01); *C07K 2317/55* (2013.01); *C07K 2317/565* (2013.01); *C07K 2317/567* (2013.01); *C07K 2317/622* (2013.01)

(58) Field of Classification Search
None
See application file for complete search history.

(56) References Cited

U.S. PATENT DOCUMENTS

| 4,399,216 A | 8/1983 | Axel et al. |
| 4,943,529 A | 7/1990 | Van den Berg et al. |
| 4,946,783 A | 8/1990 | Beckwith et al. |
| 5,961,955 A | 10/1999 | Shochat et al. |
| 7,276,589 B2 | 10/2007 | Ramakrishnan et al. |
| 8,039,596 B2 | 10/2011 | Bender et al. |
| 8,562,986 B2* | 10/2013 | Goodman ............... A61P 35/00 424/133.1 |
| 2007/0178552 A1 | 8/2007 | Arathoon et al. |
| 2009/0280118 A1 | 11/2009 | Sheppard et al. |
| 2010/0254977 A1 | 10/2010 | Goodman et al. |
| 2011/0081359 A1 | 4/2011 | Wieder et al. |
| 2011/0287009 A1 | 11/2011 | Scheer et al. |
| 2012/0141573 A1 | 6/2012 | Ling et al. |
| 2016/0053025 A1 | 2/2016 | Oh et al. |
| 2017/0081404 A1* | 3/2017 | Finney ................... C07K 16/28 |

FOREIGN PATENT DOCUMENTS

| EP | 139383 | 5/1985 |
| EP | 183070 | 6/1986 |
| EP | 244234 | 11/1987 |
| EP | 394538 | 10/1990 |
| EP | 402226 | 12/1990 |
| WO | WO 89/05859 | 6/1989 |
| WO | WO 91/00357 | 1/1991 |
| WO | WO 96/027011 | 9/1996 |
| WO | WO 98/050431 | 11/1998 |
| WO | WO 98/052976 | 11/1998 |
| WO | WO 00/34317 | 6/2000 |
| WO | WO 02/69232 | 9/2002 |

OTHER PUBLICATIONS

Eliceiri, Brian, Integrin and Growth Factor Receptor Crosstalk. Circ Res. 2001,89:1104-1110. (Year: 2001).*
Morandi et al. ITGAV and ITGA5 diversely regulate proliferation and adipogenic differentiation of human adipose derived stem cells. Sci Rep Actions. Jul. 1, 2016;6:28889. (Year: 2016).*
Bharadwaj et al. αV-class integrins exert dual roles on α5β1 integrins to strengthen adhesion to fibronectin. Nat Commun. Jan. 27, 2017;8:14348 (Year: 2017).*
Andrew Lai .Towards the Development of Novel Bispecific Antibodies to Inhibit Key Cell Surface Receptors Integral for the Growth and Migration of Dissertation, Queensland University of Technology, pp. 1-283, 2016. (Year: 2016).*
H.T.A. Ahmedah. Correlation between the expression of integrins and their role in cancer progression. Expression pattern of integrins αvβ3, αvβ5 and α5β1 in clinical and experimental tumour samples. (University of Bradford eThesis, PhD Thesis, pp. 1-284, 2015). (Year: 2015).*
Kimura et al. Engineered cystine knot peptides that bind αvβ3, αvβ5, and α5β1 integrins with low-nanomolar affinity. Proteins 2009; 77:359-369. (Year: 2009).*
Joshi et al. A Bispecific Antibody Targeting the αv and α5β1 Integrins Induces Integrin Degradation in Prostate Cancer Cells and is Superior to Monospecific Antibodies. Mol Cancer Res. Jan. 2020;18(1):27-32 (Year: 2020).*

(Continued)

*Primary Examiner* — Maher M Haddad
(74) *Attorney, Agent, or Firm* — Fish & Richardson P.C.

(57) ABSTRACT

The present invention relates to bispecific antibody constructs that specifically bind both integrin alpha-V and integrin α5 (e.g., α5β1) and methods of making and using those constructs to treat cancer or other pathological conditions involving these integrins.

12 Claims, 26 Drawing Sheets
Specification includes a Sequence Listing.

(56) References Cited

OTHER PUBLICATIONS

Connell et al. Aberrant integrin αv and α5 expression in prostate adenocarcinomas and bone-metastases is consistent with a bone-colonizing phenotype. Transl Androl Urol. Aug. 2020;9(4):1630-1638. (Year: 2020).*

Laurens, N., et al., "Single and combined effects of alpha(v)beta(3)- and alpha5beta1-integrins on capillary tube formation in a human fibrinous matrix," Angiogenesis (May 6, 2009) vol. 12, No. 3, pp. 275-285. (Year: 2009).*

Asano et al., "Increased expression of integrin αvβ3 contributes to the establishment of autocrine TGF-β signaling in scleroderma fibroblasts," The Journal of Immunology, Dec. 1, 2005, 175(11):7708-18.

Avraamides et al., "Integrins in angiogenesis and lymphangiogenesis," Nature Reviews Cancer, Aug. 2008, 8(8):604-17.

Ballance et al., "Transformation of Aspergillus nidulans by the orotidine-5'-phosphate decarboxylase gene of Neurospora crassa," Biochemical and Biophysical Research Communications. Apr. 15, 1983, 112(1):284-9.

Brinkmann et al., "The making of bispecific antibodies," Mabs, Feb. 17, 2017, 9(2):182-212.

Case et al., "Efficient transformation of Neurospora crassa by utilizing hybrid plasmid DNA," Proceedings of the National Academy of Sciences, USA, Oct. 1, 1979. 76(10):5259-63.

Chothia et al., "Canonical structures for the hypervariable regions of immunoglobulins," Journal of Molecular Biology, Aug. 20, 1987, 196(4):901-17.

Connell et al., "Aberrant integrin αv and α5 expression patterns in prostate adenocarcinomas and bone-metastases from prostate cancer are consistent with a bone-colonizing phenotype," Cancer Research, Jul. 2019, 79(13 Supplement):Abstiact 114, 2 pages, doi:10.1158/1538-7445.AM2019.

David et al., "Protein iodination with solid state lactoperoxidase," Biochemistry, Feb. 1, 1974, 13(5):1014-21.

Elez et al., "Abituzumab combined with cetuximab plus irinotecan versus cetuximab plus irinotecan alone for patients with KRAS wild-type metastatic colorectal cancer: the randomised phase I/II, Poseidon trial," Annals of Oncology, Jan. 1, 2015, 26(1):132-40.

Fan et al., "Bispecific antibodies and their applications," Journal of Hematology & Oncology, Dec. 1, 2015, 8(1):130, 14 pages.

Flatman et al., "Process analytics for purification of monoclonal antibodies," Journal of Chromatography B, Mar. 15, 2007, 848(1):79-87.

Fleer et al., "Stable multicopy vectors for high-level secretion of recombinant human serum albumin by Kluyveromyces Yeasts," Bio/Technology, Oct. 1991, 9(10):968-75.

Graham et al., "A new technique for the assay of infectivity of human adenovirus 5 DNA," Virology, Apr. 1, 1973, 52(2):456-67.

Graham et al., "Characteristics of a human cell line transformed by DNA from human adenovirus type 5," Journal of General Virology, Jul. 1, 1977, 36(1):59-72.

Han et al., "Efficient generation of bispecific IgG antibodies by split intein mediated protein trans-splicing system," Scientific Reports. Aug. 21, 2017, 7(1):1-1.

Henderson et al., "Targeting of α v integrin identifies a core molecular pathway that regulates fibrosis in several organs," Nature Medicine, Dec. 2013. 19(12):1617-24 plus 3 pages of online supplemental information, doi.org/10.1038/nm.3282.

Hinz, "It has to be the αv: myofibroblast integrins activate latent TGF-β1," Nature Medicine. Dec. 2013, 19(12):1567-8.

Hsiao et al., "High-frequency transformation of yeast by plasmids containing the cloned yeast ARG4 gene," Proceedings of the National Academy of Sciences, USA, Aug. 1, 1979, 76(8):3829-33.

Hunter et al., "Preparation of iodine-131 labelled human growth hormone of high specific activity," Nature, May 5, 1962, 194(4827):495-6.

Joshi et al., "A bispecific antibody targeting the αv and α5β1 integrins induces integrin degradation in prostate cancer cells and is superior to monospecific antibodies," Molecular Cancer Research, Jan. 1, 2020, 18:27-32, and Supplementary Materials and Methods, 8 pages (published online Oct. 21, 2019; doi: 10.1158/1541-7786.MCR-19-0442).

Joslti et al., Superior targeting of tumor-stromal interactions and endothelial migration with a bispecific antibody to α5 and αv integrins, Cancer Research, Jul. 2018, 78(13 Supplement) Abstract 182, 2 pages, doi: 10.1158/1538-7445.AM2018-182.

Joshi et al., "The comparative superiority of bispecific antibody targeting of αv and α5 integrins is uniquely characterized by induced degradation of integrins," Cancer Research, Jul. 2019;79(13 Supplement):Abstract No. 1902, 2 pages, doi:10.1158/1538-7445.AM2019-1902.

Kelly et al., "Transformation of Aspergillus niger by the amdS gene of Aspergillus nidulans," The EMBO Journal, Feb. 1, 1985, 4(2):475-9.

Keown et al., "Methods for introducing DNA into mammalian cells," Methods in Enzymology, Jan. 1, 1990, 185:527-37.

Khan et al., "The role of integrins in TGFβ activation in the tumour stroma," Cell and Tissue Research, Sep. 1, 2016, 365(3):657-73.

Kontermann et al., "Recombinant bispecific antibodies for cancer therapy," Acta Pharmacologica Sinica, Jan. 2005, 26(1):1-9.

Kontermann et al., "Bispecific antibodies," Drug Discovery Today, Jul. 1, 2015, 20(7):838-47.

Liu et al., "Fc engineering for developing therapeutic bispecific antibodies and novel scaffolds," Frontiers in Immunology, Jan. 26, 2017, 8:38.

De Louvencourt et al., "Transformation of Kluyveromyces lactis by killer plasmid DNA," Journal of Bacteriology, May 1, 1983, 154(2):737-42.

MacCallum et al., "Antibody-antigen interactions: contact analysis and binding site topography," Journal of Molecular Biology, Oct. 11, 1996. 262(5):732-45.

Mansour et al., "Disruption of the proto-oncogene int-2 in mouse embryo-derived stem cells: a general strategy for targeting mutations to non-selectable genes," Nature, Nov. 24, 1988, 336(6197):348-52.

Mather, "Establishment and characterization of two distinct mouse testicular epithelial cell line," Biology of Reproduction, Aug. 1, 1980, 23(1):243-52.

Nygren et al., "Conjugation of horseradish peroxidase to Fab fragments with different homobifunctional and heterobifunctional cross-linking reagents," Journal of Histochemistry and Cytochemistiy, May 1982 30:407-12.

Pain et al., "Preparation of protein A-peroxidase monoconjugate using a heterobifunctional reagent, and its use in enzyme immunoassays," Journal of Immunological Methods, Jan. 30, 1981, 40(2):219-30.

PCT International Search Report and Written Opinion in International Appln. No. PCT/US2018/058146, dated Mar. 14, 2019, 11 pages.

Raab-Westphal et al., "Integrins as therapeutic targets: successes and cancers," Cancers, Sep. 2017, 9(9), doi.org/10.3390/cancers9090110 (28 pages).

Ray, "Key role for α v integrins in myofibroblasts in liver fibrosis," Nature Reviews Gastroenterology & Hepatology, Jan. 2014, 11(1):4.

Schaffner et al., "Integrin α5β1, the fibronectin receptor, as a pertinent therapeutic target in solid tumors," Cancers, Mar. 2013, 5(1):27-47.

Beach et al., "High-frequency transformation of the fission yeast Schizosaccharomyces pombe," Nature, Mar. 1981,290(5802):140-2.

Shaw et al., "A general method for the transfer of cloned genes to plant cells," Gene, Sep. 1, 1983, 23(3):315-30.

Spiess et al., "Alternative molecular formats and therapeutic applications for bispecific antibodies," Molecular Immunology, Oct. 1, 2015, 67(2):95-106.

Sreekrishna et al., "High level expression of heterologous proteins in methylotrophic yeast Pichia pastoris," Journal of Basic Microbiology, 1988, 28(4):265-78.

Sutherland et al., "RGD-binding integrins in prostate cancer: expression patterns and therapeutic prospects against bone metastasis," Cancers, Dec. 4, 2012, 4(4):1106-45.

(56) References Cited

OTHER PUBLICATIONS

Tilburn et al., "Transformation by integration in Aspergillus nidulans," Gene, Dec. 1, 1983, 26(2-3):205-21.

Urlaub et al., "Isolation of Chinese hamster cell mutants deficient in dihydrofolate reductase activity," Proceedings of the National Academy of Sciences, USA. July 1, 1980, 77(7):4216-20.

Van Solingen et al., "Fusion of yeast spheroplaste," Journal of Bacteriology, May 1, 1977, 130(2):946-7.

Van den Berg et al., "Kluyveromyces as a host for heterologous gene expression: expression and secretion of prochymosin," Bio/Technology, Feb. 1990, 8(2):135-9.

Weis et al., "αV integrins in angiogenesis and cancer," Cold Spring Harbor Perspectives in Medicine, Sep. 1, 2011, 1(1):a006478.

Wilson et al., "Human tumour immune evasion via TGF-β blocks NK cell activation but not survival allowing therapeutic restoration of anti-tumour activity," PloS One, Sep. 6, 2011;6(9), 10 pages.

Yelton et al., "Transformation of Aspergillus nidulans by using a trpC plasmid," Proceedings of the National Academy of Sciences, USA, Mar. 1, 1984, 81(5):1470-4.

Zhu et al., "Remodeling domain interfaces to enhance heterodimer formation," Protein Science, Apr. 6, 1997, 6(4):781-8.

Zheng et al., "Cross-arm binding efficiency of anEGFR x c-Met bispecific antibody," Mabs, Apr. 2, 2016, 8(3):551-61.

Cmdden et al., "Targeting the IGF-1R: the tale of the tortoise and the hare," Frontiers in Endocrinology, Apr. 27, 2015, 6(64):1-6.

Van der Flier et al. "Endothelial α5 and αv integrins cooperate in remodeling of the vasculature during development," Development, Jul. 15, 2010, 137(14):2439-2449.

\* cited by examiner

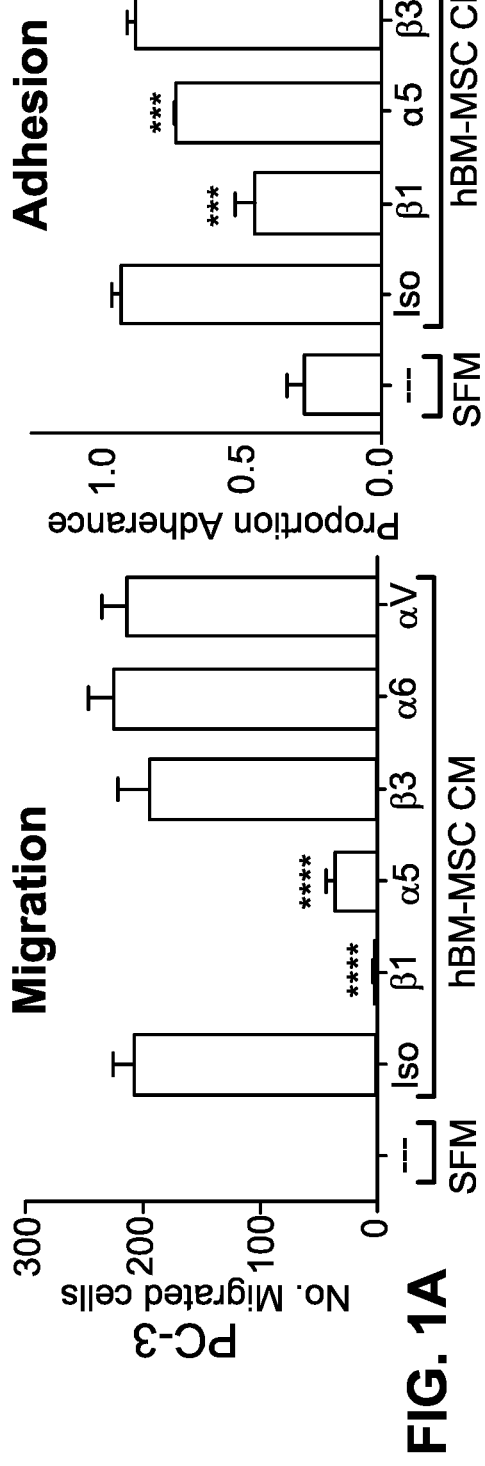
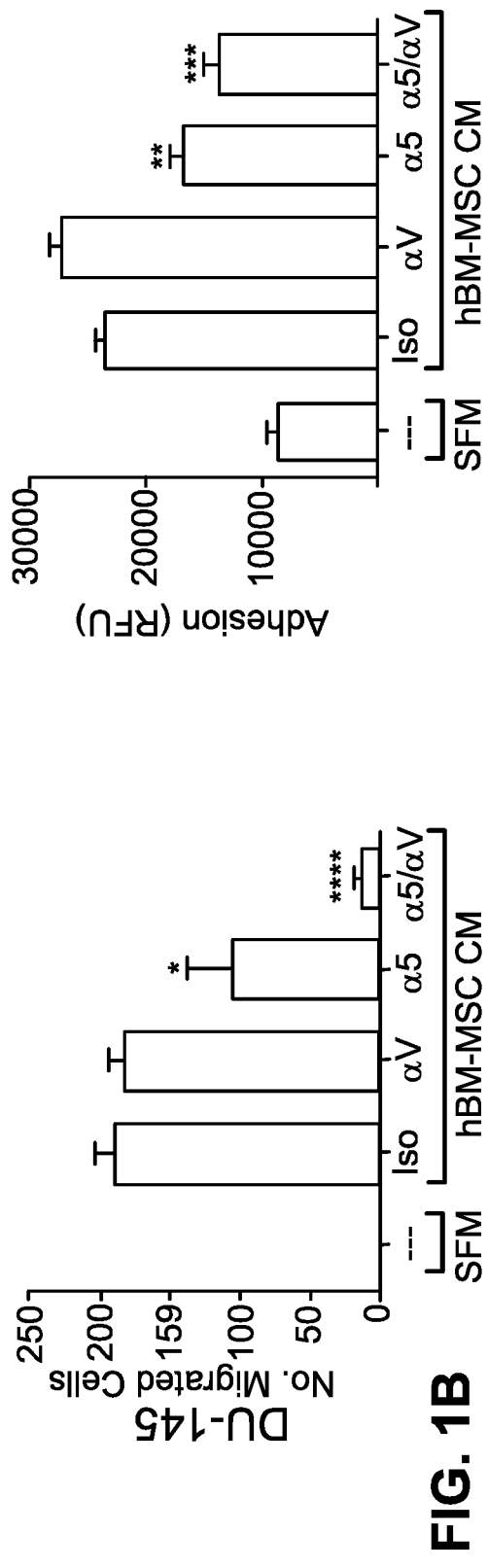
FIG. 1A
FIG. 1B

Reduced SDS-Page
Lane 1: Marker
Lane 2: Recombinant Anti-ITGAV x Anti-ITGA5 IgG-scFv

| Line | α5 | αv | Bispecific α5xαv | MFI α5 | MFI αv | MFI bispecific α5xαv |
|---|---|---|---|---|---|---|
| PC3 | + | + | + | 16.9098 | 36.06465 | 75.75537 |
| C42B | + | + | + | 18.37594 | 30.11774 | 92.1379 |
| DU-145 | + | + | + | 19.82366 | 43.15125 | 9.707535 |
| VCAP | - | + | + | 3.802579 | 5.070503 | 9.707535 |
| RWPE-1 | + | + | + | 19.49864 | 31.3873 | 80.38211 |

MFI: mean fluorescent intensity          Correlation coefficient: .9187

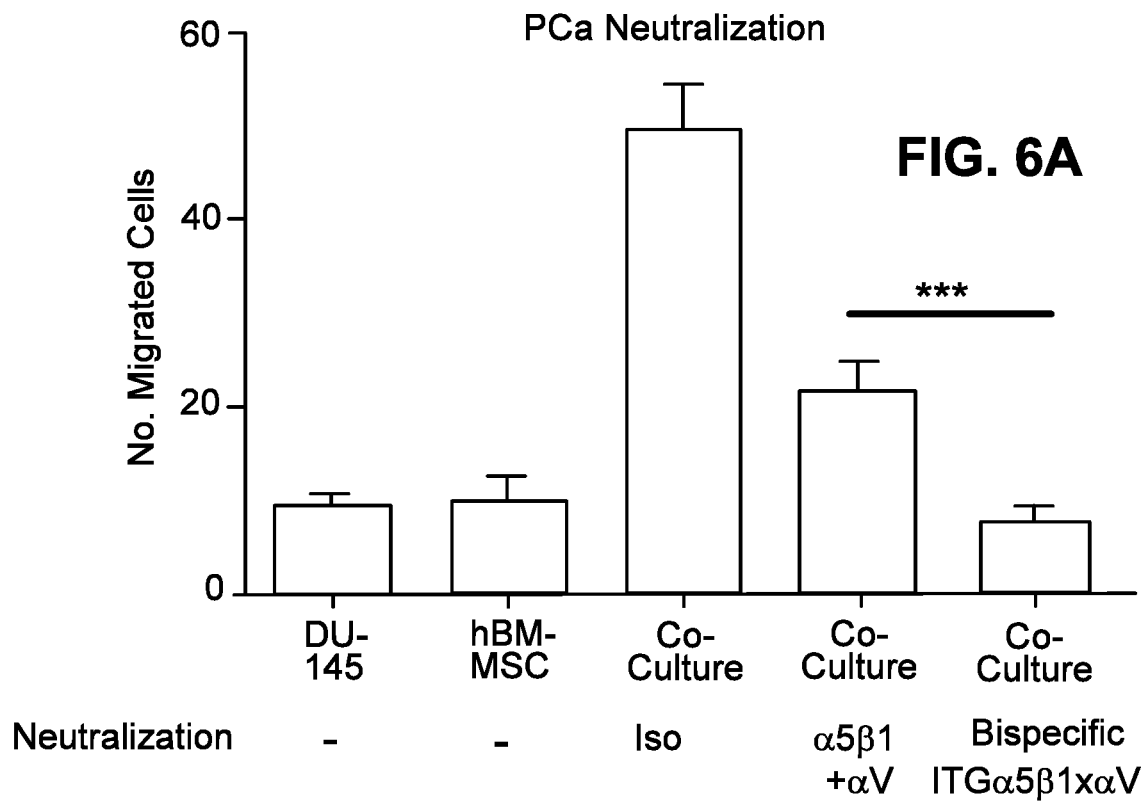
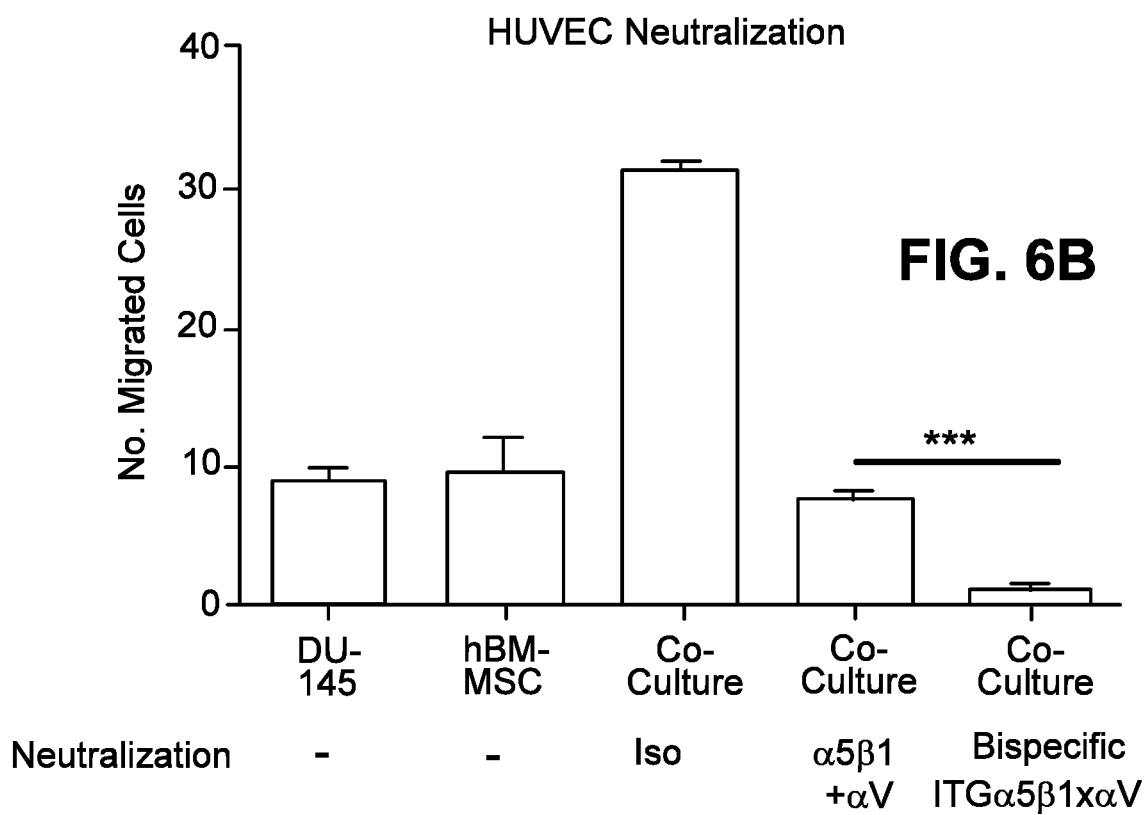

```
  5  MELGLSWIFLLAILKGVQC]QVQLQQSGGELAKPGASVKVSCKASGYTFSISFWMH]WVRQAPGQGLEWIG]YINPRSGYTEY
                       P1VHFR1-2                            P1VHCDR1      P1VHFR2           P1VHCDR2
     NEFRK]KATMTDTSTSTAYMELSSLRSEDTAVYYCAS]ELGRGAMDY]WGQGTTVTVSS]ASTKGPSVFPLAPCSRSTSEST
                 P1VHFR3                    P1VHCDR3            P1VHFR4
 10  AALGCLVKDYFPEPVTVSWNSGALTSGVHTFPPAVLQSSGLYSLSSVVTVPSSNFGTQTYTCNVDHKPSNTKVDKTVER
     KCCVECPPCPAPPVAGPSVFLFPPKPKDTLMISRTPEVTCVVVDVSHEDPEVQFNWYVNGVEVHNAKTKPREEQFNSTF
 15  RVVSVLTVVHQDWLNGKEYKCKVSNKGLPAPIEKTISKTKGQPREPQVYTLPPSREEMTKNQVSLTCLVKGFYPSDIAV
     EWESNGQPENNYKTTPPMLDSDGSFFLYSKLTVDKSRWQQGNVFSCSVMHEALHNHYTQKSLSLSPGKGGGGSGGGGS
 20  [QVQLKESGPGLVAPSQSLSITCTVSGFSLTDYGVHI]WVRQPPGKGLEWLV]IWSDGSSTYNSALKS]RMTIRKDNSKSQVFL
                  P2VHFR1                    P2VHCDR1             P2VHCDR2              P2VHFR3
     [MNSLQTDDSAMYYCAR]HGTYYGMTTGDALDY]WGQGTSVTVSS]GGGGSGGGGSGGGGS]QIVLTQSPAIMSASLGER
                      P2VHCDR3              P2VHFR4              LINKER              P2VLFR1
 25  VTMTC]TASSSVSSSNYLH]WYQQKPGSAPNLWIY]STSNLAS]GVPARFSGSGSGTSYSLTISSMEAEDAATYYC]HQYLRSPPT
                P2VLCDR1            P2VLFR2         P2VLCDR2                  P2VLFR3          P2VLCDR3
     ]FGQGTKLEIK]    (SEQ ID NO:47)
        P2VLFR4
```

FIG. 12A

MRVPAQLLGLLLWLPGTRC[DIQMTQSPSSLSASVGDRVTITC]RASQDISNYLA[WYQQKPGKAPKLLIY]TSKIHS
　　　　P1VLFR1　　　　　　　　P1VLCDR1　　　　　P1VLFR2　　　　P1VLCDR2

[GVPSRFSGSGSGTDYTFTISSLQPEDIATYYC]QQGNTFPYT[FGQGTKVEIK]RTVAAPSVFIFPPSDEQLKSGTASVVCL
　　　　　P1VLFR3　　　　　　　　P1VLCDR3　　　P1VLFR4　　　　　Constant Region (Fc)

LNNFYPREAKVQWKVDNALQSGNSQESVTEQDSKDSTYSLSSTLTLSKADYEKHKVYACEVTHQGLSSPVTKSFNRGEC (SEQ ID NO:48)

FIG. 12B

| Abbreviation | Sequence | Variants |
|---|---|---|
| Sequences in the light chain binding alpha-V | | |
| P1VLFR1 | DIQMTQSPSSLSASVGDRVTITC (SEQ ID NO:13) | |
| P1VLCDR1 | RASQDISNYLA (SEQ ID NO:1) | |
| P1VLFR2 | WYQQKPGKAPKLLIY (SEQ ID NO:14) | |
| P1VLCDR2 | YTSKIHS (SEQ ID NO:2) | |
| P1VLFR3 | GVPSRFSGSGSGTDYTFTISSLQPEDIATYYC (SEQ ID NO:15) | |
| P1VLCDR3 | QQGNTFPYT (SEQ ID NO:3) | |
| P1VLFR4 | FGQGTKVEIK (SEQ ID NO:16) | |
| Sequences in the heavy chain binding alpha-V | | |
| P1VHFR1-2 | QVQLQQSGGELAKPGASVKVSCKASGYTFS (SEQ ID NO:118) | |
| P1VHCDR1 | SFWMH (SEQ ID NO:4) | |
| P1VHFR2 | WVRQAPGQGLEWIG (SEQ ID NO:18) | |
| P1VHCDR2 | YINPRSGYTEYNEIFRD (SEQ ID NO:5) | YINPRSGYTECNEIFRD (SEQ ID NO:91) |
| P1VHFR3 | KATMTTDTSTSTAYMELSSLRSEDTAVYYCAS (SEQ ID NO:19) | |
| P1VHCDR3 | FLGRGAMDY (SEQ ID NO:6) | |
| P1VHFR4 | WGQGTTVTVSS (SEQ ID NO:20) | |
| | | |
| Sequences in the light chain binding α5β1 | | |
| P2VLFR1 | QIVLTQSPAIMSASLGERVTMTC (SEQ ID NO:21) | Substitutions of one or more of: Q1, V3, A9, I10, M11, L15, E17, M21, for example,<br>DIQLTQSPSSMSASLGDRVTMTC (SEQ ID NO:92)<br>DIQLTQSPSSLSASVGDRVTMTC (SEQ ID NO:93)<br>DIQMTQSPSSLSASVGDRVTITC (SEQ ID NO:94)<br>DIQLTQSPSSLSASVGDRVTITC (SEQ ID NO:95)<br>DIQLTQSPSSLSASVGDRVTMTC (SEQ ID NO:96) |
| P2VLCDR1 | TASSSVSSNYLH (SEQ ID NO:7) | |
| P2VLFR2 | WYQQKPGSAPNLWIY (SEQ ID NO:22) | Substitutions of one or more of: S8, N11, and W13, for example,<br>WYQQKPGKAPNLWIY (SEQ ID NO:97)<br>WYQQKPGKAPKLWIY (SEQ ID NO:98)<br>WYQQKPGKAPKLLIY (SEQ ID NO:99) |
| P2VLCDR2 | STSNLAS (SEQ ID NO:8) | |
| P2VLFR3 | GVPARFSGSGSGTSYSLTISSMEAEDAATYYC (SEQ ID NO:23) | Substitutions of one or more of: A4, S14, Y15, S16, M22, E23, A24, A27, for example,<br>GVPSRFSGSGSGTDYTLTISSMQPEDFATYYC (SEQ ID NO:100)<br>GVPSRFSGSGSGTDFTLTISSLQPEDFATYYC (SEQ ID NO:101) |
| P2VLCDR3 | HQYLRSPPT (SEQ ID NO:9) | |
| P2VLFR4 | FGGGTKLEIK (SEQ ID NO:24) | Substitutions of one or more of: G3 and L7, for example<br>FGQGTKLEIK (SEQ ID NO:102)<br>FGQGTKVEIK (SEQ ID NO:103) |
| Sequences in the heavy chain binding α5β1 | | |
| P2VHFR1 | QVQLKESGPGLVAPSQSLSITCTIS (SEQ ID NO:25) | Substitutions of one or more of: Q1, K5, P9, A13, S15, Q16, S19, I20, T21, T23, I24, for example,<br>QVQLVESGPGLVQPGGSLRISKAIS (SEQ ID NO:104) |

FIG. 12C-1

| | | |
|---|---|---|
| P2VHCDR1 | GFSLTDYGVH (SEQ ID NO:10) | EVQLVESGGGLVQPGGSLRISCAIS (SEQ ID NO:105)<br>EVQLVESGGGLVQPGGSLRLSCAAS (SEQ ID NO:106)<br>EVQLVESGGGLVQPGGSLRLSCAIS (SEQ ID NO:107)<br>QVQLVESGGGLVQPGGSLRISCAIS (SEQ ID NO:108) |
| P2VHFR2 | WVRQPPGKGLEWLV (SEQ ID NO:26) | Substitutions of one or more of: P5, L13 or V14m for example,<br>WVRQAPGKGLEWLV (SEQ ID NO:109)<br>WVRQAPGKGLEWVS (SEQ ID NO:110) |
| P2VHCDR2 | VIWSDGSSTYNSALKS (SEQ ID NO:11) | |
| P2VHFR3 | RMTIRKDNSKSQVFLIMNSLQTDDSAMYYCAR (SEQ ID NO:27) | Substitutions of one or more of: M2, R5, K6, S11, Q12, V13, F14, I16, Q21, T22, D23, S25, or M27, for example,<br>RMTISKDNSKSTVYLQMNSLRAEDTAMYYCAR (SEQ ID NO:111)<br>RMTISKDNSKNTVYLQMNSLRAEDTAVYYCAR (SEQ ID NO:112)<br>RFTISRDNSKNTLYLQMNSLRAEDTAVYYCAR (SEQ ID NO:113)<br>RMTISKDNSKSTVYLQMNSLRAEDTAVYYCAR (SEQ ID NO:114) |
| P2VHCDR3 | HGTYYGMTTTGDALDY (SEQ ID NO:12) | |
| P2VHFR4 | WGQGTSVTVSS (SEQ ID NO:28) | Substitutions of S6, for example, WGQGTLVTVSS (SEQ ID NO:115) |
| | Modified Hinge<br>*ERKCCVECPPCP → EPKSSDKTHTCPPCP*<br>(SEQ ID NO:116) | (SEQ ID NO:117) |

HUVEC

HUVEC

>HC
  HindIII                                           Gene Sequences

5'-`GAATTC`GCCACCATGGAGCTGGGCCTGTCCTGGATCTTCCTGCTGGCCATCCTGAAGGG
CGTGCAGTGCCAGGTTCAGCTGCAGCAGTCTGGAGGAGAGCTGGCTAAGCCTGGAGCTTC
TGTGAAGGTGAGCTGTAAGGCTTCCGGCTACACCTTTAGCTCCTTCTGGATGCACTGGGTG
CGGCAGGCTCCTGGACAGGGACTGGAGTGGATTGGATATATCAATCCCCGGTCCGGCTACA
CCGAGTATAATGAGATCTTTCGGGATAAGGCCACCATGACCACCGACACATCCACCTCTACC
GCTTACATGGAGCTGAGCAGCCTGAGGTCCGAGGATACAGCTGTGTATTACTGTGCTTCCTT
TCTGGGCCGGGGCGCTATGGACTATTGGGGACAGGGAACCACCGTGACCGTGTCCTCCACC
AAAGGTCCTTCCGTGTTTCCCCTGGCCCCTTGCTCCAGGTCCACCTCCGAGTCCACCGCTG
CTCTGGGATGCCTGGTGAAAGATTACTTCCCCGAGCCCGTGACCGTGTCTTGGAATAGTGG
CGCTCTGACCAGCGGCGTTCACACCTTCCCTGCTGTTCTGCAGAGCTCCGGACTGTATAGC
CTGTCCAGCGTGGTGACCGTGCCTTCCTCCAATTTTGGCACCCAGACCTACACCTGTAATGT
GGATCACAAGCCCAGCAACACCAAGGTGGACAAGACCGTGGAGCGGAAGTGTTGTGTGG
AGTGTCCCCCATGTCCCGCTCCTCCTGTGGCTGGACCTTCCGTGTTTCTGTTCCCCCCAAAG
CCCAAGGATACCCTGATGATCAGCAGGACCCCTGAGGTGACCTGTGTGGTTGTGGACGTGT
CCCACGAGGACCCTGAAGTTCAGTTCAATTGGTACGTGGATGGCGTGGAGGTGCACAACG
CTAAGACCAAGCCTCGGGAGGAGCAGTTCAACAGCACCTTTAGGGTGGTGTCCGTGTTGA
CCGTGGTGCATCAGGATTGGCTGAACGGCAAGGAGTACAAGTGCAAGGTGTCCAACAAGG
GCCTGCCCGCTCCTATTGAGAAGACCATCAGCAAGACCAAGGGCCAGCCCAGAGAGCCTC
AGGTGTATACACTGCCCCCCTCTAGGGAGGAGATGACAAAGAACCAGGTGAGCCTGACCT
GTCTGGTGAAGGGATTCTATCCCTCCGATATCGCCGTGGAGTGGGAGTCCAATGGCCAGCCT
GAAAACAACTATAAGACCACCCCTCCTATGCTGGATAGCGATGGCTCCTTTTTCCTGTACAG
CAAGCTGACCGTGGATAAGAGCCGGTGGCAGCAGGGAAATGTGTTTTCCTGTTCCGTGATG
CACGAGGCTCTGCACAACCACTACACCCAGAAGAGCCTGAGCCTGAGCCCTGGAAAGGGA
GGAGGAGGAGGCGGAGGAAGCCAGGTGCAGCTGAAGGAGTCTGGACCAGGACTGGTGGC
TCCATCTCAGTCTCTGTCCATCACCTGCACCATCTCCGGCTTTTCCCTGACCGACTATGGCGT
GCACTGGGTTAGGCAGCCTCCTGGAAAGGGACTGGAGTGGTTGGTGGTCATTTGGAGCGAT
GGCAGCTCCACCTATAACTCCGCTCTGAAGAGCCGGATGACCATCAGGAAGGACAACAGC
AAGAGCCAGGTGTTCCTGATCATGAATAGCCTGCAGACCGATGACAGCGCCATGTACTACT
GTGCTAGGCACGGCACCTATTATGGCATGACCACCACCGGCGACGCTTTGGACTACTGGGG
ACAGGGAACCAGCGTGACAGTGTCTAGCGGAGGAGGAGGATCTGGCGGAGGAGGAAGCG
GAGGAGGAGGATCTCAGATCGTGCTGACCCAGAGCCCTGCTATCATGTCCGCTTCTCTGGG
CGAGAGAGTGACCATGACCTGCACAGCTTCCAGCTCCGTGAGCTCTAATTACCTGCACTGG
TATCAGCAGAAGCCTGGCAGCGCTCCAAACTTGTGGATCTATAGCACCAGCAATCTGGCCA
GCGGCGTGCCTGCTAGGTTTTCCGGATCTGGATCTGGCACCAGCTACTCCCTGACCATCAGC
TCTATGGAGGCCGAGGATGCTGCCACATACTATTGTCACCAGTATCTGAGGAGCCCCCCTAC
CTTTGGCGGAGGAACCAAACTGGAGATCAAGTGA`GCGGCCGC`-3' (SEQ ID NO:61)
>LC                                          NotI
  HindIII
5'-`GAATTC`GCCACCATGCGGGTGCCCGCCCAGCTGCTGGGCCTGCTGCTGCTGTGGCTGCC
CGGCACCCGGTGCGACATCCAGATGACCCAGAGCCCTTCCTCCCTGTCTGCTTCTGTGGGA
GATCGGGTGACCATCACCTGCAGAGCTTCCCAGGATATCTCCAATTACCTGGCTTGGTATCA
ACAGAAGCCCGGCAAGGCTCCTAAGCTGTTGATCTACTATACCAGCAAGATCCACAGCGGC
GTGCCCTCCAGGTTTTCTGGATCTGGATCTGGCACCGATTACACCTTTACCATCTCCAGCCT
GCAGCCCGAGGACATTGCTACATACTACTGCCAGCAGGGCAACACCTTTCCCTACACCTTC
GGCCAGGGCACAAAGGTTGAGATCAAGGTGGCTGCTCCTTCCGTGTTTATCTTCCCCCCTA
GCGATGAGCAGCTGAAGTCCGGAACCGCTTCCGTTGTGTGTCTGCTGAACAACTTCTATCC
CCGGGAGGCCAAGGTGCAGTGGAAAGTGGATAACGCCCTGCAGTCCGGCAACTCTCAGGA
ATCTGTGACCGAGCAGGACTCCAAGGACTCCACATACAGCCTGAGCTCCACCCTGACCCTG
TCTAAGGCTGACTACGAGAAGCACAAGGTGTACGCTTGCGAGGTGACCCACCAGGGATTG
TCTAGCCCTGTGACCAAGTCCTTCAATCGGGGCGAGTGCTGAATAA`GCGGCCGC`-3' (SEQ ID NO:62)

FIG. 20A                                NotI

Amino Acid Sequences

>HC

QVQLQQSGGELAKPGASVKVSCKASGYTFSSFWMHWVRQAPGQGLEWIGYINPRSGYTEYNEIFR
DKATMTTDTSTSTAYMELSSLRSEDTAVYYCASFLGRGAMDYWGQGTTVTVSSASTKGPSVFPLA
PCSRSTSESTAALGCLVKDYFPEPVTVSWNSGALTSGVHTFPAVLQSSGLYSLSSVVTVPSSNFG
TQTYTCNVDHKPSNTKVDKTVERKCCVECPPCPAPPVAGPSVFLFPPKPKDTLMISRTPEVTCVV
VDVSHEDPEVQFNWYVDGVEVHNAKTKPREEQFNSTFRVVSVLTVVHQDWLNGKEYKCKVSNKGL
PAPIEKTISKTKGQPREPQVYTLPPSREEMTKNQVSLTCLVKGFYPSDIAVEWESNGQPENNYKT
TPPMLDSDGSFFLYSKLTVDKSRWQQGNVFSCSVMHEALHNHYTQKSLSLSPGKGGGGSGGGGSQ
VQLKESGPGLVAPSQSLSITCTISGFSLTDYGVHWVRQPPGKGLEWLVVIWSDGSSTYNSALKSR
MTIRKDNSKSQVFLIMNSLQTDDSAMYYCARHGTYYGMTTTGDALDYWGQGTSVTVSSGGGGSGG
GGSGGGGSQIVLTQSPAIMSASLGERVTMTCTASSSVSSNYLHWYQQKPGSAPNLWIYSTSNLAS
GVPARFSGSGSGTSYSLTISSMEAEDAATYYCHQYLRSPPTFGGGTKLEIK (SEQ ID NO:63)

>LC

DIQMTQSPSSLSASVGDRVTITCRASQDISNYLAWYQQKPGKAPKLLIYYTSKIHSGVPSRFSGS
GSGTDYTFTISSLQPEDIATYYCQQGNTFPYTFGQGTKVEIKRTVAAPSVFIFPPSDEQLKSGTA
SVVCLLNNFYPREAKVQWKVDNALQSGNSQESVTEQDSKDSTYSLSSTLTLSKADYEKHKVYACE
VTHQGLSSPVTKSFNRGEC (SEQ ID NO:64)

FIG. 20B

BISPECIFIC ANTIBODY CONSTRUCTS AND METHODS OF USE

CROSS-REFERENCE TO RELATED APPLICATIONS

This application is a 371 U.S. National Phase Application of PCT/US2018/058146, filed on Oct. 30, 2018, which claims the benefit of priority of U.S. Provisional Appl. No. 62/580,079, filed Nov. 1, 2017, the contents of which are incorporated by reference in their entirety herein.

SEQUENCE LISTING

This application contains a Sequence Listing that has been submitted electronically as an ASCII text file named "Sequence_Listing.txt." The ASCII text file, created on Dec. 14, 2021, is 81 KB in size. The material in the ASCII text file is hereby incorporated by reference in its entirety.

FIELD OF THE INVENTION

The present invention relates to bispecific antibody constructs that specifically bind integrin alpha-V and integrin α5 and methods of making and using those constructs to treat cancer (e.g., prostate cancer) or other conditions associated with expression and activity of those integrins.

Integrin alpha-V and integrin α5 function in diverse tumor cell types to promote a range of behaviors essential to the survival, progression and metastatic behaviors of cancer cells. These include stem-progenitor function, anchorage to the surrounding matrix, facilitation of fibrin-invasion in metastatic niches, transduction of survival signals, activation of membrane proteases including matrix-metalloproteases, response to specific environmental cues to home to distant organs, bone metastases, the induction of fibroblast-myofibroblast transitions, epithelial-mesenchymal transition, angiogenesis, and immune evasion via metalloprotease and TGF-beta signaling activation. Weis et al., Cold Spring Harbor Perspectives in Medicine 2011; 1; a006478; Schaffner et al., Cancers 2013; 1:27-47; Raab-Westphal et al., Cancers (Basel) 2017; 9:110; Sutherland et al., Cancers (Basel) 2012; 4:1106-45; Khan et al., Cell and Tissue Research 2016; 365:65673; Hinz, Nature Medicine 2013; 19:1567; Wilson et al., PLoS One 2011; 6:e22842. These integrins also play critical roles in non-cancer pathologies such as fibrosis and pathological angiogenesis. Weis et al., 2011; Hinz, 2013; Henderson et al., Nature Medicine 2013: 19:10.1038/nm.3282; Asano et al., J. Immunol 2005; 175: 7708-18; Ray, Nature Reviews Gastroenterology & Hepatology 2013:11:4; Avraamides et al., Nat Rev Cancer 2008; 8:604-617.

SUMMARY

An object of the present invention is to provide a bispecific antibody construct that simultaneously and specifically binds to integrin alpha-V and integrin α5, which are encoded by the distinct ITGAV and ITGA5 genes, respectively, in humans. In some embodiments, for example, where the antibody construct is conjugated to a chemotherapeutic or cytotoxic agent, the antibody construct may specifically bind integrin alpha-V and integrin α5 without inhibiting the activity of either or both targets. In other embodiments, for example, where the antibody construct is unconjugated to a chemotherapeutic or cytotoxic agent, the antibody construct may specifically bind integrin alpha-V and integrin α5 and inhibit their biological activities to a clinically beneficial extent.

Accordingly, in a first aspect, the invention features a bispecific antibody construct or a biologically active fragment thereof that includes (a) a first paratope that specifically binds an alpha-V integrin; and (b) a second paratope that specifically binds an α5 integrin. The epitope on the α5 integrin may be wholly contained within that protein. Alternatively, the epitope may reside at least partially within the β1 integrin that, in living systems, forms a heterodimer with α5. Any type of bispecific antibody is contemplated; for non-limiting examples of formats, see FIG. 11. More information about bispecific antibodies can be found in a review by Brinkmann et al., mAbs 9(2):182-212 (2017). See FIG. 2 of that review for an illustration of many bispecific antibody formats that have been used in the art and that could be utilized for the present bispecific antibody construct.

In one embodiment, the construct comprises an antigen binding fragment (Fab) portion that contains the first paratope and a single-chain variable fragment (scFv) portion that contains the second paratope. Either paratope may be from an anti-alpha-V antibody, such as abituzumab; the other paratope is from an anti-α5 antibody, such as volociximab. The bispecific construct may be bivalent, trivalent, tetravalent, or of higher valency.

The bispecific antibody constructs described herein can include, for example, one or more of the following complementarity determining regions (CDRs):

(a) within a light chain variable domain of the first paratope: RASQDISNYLA ($P_1V_L$CDR1; SEQ ID NO:1); YTSKIHS ($P_1V_L$CDR2; SEQ ID NO:2); QQGNTFPYT ($P_1V_L$CDR3; SEQ ID NO:3); or an amino acid sequence at least 80% identical to any of those three, or where there are zero, one or two amino acid deletions, additions, or substitutions in any of them;

(b) within a heavy chain variable domain of the first paratope: SFWMH ($P_1V_H$CDR1; SEQ ID NO:4); YIN-PRSGYTEYNEIFRD ($P_1V_H$CDR2; SEQ ID NO:5); FLGR-GAMDY ($P_1V_H$CDR3; SEQ ID NO:6); or an amino acid sequence at least 80% identical to any of those three, or where there are zero, one or two amino acid deletions, additions, or substitutions in any of them;

(c) within a light chain variable domain of the second paratope: TASSSVSSNYLH ($P_2V_L$CDR1; SEQ ID NO:7); STSNLAS ($P_2V_L$CDR2; SEQ ID NO:8); HQYLRSPPT ($P_2V_L$CDR3; SEQ ID NO:9); or an amino acid sequence at least 80% identical to any of those three, or where there are zero, one, or two amino acid deletions, additions, or substitutions in any of them; or (d) within a heavy chain variable domain of the second paratope: GFSLTDYGVH ($P_2V_H$CDR1; SEQ ID NO:10); VIWSDGSSTYNSALKS ($P_2V_H$CDR2; SEQ ID NO:11); HGTYYGMTTTGDALDY ($P_2V_H$CDR3; SEQ ID NO:12); or an amino acid sequence at least 80% identical to any of those three (e.g., there may be zero, one or two amino acid deletions, additions, or substitutions in any of them).

Regarding the framework regions (FRs), any of the bispecific antibody constructs described herein, and in particular any construct having one or more of the CDRs described above, can include one or more of the following framework regions:

(a) within a light chain variable domain contributing to the first paratope: DIQMTQSPSSLSASVGDRVTITC ($P_1V_L$FR1; SEQ ID NO:13); WYQQKPGKAPKLLIY ($P_1V_L$FR2; SEQ ID NO:14); GVPSRFSGSGSGTDYTFTISSLQPEDIATYYC (P₁V_LFR3; SEQ ID NO:15); FGQGTKVEIK (P₁V_LFR4; SEQ ID NO:16); or an amino acid sequence at least 80% identical to any of those three (e.g., there may be zero, one or two amino acid deletions, additions, or substitutions in any of them);

(b) within a heavy chain variable domain contributing to the first paratope:

QVQLQQSGAELAEPGASVKMSCKASGYTFS; (P₁V_HFR1; SEQ ID NO: 17)

WVRQAPGQGLEWIG; (P₁V_HFR2; SEQ ID NO: 18)

KATMTTDTSTSTAYMELSSLRSEDTAVYYCAS (P₁V_HFR3: SEQ ID NO:19), WGQGTTVTVSS (P₁V_HFR4; SEQ ID NO:20); or an amino acid sequence at least 80% identical to any of those four (e.g., there may be zero, one or two amino acid deletions, additions, or substitutions in any of them);

(c) within a light chain variable domain contributing to the second paratope: QIVLTQSPAIMSASLGERVTMTC (P₂V_LFR1; SEQ ID NO:21); WYQQKPGSAPNLWIY (P₂V_LFR2; SEQ ID NO:22); GVPARFSGSGSGTSYS-LTISSMEAEDAATYYC (P₂V_LFR3; SEQ ID NO:23); FGGGTKLEIK (P₂V_LFR4; SEQ ID NO:24); or an amino acid sequence at least 80% identical to any of those four (e.g., there may be zero, one or two amino acid deletions, additions, or substitutions in any of them); or (d) within a heavy chain variable domain contributing to the second paratope: QVQLKESGPGLVAPSQSLSITCTIS (P₂V_HFR1; SEQ ID NO:25); WVRQPPGKGLEWLV (P₂V_HFR2; SEQ ID NO:26); RMTIRKDNSKSQVFLIMNSLQTDDSAMYYCAR (P₂V_HFR3; SEQ ID NO:27); WGQGTSVTVSS (P₂V_HFR4; SEQ ID NO:28); or an amino acid sequence at least 80% identical to any of those four (e.g., there may be zero, one or two amino acid deletions, additions, or substitutions in any of them).

In a second embodiment, the second paratope, which binds and may inhibit the activity (e.g., at least partially neutralize the activity) of α5 or α5β1, can include one or more of the following CDRs:

(a) within a light chain variable domain of the second paratope, RASQSVSSYLA (P₁V_LCDR1; SEQ ID NO:33); DASNRAT (P₁V_LCDR2; SEQ ID NO:34); QQRSNWPLT (P₁V_LCDR3; SEQ ID NO:35); or an amino acid sequence at least 80% identical to any of those three, or where there are zero, one or two amino acid deletions, additions, or substitutions in any of them; and (b) within a heavy chain variable domain of the second paratope, SSSYWG (P₁V_HCDR1; SEQ ID NO:36); SIYYS-GRNYNNPSLKS (P₁V_HCDR2; SEQ ID NO:37); and HYYGSGSSYYYYDLD (P₁V_HCDR3; SEQ ID NO:38); or an amino acid sequence at least 80% identical to any of those three, or where there are zero, one or two amino acid deletions, additions, or substitutions in any of them.

In a third embodiment, the second paratope, which binds and may inhibit at least partially an activity of α5 (e.g., α5β1), can include one or more of the following CDRs:

(a) within a light chain variable domain of the second paratope: RASQSVSSYLA (P₁V_LCDR1; SEQ ID NO:33); DASNRAT (P₁V_LCDR2; SEQ ID NO:34); QQRSNWPLT (P₁V_LCDR3; SEQ ID NO:35); or an amino acid sequence at least 80% identical to any of those three, or where there are zero, one or two amino acid deletions, additions, or substitutions in any of them; and (b) within a heavy chain variable domain of the second paratope: SYAMH (P₁V_HCDR1; SEQ ID NO:39); VIS-FDGSNKNYADSVKG (P₁V_HCDR2; SEQ ID NO:40); and EYWGTYYYGMDV (P₁V_HCDR3; SEQ ID NO:41); or an amino acid sequence at least 80% identical to any of those three, or where there are zero, one or two amino acid deletions, additions, or substitutions in any of them.

In a fourth embodiment, the second paratope, which binds and may inhibit at least partially an activity of α5 (e.g., α5β1), can include one or more of the following CDRs:

(a) within a light chain variable domain of the second paratope: RASQSVSSYLA (P₁V_LCDR1; SEQ ID NO:33); DASNRAT (P₁V_LCDR2; SEQ ID NO:34); QQRSNWPLT (P₁V_LCDR3; SEQ ID NO:35); or an amino acid sequence at least 80% identical to any of those three, or where there are zero, one or two amino acid deletions, additions, or substitutions in any of them; and (b) within a heavy chain variable domain of the second paratope: STYAMH (P₁V_HCDR1; SEQ ID NO:42); VISYDGSNKYYADSVKG (P₁V_HCDR2; SEQ ID NO:43); and RESPPIYYYYGMDV (P₁V_HCDR3; SEQ ID NO:44); or an amino acid sequence at least 80% identical to any of those three, or where there are zero, one or two amino acid deletions, additions, or substitutions in any of them.

In the second, third, and fourth embodiments, the CDRs are as disclosed in U.S. Pat. No. 8,039,596, the entire content of which is incorporated by reference herein.

An antibody construct of the invention can also have one or more of the following characteristics: it may further include an Fc region, such as one derived from a human IgA or human IgG Fc region; it may be a chimera (with one or all variable domain sequences derived from a non-human animal, and the Fc region derived from a human); it may be fully human, humanized, or de-immunized; it may be divalent, trivalent, or tetravalent; and/or it may include a detectable marker. For example, an antibody construct can include an Fc portion and be chimeric; can be human and tetravalent; can be humanized and include a detectable marker; or have any other compatible combination of the features just mentioned or set out below.

In some embodiments, the construct comprises a first polypeptide comprising a first light chain variable domain linked to a light chain constant region, and a second polypeptide chain comprising, in order from amino to carboxy terminus, a first antibody heavy chain variable domain linked to a heavy chain constant region linked to an scFv, where the scFv contains, in either order, a second heavy chain variable domain that is different from the first heavy chain variable domain and is linked to a second light chain variable domain that is different from the first light chain variable domain. The first light and heavy chain variable domains form a paratope that binds to either integrin α5 (e.g., α5β1) or integrin alpha V. The second light and heavy chain variable domains form a second paratope that binds to the other integrin. An example of this construct with signal sequences (MELGLSWIFLLAILKGVQC; SEQ ID NO:29, and MRVPAQLLGLLLLWLPGTRC, SEQ ID NO:30) still attached to the respective amino termini is shown in FIGS. 12A and 12B. The sequence of FIG. 12A (SEQ ID NO:β1) is configured to include, in addition to the signal sequence SEQ ID NO: 29, the variable region of the heavy chain of a first paratope, the constant region of that heavy chain, a linker, the heavy chain variable region of a second paratope, a linker, and the light chain variable region of the second paratope. As one of ordinary skill in the art would recognize, the heavy and light chain variable regions of the second paratope would cooperate as an scFv that is covalently attached to the carboxy terminus of the heavy chain constant region. The light chain (including signal sequence SEQ ID NO:30) of the first paratope is shown in FIG. 12B (SEQ ID NO:32). In one embodiment, the invention includes a construct comprising two polypeptides, one of which is represented by the sequence shown in FIG. 12A (SEQ ID NO: β1), except lacking the signal sequence MELGLSWIFL-LAILKGVQC (SEQ ID NO:29) portion of SEQ ID NO: β1, and the other of which is represented by the sequence shown in FIG. 12B (SEQ ID NO: 32), except lacking the signal sequence MRVPAQLLGLLLLWLPGTRC (SEQ ID NO:30) portion of SEQ ID NO: 32.

In one aspect, the disclosure features a bispecific construct comprising an amino acid sequence that is at least 70%, at least 75%, at least 80%, at least 85%, at least 90%, or at least 95% identical to the amino acid sequence set forth in SEQ ID NO:63. In certain instances, the disclosure features a bispecific construct comprising an amino acid sequence set forth in SEQ ID NO:63 except having 1 to 20 (e.g., 1, 2, 3, 4, 5, 6, 7, 8, 9, 10, 11, 12, 13, 14, 15, 16, 17, 18, 19 or 20) amino acid substitutions (e.g., conservative amino acid substitutions). In certain instances, the substitutions are in the framework, constant, and/or linker region. In certain instances, the substitutions are in one or more of the CDRs.

In another aspect, the disclosure features a bispecific construct comprising an amino acid sequence that is at least 70%, at least 75%, at least 80%, at least 85%, at least 90%, or at least 95% identical to the amino acid sequence set forth in SEQ ID NO:64. In certain instances, the disclosure features a bispecific construct comprising an amino acid sequence set forth in SEQ ID NO:64 except having 1 to 20 (e.g., 1, 2, 3, 4, 5, 6, 7, 8, 9, 10, 11, 12, 13, 14, 15, 16, 17, 18, 19 or 20) amino acid substitutions (e.g., conservative amino acid substitutions). In certain instances, the substitutions are in the framework and/or constant region. In certain instances, the substitutions are in one or more of the CDRs.

In one aspect, the disclosure features a bispecific construct comprising: (1) an amino acid sequence that is at least 70%, at least 75%, at least 80%, at least 85%, at least 90%, or at least 95% identical to the amino acid sequence set forth in SEQ ID NO:63; and (2) an amino acid sequence that is at least 70%, at least 75%, at least 80%, at least 85%, at least 90%, or at least 95% identical to the amino acid sequence set forth in SEQ ID NO:64. In certain instances, the disclosure features a bispecific construct comprising an amino acid sequence set forth in SEQ ID NO:63 and/or 64 except having 1 to 20 (e.g., 1, 2, 3, 4, 5, 6, 7, 8, 9, 10, 11, 12, 13, 14, 15, 16, 17, 18, 19 or 20) amino acid substitutions (e.g., conservative amino acid substitutions). In certain instances, the substitutions are in the framework, constant, and/or linker region. In certain instances, the substitutions are in one or more of the CDRs.

In another aspect, the invention features nucleic acid that comprises a sequence or sequences that together encode all polypeptides of a bispecific antibody construct as described herein, or a portion thereof, or a set of nucleic acid molecules that together encode the polypeptides that make up the bispecific antibody construct. For example, the nucleic acid may encode a polypeptide comprising a heavy and/or light chain variable domain within the first or second paratope of any of the bispecific antibody constructs described herein. The nucleic acid may encode a polypeptide comprising a heavy chain variable domain of one of the paratopes, a heavy chain constant domain, and an scFv containing the heavy and light chain variable domains of the other paratope. As an example, the nucleic acid may encode a polypeptide comprising the amino acid sequence of FIG. 12A, with or without the signal sequence shown in that figure (or with a different signal sequence). Any signal sequence known in the art as useful for expressing antibody sequences can be used. The nucleic acid preferably includes appropriate expression control sequences operably linked to the coding sequence.

In another aspect, the invention features an expression vector that includes the nucleic acid described above or elsewhere herein.

In another aspect, the invention features a host cell (e.g., a bacterial, yeast, insect, or mammalian cell) comprising the expression vector described above or elsewhere herein.

In another aspect, the invention features a protein expression system that includes the host cell described above or elsewhere herein.

In another aspect, the invention features a pharmaceutical composition that includes a bispecific antibody construct described herein and a pharmaceutically acceptable carrier. The composition can be formulated for administration to a patient through any route (e.g., it may be formulated for oral, nasal, intramuscular, intraperitoneal, or intravascular (e.g., intravenous), administration).

In another aspect, the invention features a kit that includes a bispecific antibody construct described herein and instructions for use in treatment.

In another aspect, the invention features a method of making a bispecific antibody construct described herein. The method can include a step of culturing the host cell as described herein under conditions in which the nucleic acid encoding one or both polypeptide(s) making up the bispecific antibody are expressed.

In another aspect, the invention features a method of treating cancer. The method can include administering a therapeutically effective amount of a bispecific antibody construct described herein to a patient in need thereof (e.g., a patient who has a cancer in which either integrin is implicated in the pathogenesis or progression of the disease, including of any of the following types of cancer: prostate, kidney, breast, melanoma, pancreatic, ovarian, colonic, cervical, head and neck, lung, gastric, endometrial, bone and brain metastases, soft-tissue sarcoma, osteosarcoma, hepatoma, basal cell carcinoma, glioblastoma, angiosarcoma, T-cell lymphoma, and multiple myeloma).

In another aspect, the invention features a method of treating a non-malignant condition in which either alpha v or alpha 5 integrin is expressed and implicated in the pathogenesis or progression of the disease. Such diseases include, e.g., non-malignant fibrotic diseases involving lung, liver, heart, kidney, bone marrow, or skin, such as scleroderma, chronic graft-vs-host disease, liver fibrosis, and interstitial lung disease. The general category of non-malignant diseases treatable with the present antibodies also includes, e.g., conditions involving pathological angiogenesis, such as proliferative retinopathy, wet macular degeneration, arteriovenous malformations, and cavernous hemangiomas. The method of treatment can include administering a therapeutically effective amount of a bispecific antibody construct described herein to a patient in identified need thereof.

As used in this specification and the appended claims, the singular forms "a," "an" and "the" include a plurality of like or unlike referents unless the context clearly dictates otherwise. For example, when we say the invention features "a method," we do not mean only one single method but rather a plurality of methods that may or may not share common steps. When we refer to "a host cell," that may be a single host cell or a plurality of cells that may be highly similar or different (e.g., a mixture of different cell types).

Other features and advantages of the invention will be apparent from the following detailed description, and from the claims.

All publications mentioned herein are hereby incorporated by reference in their entirety.

BRIEF DESCRIPTION OF THE DRAWINGS

FIGS. 1A and 1B are graphs summarizing the results obtained in migration and adhesions assays with PC-3 prostate cancer cells (FIG. 1A) and DU-145 prostate cancer cells (FIG. 1B). The cells were assayed in the presence of serum-free medium (SFM, negative control) or human bone marrow-mesenchymal stromal cell conditioned media (hBM-MSC CM), a matched isotype control antibody (Iso) and antibodies that specifically bind integrin β1 (β1), integrin β3 (β3), integrin alpha 5 (α5), integrin alpha 6 (α6), integrin alpha-V (αV), or both integrin α5 and integrin alpha-V (α5αV).

FIG. 3A is a photograph of a reduced SDS-PAGE gel showing the purity of the bispecific antibody. FIG. 3B is a table containing data concerning binding studies that demonstrate correlation of binding between anti-α5, anti-alpha-V, and bispecific anti-α5-alpha-V antibodies across a panel of cell lines (PC-3, C42B, DU-145, VCAP, and RWPE-1). The mean fluorescent intensities (MFI) for the α5, alpha-V, and bispecific ITGA5B1xAV stained cell populations for each cell line were calculated from the flow cytometry data. Then, a correlation coefficient between the sum of α5 and alpha-V MFIs and the bispecific ITGA5B1xAV was calculated.

FIGS. 6A and 6B are a pair of bar graphs showing the results of cellular migration studies. Endothelial migration was induced by prostate cancer-hBM-MSC co-culture for 24 hours with integrin blockade on DU-145 cells (FIG. 6A) or on HUVEC endothelial cells (FIG. 6B). Neutralization was performed with 10 µg/mL of total antibody. The bispecific antibody was superior to the combined monoclonal antibodies in inhibiting endothelial cell migration to co-culture. ***: $P \leq 0.001$.

FIG. 12A is a representation of an amino acid sequence (SEQ ID NO:47) including a signal sequence and the heavy chain of an IgG construct that binds alpha-V, linked to an scFv domain that binds α5β1. Sub-regions, including the signal sequence (which would be cleaved off when the antibody is secreted from a host cell), CDRs and FRs of the heavy chain variable domain targeting alpha-V, and an IgG heavy chain constant region, are marked. At the carboxy end of the heavy chain constant region is a linker sequence GGGGSGGGGS (SEQ ID NO:45), followed by an scFv targeting α1β1. The scFv sequence targeting α5β1 comprises a heavy chain variable region with CDRs and FRs identified, followed by another linker (GGGGSGGGGSGGGGS; SEQ ID NO:46), followed by a light chain variable region with CDRs and FRs identified.

FIG. 12B is a representation of an amino acid sequence (SEQ ID NO:48) that includes a signal sequence and the variable light chain of a construct that binds alpha-V. Two polypeptide having the sequence shown in FIG. 12A and two polypeptides having the sequence shown in FIG. 12B (minus their respective signal sequences) would together form a tetravalent, bispecific, IgG-scFv antibody targeting the α5 integrin (α5β1) and the alpha-V integrin.

FIGS. 12C-1 and 12C-2 are a table delineating the hypervariable CDRs and the FRs of the sequences shown in FIGS. 12A and 12B, and variants thereof.

Figure 14:
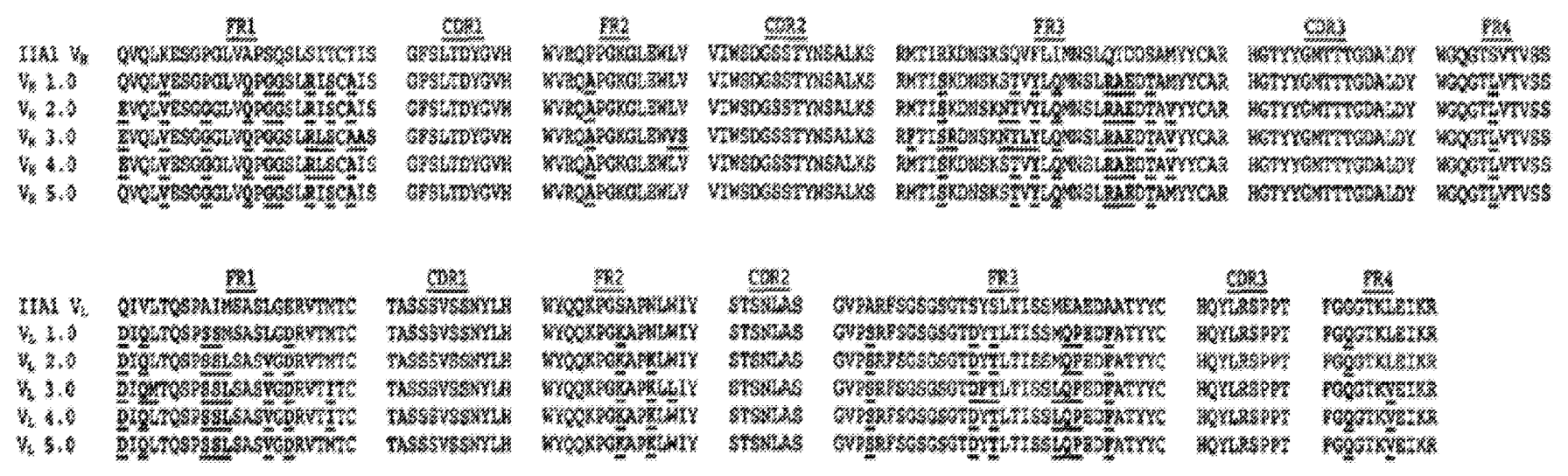

FIG. 14 is an alignment of sequences including variants of CDRs in the variable regions of heavy and light chains targeting α5β1. The uppermost sequence of each chain represents a murine sequence and those beneath it represent five variants that are humanized antibodies, as disclosed in U.S. Pat. No. 7,276,589, the entire content of which is hereby incorporated by reference herein. The uppermost VH sequence is assigned SEQ ID NO:49. The five VH sequences below it are assigned SEQ ID NOs:50-54, in order. The uppermost VL sequence is assigned SEQ ID NO:55. The five VH sequences below it are assigned SEQ ID NOs:56-60, in order.

FIG. 20A is a pair of nucleotide sequences, the upper one (SEQ ID NO:61) encoding the polypeptide shown in FIG. 12A, including its signal sequence, and the lower one (SEQ ID NO:62) encoding the polypeptide shown in FIG. 12B, including its signal sequence.

FIG. 20B is a pair of amino acid sequences, the upper one (SEQ ID NO:63) being the mature form (i.e., without the signal sequence) of the polypeptide shown in FIG. 12A, and the lower one (SEQ ID NO:64) being the mature form of the polypeptide shown in FIG. 12B.

DETAILED DESCRIPTION

Figure 2A:
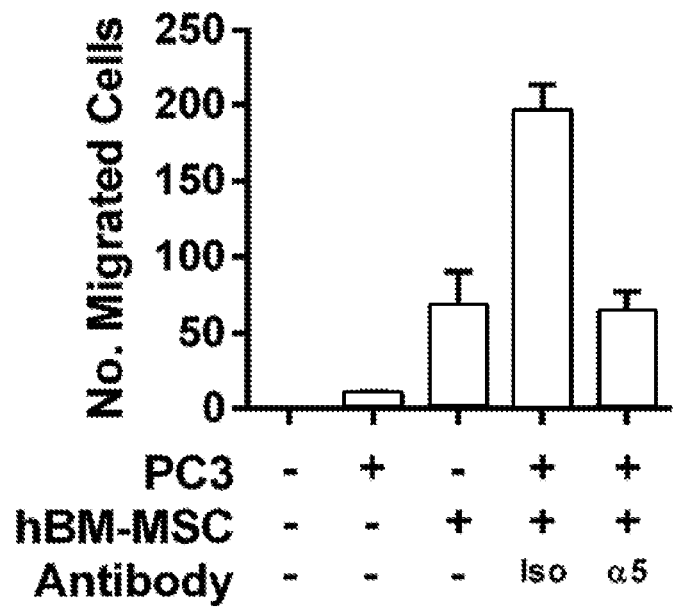
FIGS. 2A and 2B are a pair of bar graphs illustrating that human umbilical vein endothelial cell (HUVEC) migration induced by prostate cancer-hBM-MSC interaction is regulated by integrins α5 (FIG. 2A) and alpha-V (FIG. 2B).

The studies described below indicate cooperativity between the α5 integrin and the alpha-V integrin in a range of cancer-specific behaviors, including tumor-stromal interactions and the induction of an angiogenic response required for the survival and progression of these tumors. These two integrins are also implicated as contributing to many non-cancer pathologies related to fibrosis or angiogenesis. For example, alpha-V is critical to the generation of autocrine TGF-beta signaling in scleroderma fibroblasts and in the generation of myofibroblasts in liver fibrosis and interstitial lung disease (Henderson et al., 2013; Asano et al., 2005; Ray, 2013). Integrin alpha-V and α5 are master regulators of vascular endothelial growth factor (VEGF) and fibroblast growth factor (FGF)-driven angiogenesis, such as in angiogenesis pathologies including, e.g., proliferative retinopathy, wet macular degeneration, arteriovenous malformations, and cavernous hemangiomas.

As detailed below, a bispecific antibody containing an antigen-binding domain that binds to and neutralizes α5 integrin (or its obligate heterodimeric form α5β1) combined with a different antigen-binding domain that binds to and neutralizes alpha-V integrin was found to result in markedly enhanced anti-tumor activity compared to either single agent monospecific antibody, or a mixture of the two monospecific antibodies, in a range of tumor biology assays, as detailed below.

The central hypothesis pertinent to the invention described herein is that a bispecific antibody that simultaneously targets α5 (or α5β1) and alpha-V integrin would be significantly superior to combinations of individual α5 and alpha-V monospecific antibodies by virtue of enhanced binding precision to these integrins that require close physical proximity on the cell membrane for their optimal cooperativity, e.g. in focal adhesions. Additional advantages of a bispecific construct over combinations of monospecific antibodies likely include increased binding affinity as a result of the localization of the remaining binding site to the cell membrane following binding of the first, and increased binding specificity as a result of binding two or more cell surface antigens. Increased binding affinity and residence time when both antigens are engaged simultaneously by the two pharmacophores in a bispecific antibody is referred to as cross-arm binding efficiency. The spatial exclusion of one antibody by another, as well as asymmetric pharmacokinetic and pharmacodynamic properties, could account for suboptimal results with monospecific antibodies in combination. The virtues of a bispecific antibody may therefore translate to enhanced anti-tumor efficacy and reduced toxicity in vivo, with improved ease of administration as well as simplified pharmacokinetic and pharmacodynamic monitoring. The below data demonstrate the superiority of a prototypical bispecific α5β1+alpha-V antibody construct over combinations of monospecific α5/α5β1 and alpha-V antibodies in a range of tumor biology assays, including tumor-stromal interactions and induction of angiogenesis.

Integrin alpha-V: Integrins are heterodimeric integral membrane proteins composed of an alpha chain and a beta chain. Integrin alpha-V (sometimes referred to as av, aV, αv, or αV) undergoes post-translational cleavage to yield disulfide-linked heavy and light chains that combine with multiple integrin beta chains to form different integrins. The monoclonal antibodies intetumumab and abituzumab target this protein, which is found on some tumor cells (Elez et al., *Annals of Oncology,* 26(1):132-140, 2015).

Integrin α5: Integrin α5 (sometimes referred to as alpha 5 or α5) is a protein that, in humans, is encoded by the ITGA5 gene. The α5 chain undergoes post-translational cleavage in the extracellular domain to yield disulfide-linked light and heavy chains that join with beta 1 (β1) to form a fibronectin receptor referred to as α5β1.

Figure 10:
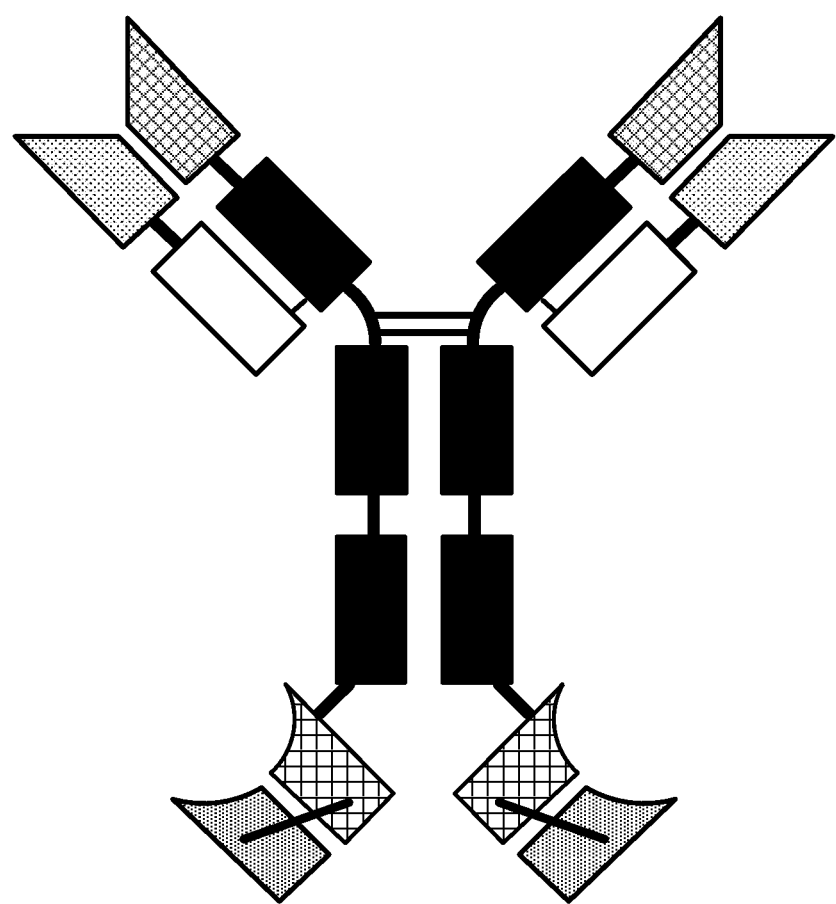
FIG. 10 is a schematic diagram showing a format of one embodiment of a bispecific antibody of the invention. Stable scFvs are attached to the constant region of an IgG, with the resulting construct being tetravalent.
Figure 11:
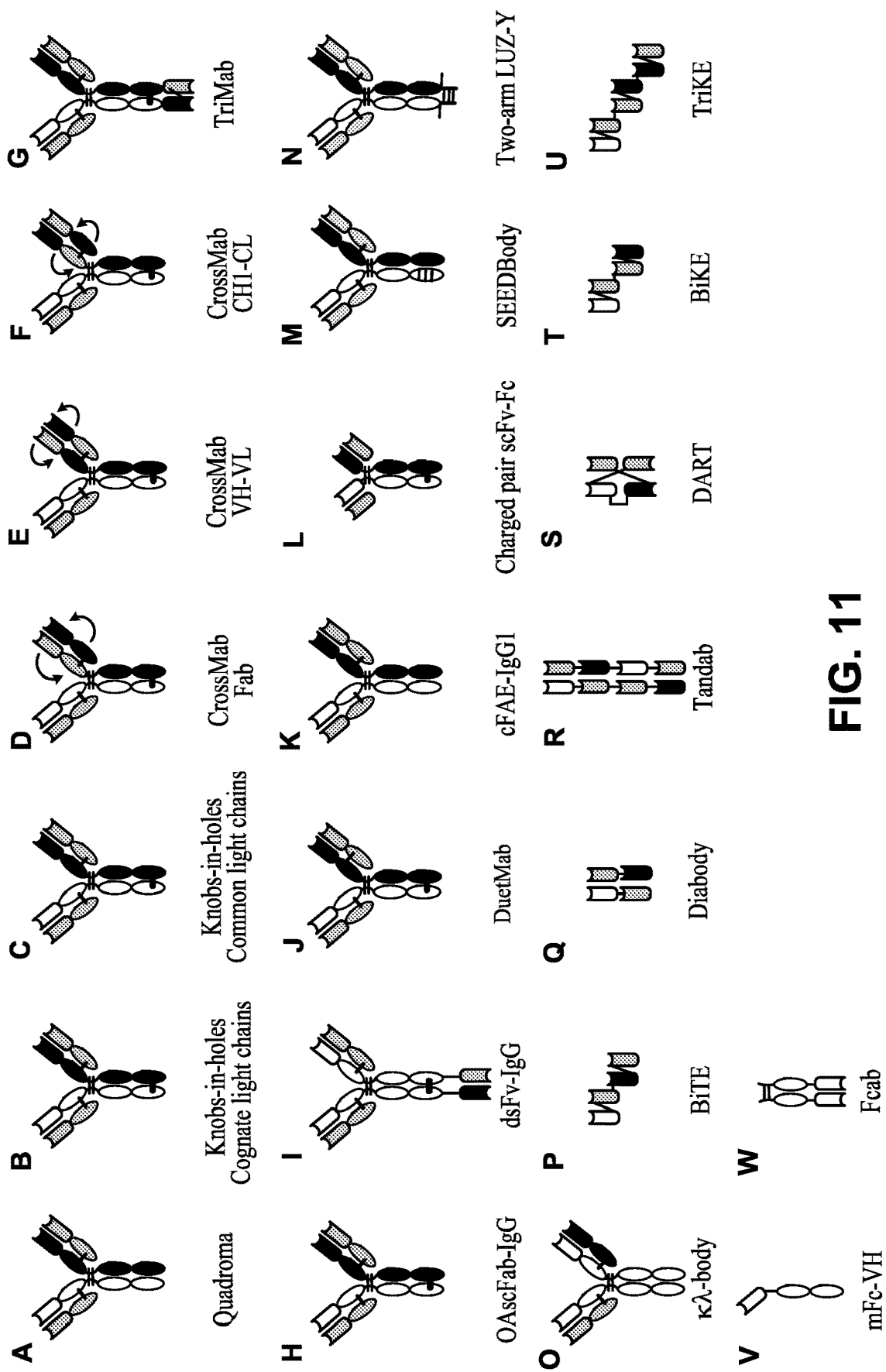
FIG. 11 is a schematic diagram derived from FIG. 1 of Liu et al., Front. Immunol (2017) doi.org/10.3389/fimmu.2017.00038, showing various formats of bispecific antibodies and scaffolds useful in the present invention; a bispecific antibody that specifically binds integrin alpha-V and integrin α5 can be engineered in any of these formats or assume the configuration of any of these scaffolds. (A) is a bispecific quadroma, which can be generated by somatic fusion of two hybridomas; (B-J) are bispecific formats developed by using a knob-in-hole (KiH) Fc heterodimerization strategy; (K) is a bispecific IgG1 developed by controlled Fab-arm exchange; (L) is a bispecific Fc-fusion construct developed by electrostatic optimization; (M-O) are bispecific formats developed by strand exchange, insertion of cleavage motif and expressing two light chains with a single heavy chain; and (P-W) are other bispecific or multispecific scaffolds. Abbreviations: OAscFab-IgG represents a one-arm single-chain Fab-immunoglobulin gamma (IgG); dsFv-IgG represents a disulfide stabilized Fv-IgG; Cfae-IgG1 represents a controlled Fab-arm exchanged IgG1; scFv-Fc represents a charged pair single-chain Fv-Fc fusion; SEEDbody represents a strand-exchange engineered domain body; LUZ-Y represents a two-arm leucine zipper heterodimeric monoclonal antibody; κγ-body represents a kappa lambda body; BiTE represents a bispecific T-cell engager; BiKE/TriKE represents bispecific and trispecific killer cell engagers, respectively; DART represents dual-affinity retargeting molecules; mFc represents a monomericFc; and Fcab represents an Fc antigen binding domain.
Figure 13:
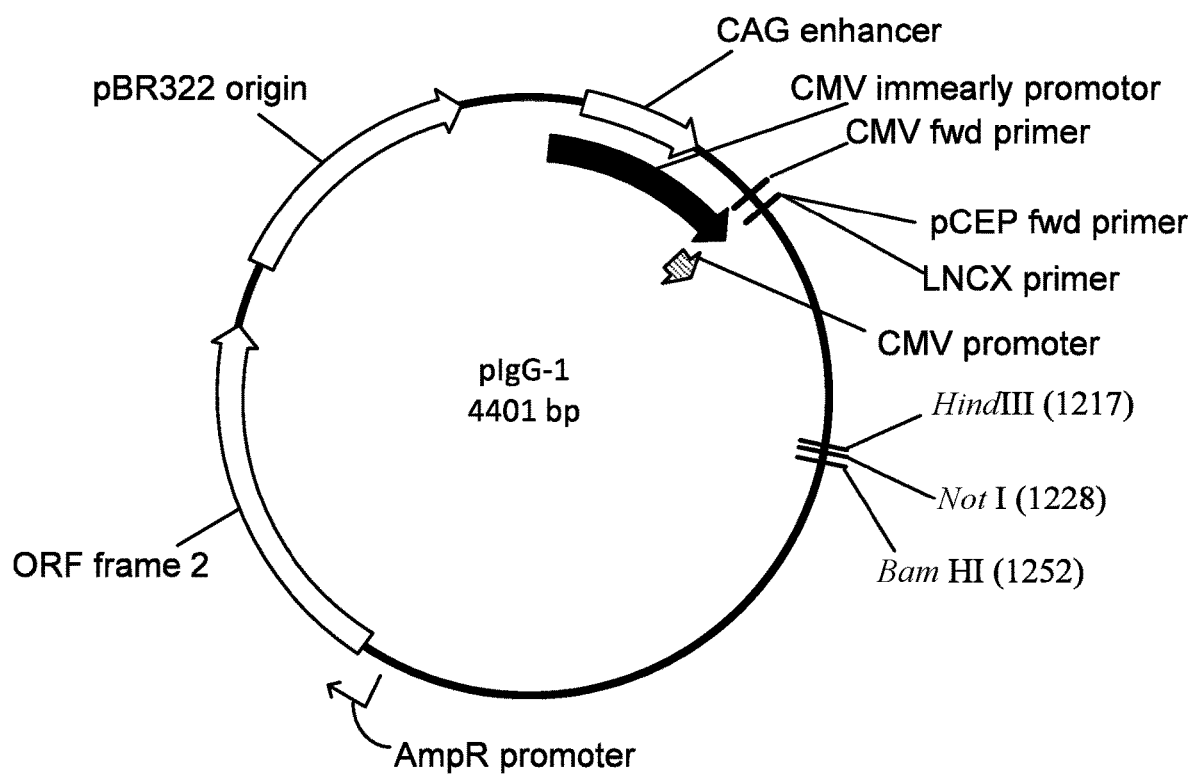
FIG. 13 is a representation of an expression vector (a plasmid) useful in expressing nucleic acid sequences encoding heavy and/or light chains of an antibody construct described herein.

Configurations of the antibody constructs: An antibody construct of the present invention can be configured in various ways, provided it selectively or specifically binds integrin alpha-V and integrin α5. Examples of useful constructs are illustrated in FIGS. 10 and 11. Examples of antibody fragments that may be incorporated in the present antibody constructs include but are not limited to Fv, Fab, Fab', Fab'-SH, F(ab')$_2$; diabodies; linear antibodies; and single-chain Fv antibody molecules (scFv). Methods of generating nucleic acid constructs that encode a bispecific antibody construct or a part thereof and methods of expressing those constructs are known in the art. See, e.g., Spiess et al., (*Mol. Immunol.* 67:95-106, 2015); Han et al., (*Sci. Rep.* 7:8360, 2017); Fan et al. (*J. Hematol. Oncol.* 8:130, 2015); Kontermann (*Acta Pharmacologica Sinica* 26(1):1-9, 2005); and Kontermann and Brinkmann (*Drug Discovery Today* 20(7):838-847, 2015).

An "antibody construct that binds to the same epitope" as a reference antibody refers to an antibody construct that blocks binding of the reference antibody to its antigen in a competition assay by 50% or more, and conversely, the reference antibody blocks binding of the antibody construct to its antigen in a competition assay by 50% or more. The details of the competition assay to be used for this determination are set out herein.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (KD). Affinity can be measured by common methods known in the art, including those described herein. Specific illustrative and exemplary embodiments for measuring binding affinity are described herein.

The antibody constructs of the invention will be capable of binding integrin alpha-V and integrin α5 with sufficient affinity to be useful as diagnostic and/or therapeutic agents. In some embodiments, the extent of binding of an antibody construct of the invention to an unrelated protein (i.e., a protein other than integrin alpha-V or integrin α5) is less than about 10% of the binding of the antibody to integrin alpha-V or integrin α5 as measured, e.g., by a radioimmunoassay (RIA). In certain embodiments, an antibody that binds to integrin alpha-V or integrin α5 has a dissociation constant (KD) of ≤1 μM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M), where KD is determined using a surface plasmon resonance technique (e.g., with a Biacore™ instrument) in which the antigen is immobilized, the antibody serves as analyte, and the following conditions are used: 37° C., 0.05% Tween® 20 polyethylene glycol sorbitan monolaurate, 20 mM N-(2-acetamido)-2-aminoethanesulfonic acid (ACES buffer), 150 mM NaCl, pH 7.4. In certain embodiments, an anti-integrin alpha-V, anti-integrin α5 antibody binds to an epitope of integrin alpha-V or integrin α5 that is conserved among those integrins from different species (e.g., human and non-human primate or human and murine).

An "affinity matured" antibody refers to an antibody with one or more alterations in the variable region, e.g., in one or more hypervariable regions (HVRs), compared to a parent antibody which does not possess such alterations, such alterations resulting in an improvement in the affinity of the antibody for antigen.

As used herein, a "bispecific antibody construct" comprises or consists of a protein or complex of proteins having a sequence or sequences that specifically and simultaneously bind two molecular targets. In the context of the present invention, the first target is integrin alpha-V and the second target is integrin α5 (alone or when heterodimerized with (β1). The protein may be further configured and modified as described herein (e.g., modified to include a detectable label). The bispecific antibody constructs of the invention can be more simply referred to as antibodies, antibody constructs or constructs. The term "construct" is used, in part because the compositions can be constructed using genetic engineering and can be non-naturally occurring. Accordingly, any of the antibody constructs described herein, nucleic acids that encode them, related expression vectors and host cells can be non-naturally occurring.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The term "hypervariable region" or "HVR" as used herein refers to each of the regions of an antibody variable domain that is hypervariable in sequence and/or forms a structurally defined loop ("hypervariable loop") and/or contains the antigen-contacting residues ("antigen contacts"). Generally, antibodies comprise six HVRs (also known as "complementarity determining regions" or "CDRs"): three in the VH (H1, H2, H3), and three in the VL (L1, L2, L3). Exemplary HVRs herein include: (a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917, 1987); (b) CDRs occurring at amino acid residues 24-34 (L1), 50-56 (L2), 89-97 (L3), β1-35b (H1), 50-65 (H2), and 95-102 (H3) (Kabat et al., Sequences of Proteins of Immunological Interest, 5th Ed. Public Health Service, National Institutes of Health, Bethesda, Md. (1991)); (c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262:732-745, 1996); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

The term "knob-into-hole" or "KnH" technology as used herein refers to the technology directing the pairing of two polypeptides together in vitro or in vivo by introducing a protuberance (knob) into one polypeptide and a cavity (hole) into the other polypeptide at an interface where they interact. For example, KnHs have been introduced in the Fc:Fc binding interfaces, $C_L$:$C_{H1}$ interfaces, and $V_H$/$V_L$ interfaces of antibodies (see, e.g., US 2011/0287009, US2007/0178552, WO 96/027011, WO 98/050431, and Zhu et al., 1997, Protein Science 6:781-788). In some embodiments, KnHs drive the pairing of two different heavy chains together during the manufacture of multispecific antibodies. For example, multispecific antibodies having KnH in their Fc regions can further comprise single variable domains linked to each Fc region, or further comprise different heavy chain variable domains that pair with similar or different light chain variable domains. KnH technology can be also be used to pair two different receptor extracellular domains together or any other polypeptide sequences that comprise different target recognition sequences (e.g., including affibodies, peptibodies and other Fc fusions).

The term "knob mutation" as used herein refers to a mutation that introduces a protuberance (knob) into a polypeptide at an interface in which the polypeptide interacts with another polypeptide. In some embodiments, the other polypeptide has a hole mutation.

The term "hole mutation" as used herein refers to a mutation that introduces a cavity (hole) into a polypeptide at an interface in which the polypeptide interacts with another polypeptide. In some embodiments, the other polypeptide has a knob mutation.

As is known in the art, naturally occurring immunoglobulins include a heavy chain and a light chain, each of which is further divided into a constant region and a variable region. Within the variable regions, there are three hypervariable regions, also known as "complementarity-determining regions" or CDRs, interspersed within four "framework" regions (FRs). It is the CDRs that are primarily responsible for binding a target molecule, which may be an antigen. The sequence within the antibody that binds the target molecule is the "paratope," and the sequence within the target molecule that is bound is the "epitope." The CDRs of each chain are typically referred to as CDR1, CDR2, and CDR3, numbered sequentially from the N-terminus, and the variable regions of the heavy and light chains can be abbreviated $V_H$ and $V_L$, respectively. As the constructs of the invention are bispecific, they will include two paratopes. Accordingly, the first CDR in the variable region of the light chain of the first paratope may be abbreviated as "$P_1V_LCDR1$." The second CDR would be "$P_1V_LCDR2$." The first CDR in the variable region of the heavy chain of the second paratope would be "$P_2V_HCDR1$," and so forth.

A "single chain Fv" or "scFv" denotes a binding entity in which the variable regions of the heavy ($V_H$) and light ($V_L$) chains of a conventional antibody have been engineered to form one chain. A linker sequence is typically inserted between the $V_H$ and $V_L$ regions of an scFv to facilitate proper folding and creation of an active paratope.

Sequences: With regard to useful sequences, the present constructs can include CDRs, FRs, and biologically active fragments or other variants thereof from previously generated or newly generated immunoglobulins. For example, the CDRs within a paratope that binds integrin alpha-V can include those described in U.S. Pat. No. 8,562,986, the entire content of which is hereby incorporated by reference herein. The CDRs within a paratope that binds integrin α5 or α5β1 can include those described in U.S. Pat. No. 7,276,589, the content of which, as noted above, is incorporated herein by reference.

"Percent (%) amino acid sequence identity" with respect to a reference polypeptide sequence is defined as the percentage of amino acid residues in a candidate sequence that are identical to corresponding amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

A "human antibody" is one that possesses an amino acid sequence that corresponds to that of an antibody produced by a human or a human cell or derived from a non-human source that utilizes human antibody repertoires or other human antibody-encoding sequences. It need not be a naturally-occurring antibody. This definition of a human antibody specifically excludes a humanized antibody comprising non-human antigen-binding residues.

A "human consensus framework" is a framework that represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., Sequences of Proteins of Immunological Interest, Fifth Edition, NIH Publication 91-3242, Bethesda Md. (1991), vols. 1-3. In some embodiments, for the VL, the subgroup is subgroup kappa I as in Kabat et al., supra. In some embodiments, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization. Immunoglobulins generated in a non-human animal (e.g., a rodent or non-human primate) can be humanized and/or de-immunized according to standard methods. In some instances, the humanized and/or de-immunized antibody constructs will be chimeric, in that they will include sequences (e.g., variable domain sequences) found in the non-human immunoglobulins from which they were generated as well as sequences (e.g., constant domain sequences) found in human immunoglobulins. In other embodiments, the antibody constructs of the present invention can include CDRs and FRs from a fully human immunoglobulin.

To de-immunize an antibody, one can identify and remove human T-cell epitopes from the original immunoglobulin (e.g., a mouse antibody), replacing them with alternate sequences that are not human T-cell epitopes. De-immunization differs from humanization, which replaces original immunoglobulin (e.g., mouse antibody) sequences with human consensus sequences. De-immunization techniques useful in making the present constructs can be found, for example, in WO 98/52976, WO 00/34317 and WO 02/69232.

Additional Moieties: The bispecific antibody constructs described herein can also include one or more additional moieties. For example, the constructs can include a detectable label and/or a moiety that extends the construct's circulating half life (e.g., modified human serum albumin). A "detectable label" is a composition detectable by spectroscopic, photochemical, biochemical, immunochemical, chemical, or other physical means. For example, a detectable label within a bispecific antibody construct of the present invention can be a fluorescent dye, an electron-dense reagent, a radioisotope, an enzyme (e.g., an enzyme commonly used in an ELISA), biotin, digoxigenin, a hapten, or any other protein or non-protein entity that can be made detectable. The radioisotope may be, for example, $^{3}H$, $^{14}C$, $^{32}P$, $^{35}S$, or $^{125}I$. In some cases, radioisotopes can be employed not only because they are detectable, but also because they can be toxic to cells in their vicinity.

The detectable labels may be incorporated into the bispecific antibody constructs at a number of positions, and any method known in the art for conjugating the construct to the label may be employed. For example, one could use a method described by Hunter et al. (*Nature*, 144:945, 1962); David et al. (*Biochemistry*, 13:1014, 1974); Pain et al. (*J. Immunol. Meth.*, 40:219, 1981); or Nygren (*J. Histochem. and Cytochem.*, 30:407, 1982). The lifetime of radiolabeled antibody constructs may be extended by adding a substance that stabilizes the radiolabeled construct by, for example, protecting it from degradation. Any substance or combination of substances that stabilizes the construct may be used, including those disclosed in U.S. Pat. No. 5,961,955.

An antibody construct may be isolated. An "isolated" antibody is one that has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., J. Chromatogr. B 848:79-87 (2007).

Nucleic Acids and Expression Vectors:

The nucleic acids and expression vectors described herein may be "isolated" by virtue of being separated from a component of their natural environment (insofar as that may exist). An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

Host Cells and Expression Systems: Host cells are transfected or transformed with expression or cloning vectors described herein for bispecific antibody production and cultured in conventional nutrient media modified as appropriate for inducing promoters, selecting transformants, or amplifying the genes encoding the desired sequences. One of ordinary skill in the art can, without undue experimentation, select the culture conditions, such as medium, temperature, pH and the like. In general, principles, protocols, and practical techniques for maximizing the productivity of cell cultures can be found in Mammalian Cell Biotechnology: a Practical Approach, M. Butler, ed. (IRL Press, 1991) and Sambrook et al., supra.

Methods of eukaryotic cell transfection and prokaryotic cell transformation are known to the ordinarily skilled artisan, for example, those that use $CaCl_2$ or $CaPO_4$, those that are liposome-mediated, and electroporation. Depending on the host cell used, transformation is performed using standard techniques appropriate to such cells. The calcium treatment employing calcium chloride, as described in Sambrook et al., supra, or electroporation is generally used for prokaryotes. Infection with *Agrobacterium tumefaciens* is used for transformation of certain plant cells, as described by Shaw et al. (*Gene*, 23:315, 1983) and WO 89/05859 published Jun. 29, 1989. For mammalian cells without such cell walls, the calcium phosphate precipitation method of Graham and van der Eb (*Virology*, 52:456-457, 1978) can be employed. General aspects of mammalian cell host system transfections have been described in U.S. Pat. No. 4,399,216. Transformations into yeast are typically carried out according to the method of Van Solingen et al. (*J. Bact.*, 130:946, 1977) and Hsiao et al. (*Proc. Natl. Acad. Sci. USA*, 76:3829, 1979). However, other methods for introducing DNA into cells, such as by nuclear microinjection, electroporation, bacterial protoplast fusion with intact cells, or polycations, e.g., polybrene, polyomithine, may also be used. For various techniques for transforming mammalian cells, see Keown et al. (*Methods in Enzymology*, 185:527-537, 1990) and Mansour et al. (*Nature*, 336:348-352, 1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635). Other suitable prokaryotic host cells include *Erwinia*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. licheniformis* (e.g., *B. licheniformis* 41P disclosed in DD 266,710 published Apr. 12, 1989), *Pseudomonas* such as *P. aeruginosa*, and *Streptomyces*. These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including *E. coli* W3110 strain 1A2, which has the complete genotype tonA; *E. coli* W3110 strain 9E4, which has the complete genotype tonA ptr3; *E. coli* W3110 strain 27C7 (ATCC 55,244), which has the complete genotype tonA ptr3 phoA E15 (argF-lac)169 degP ompT kanr; *E. coli* W3110 strain 37D6, which has the complete genotype tonA ptr3 phoA E15 (argF-lac)169 degP ompT rbs7 ilvG kanr; *E. coli* W3110 strain 40B4, which is strain 37D6 with a non-kanamycin resistant degP deletion mutation; and an *E. coli* strain having mutant periplasmic protease disclosed in U.S. Pat. No. 4,946,783 issued Aug. 7, 1990. Alternatively, in vitro methods of cloning, e.g., PCR or other nucleic acid polymerase reactions, are suitable.

In addition to prokaryotes, eukaryotic microbes such as filamentous fungi or yeast are suitable cloning or expression hosts for ADAMS-encoding vectors. *Saccharomyces cerevisiae* is a commonly used lower eukaryotic host microorganism. Others include *Schizosaccharomyces pombe* (Beach and Nurse, *Nature,* 290:140, 1981); EP 139,383 published May 2, 1985); *Kluyveromyces* hosts (U.S. Pat. No. 4,943, 529; Fleer et al., *Bio/Technology,* 9: 968-975, 1991)) such as, e.g., *K. lactis* (MW98-8C, CBS683, CBS4574; Louvencourt et al. (I Bacteriol., 737, 1983), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Vanden Berg et al. (*Bio/Technology,* 8:135, 1990), *K. thermotolerans,* and *K. marxianus; yarrowia* (EP 402,226); *Pichia pastoris* (EP 183,070; Sreekrishna et al. (*J. Basic Microbiol.,* 28:265-278, 1988); *Candida; Trichoderma reesia* (EP 244,234); *Neurospora crassa* (Case et al., *Proc. Natl. Acad. Sci. USA,* 76:5259-5263, 1979); *Schwanniomyces* such as *Schwanniomyces occidentalis* (EP 394,538 published Oct. 31, 1990); and filamentous fungi such as, e.g., *Neurospora, Penicillium, Tolypocladium* (WO 91/00357 published Jan. 10, 1991), and *Aspergillus* hosts such as *A. nidulans* (Ballance et al., *Biochem. Biophys. Res. Commun.,* 112:284-289, 1983; Tilburn et al. (*Gene,* 26:205-221, 1983; Yelton et al., *Proc. Natl. Acad. Sci. USA,* 81:1470-1474, 1984) and *A. niger* (Kelly and Hynes, *EMBO J.,* 4:475-479, 1985). Methylotropic yeasts are suitable herein and include, but are not limited to, yeast capable of growth on methanol selected from the genera consisting of *Hansenula, Candida, Kloeckera, Pichia, Saccharomyces, Torulopsis,* and *Rhodotorula*. A list of specific species that are exemplary of this class of yeasts may be found in C. Anthony, The Biochemistry of Methylotrophs, 269 (1982).

Suitable host cells for the expression of glycosylated antibodies are derived from multicellular organisms. Examples of invertebrate cells include insect cells such as Drosophila S2 and Spodoptera Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., J. Gen Virol., 36:59 (1977)); Chinese hamster ovary cells/-DHFR (CHO, Urlaub and Chasin, Proc. Natl. Acad. Sci. USA, 77:4216 (1980)); mouse sertoli cells (TM4, Mather, Biol. Reprod., 23:243-251 (1980)); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

The terms "host cell," "host cell line," and "host cell culture," which may be used interchangeably, refer to cells into which exogenous nucleic acid (e.g., a nucleic acid molecule or expression vector, as described herein) has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, as they may contain mutations. Mutant progeny that have substantially the same function or biological activity as screened or selected for in the originally transformed cell are included herein.

Pharmaceutical Compositions and Kits:

As noted, the invention features kits that includes a bispecific antibody construct as described herein and instructions for use. The instructions may be in the form of a "package or packet insert," which refers to information and instructions customarily included in commercial packages of therapeutic products, that contains information about the indications, usage, dosage, administration, combination therapy, contraindications, and/or warnings concerning the use of such therapeutic products. The term "package insert" is also used to refer to instructions customarily included in commercial packages of diagnostic products that contain information about the intended use, test principle, preparation and handling of reagents, specimen collection and preparation, calibration of the assay and the assay procedure, performance and precision data such as sensitivity and specificity of the assay.

Methods of Treatment: The compositions described herein can be used to inhibit angiogenesis whenever it is harmful (e.g., in the context of vascularizing a tumor). While the compositions described herein are not limited to those that achieve a clinical result through any particular cellular mechanism, it is expected that directly targeting integrins expressed by cancer cells or other cells within a tumor (e.g., stromal cells such as cancer-associated fibroblasts) will block the adhesion, survival, proliferation, invasion, and/or migration of cancer cells. The constructs may also enhance the function of the immune system by blocking immunosuppressive signaling in the cancer-associated microenvironment.

"Patient response" or "response" (and grammatical variations thereof) can be assessed using any endpoint indicating a benefit to the patient, including, without limitation, (1) inhibition, to some extent, of disease progression, including slowing down and complete arrest; (2) reduction in the number of disease episodes and/or symptoms; (3) reduction in lesional size; (4) inhibition (i.e., reduction, slowing down or complete stopping) of disease cell infiltration into adjacent peripheral organs and/or tissues; (5) inhibition (i.e. reduction, slowing down or complete stopping) of disease spread; (6) increase in host immune surveillance that results in regression or ablation of the disease lesion; (7) relief, to some extent, of one or more symptoms associated with the disorder; (8) increase in the length of disease-free presentation following treatment; and/or (9) decreased mortality at a given point of time following treatment. When a patient response is elicited, the antibody construct and/or the formulation of which it is a part are being used/administered to achieve a clinically beneficial outcome.

An "individual," "patient," or "subject" is a mammal. Mammals include, but are not limited to, domesticated animals (e.g., cows, sheep, cats, dogs, pigs, and horses), primates (e.g., humans and non-human primates such as monkeys), rabbits, and rodents (e.g., mice and rats). In certain embodiments, the individual, patient, or subject is a human.

Binding Assays and Other Assays: In some embodiments, an antibody construct provided herein is tested for its antigen binding activity, e.g., by known methods such as ELISA or Western blotting.

In some embodiments, competition assays may be used to identify an antibody that competes with an anti-integrin alpha-V, anti-integrin α5 antibody construct as described herein for binding to the respective integrins. In some embodiments, competition assays may be used to identify an antibody that competes with a bispecific antibody construct described herein for binding to integrin alpha-V and integrin α5. In certain embodiments, such a competing antibody binds to one of the same epitopes (e.g., linear or conformational epitopes) bound by an antibody construct described herein. Detailed exemplary methods for mapping an epitope to which an antibody binds are provided in Morris (1996) "Epitope Mapping Protocols," in Methods in Molecular Biology vol. 66 (Humana Press, Totowa, N.J.).

In an exemplary competition assay, immobilized integrin alpha-V is incubated in a solution comprising a first labeled antibody that binds to integrin alpha-V (e.g., a bispecific antibody construct described herein) and a second unlabeled antibody that is being tested for its ability to compete with the first antibody for binding to integrin alpha-V. The second antibody may be present in a hybridoma supernatant or may be purified. As a control, immobilized integrin alpha-V is incubated in a solution comprising the first labeled antibody but not the second unlabeled antibody. After incubation under conditions permissive for binding of the first antibody to integrin alpha-V, excess unbound antibody is removed, and the amount of label associated with immobilized integrin alpha-V is measured. If the amount of label associated with immobilized integrin alpha-V is substantially reduced in the test sample relative to the control sample, then that indicates that the second antibody is competing with the first antibody for binding to integrin alpha-V. See Harlow and Lane (1988) Antibodies: A Laboratory Manual ch. 14 (Cold Spring Harbor Laboratory, Cold Spring Harbor, N.Y.).

In a further exemplary competition assay, immobilized integrin α5 is incubated in a solution comprising a first labeled antibody that binds to integrin α5 and a second unlabeled antibody that is being tested for its ability to compete with the first antibody for binding to integrin α5. The second antibody may be present in a hybridoma supernatant or may be purified. As a control, immobilized integrin α5 is incubated in a solution comprising the first labeled antibody but not the second unlabeled antibody. After incubation under conditions permissive for binding of the first antibody to integrin α5, excess unbound antibody is removed, and the amount of label associated with immobilized integrin α5 is measured. If the amount of label associated with immobilized integrin α5 is substantially reduced in the test sample relative to the control sample, then that indicates that the second antibody is competing with the first antibody for binding to integrin α5.

A number of anti-integrin antibodies with specificity for α5, α5β1, or aV are known in the art. Some of these are described in the tables below. CDRs or variable domains or entire heavy/light chains from any prior art anti-α5 or α5β1 or β1 antibody, or from any newly generated anti-α5 or α5β1 or β1 antibody, could substitute for the anti-α5β1 antibody sequences utilized in the embodiment described in the Examples section. Likewise, CDRs or variable domains or entire heavy/light chains from any prior art anti-αV or αVβ3 antibody, or from any newly generated anti-αV or αVβ3 antibody, could substitute for the aV antibody sequences utilized in the embodiment described in the Examples section.

TABLE 1

Anti-AV, anti-AVB3, anti-A5, and anti-A5B1 Antibodies

| Antigen Specificity | Sequence, Deposit Number, or Other Information | Citation |
|---|---|---|
| A5B1 | a VL domain comprising a CDR-L1 comprising TL-S/T-S/P/T-Q/N-H-F/S-T/I-Y-K/T-I-G/D/S (SEQ ID NO: 65); a CDR-L2 comprising L/I-N/T-S-D/H/S-G/S-S/L/T-H/Y-N/K/Q/I-K/T-G/A-D/S/V (SEQ ID NO: 66); a CDR-L3 comprising G/A-S/A/Y-S/Y-S/A/Y-S/Y/T-GY-V/I (SEQ ID NO: 67); and a VH domain comprising a CDR-H1 comprising GFTFS-N/A-RW-I/V-Y (SEQ ID NO: 68); a CDR-H2 comprising (GIKTKP-N/A/T-I/R-YAT-E/Q-YADSVKG (SEQ ID NO: 69); and a CDR-H3 comprising L/V-TG-M/K-R/K-YFDY (SEQ ID NO: 70). | U.S. Pat. No. 8962275 |
| A5B1 | VL domain comprises a CDR-L1 comprising TLSSQHSTYTI (SEQ ID NO: 71); a CDR-L2 comprising LNSDSSHNKGSGIPD (SEQ ID NO: 72); a CDR-L3 comprising AAYYAYGYV (SEQ ID NO: 73); and a VH domain comprises a CDR-H1 comprising GFTFSARWIY (SEQ ID NO: 74); a CDR-H2 comprising GIKTKPAIYATEYADSVKGRFT (SEQ ID NO: 75); and a CDR-H3 comprising LTGMKYFDY (SEQ ID NO: 76). | U.S. Pat. No. 8962275 |
| A5B1 | Hybridoma Alpha5/beta1 7H5.4.2.8 (ATCC No. PTA-7421) | U.S. Pat. No. 8350010B2 |
| A5B1 | Hybridoma Alpha5/beta1 7H12.5.1.4 (ATCC No. PTA-7420) | U.S. Pat. No. 8350010B2 |
| A5B1 | Prepared against KLH conjugated synthetic mixed peptides 915-948/1048AA (human Integrin α5)+ 21-70/798AA (human Integrin (β1); reacts with human, mouse, rat | World Wide Web biorbyt.com/ integrin-alpha-5-beta-1-antibody |

TABLE 1-continued

Anti-AV, anti-AVB3, anti-A5, and anti-A5B1 Antibodies

| Antigen Specificity | Sequence, Deposit Number, or Other Information | Citation |
|---|---|---|
| a5b1 | MOR04624<br>VLK<br>diqmtqspsslsasvgdrvtitcrasqgissnlnwyqqkpgkapklliyaa<br>snlqsgpsrfsgsgsgtdftltisslq<br>pedfavyycqqysdqsytfgqgtkveikrt (SEQ ID NO: 77)<br>VH<br>qvqlvesgggIvqpggslrlscaasgftfssygmswvrqapgkglewvs<br>sisysdsntyyadsvkgrftisrdns<br>kntlylqmnslraedtavyycarglgdyghhhglsgifdywgqgtlvtvss<br>(SEQ ID NO: 78)<br>MOR04055<br>VLλ3<br>dieltqppsvsvapgqtariscsgdsigeqyahwyqqkpgqapvlviydd<br>nkrpsgiperfsgsnsgntatltis<br>gtqaededadyycgsytltntasvfgggtkltvlg (SEQ ID NO: 79)<br>VH3<br>qvqlvesgggIvqpggslrlscaasgftfsnyananwvrqapgkglewvs<br>risysgsdtyyadsvkgrftisrdnskntlylqmnslraedtavyycarege<br>fgfmystlvfdswgqgtLvtvss (SEQ ID NO: 80)<br>MOR04971<br>VLλ3<br>dieltqppsvsvapgqtariscsgdsigeqyahwyqqkpgqapvlviydd<br>nkrpsgiperfsgsnsgntatltis<br>gtqaededadyycssytyssdasvfgggtkltvlg (SEQ ID NO: 81)<br>VH3<br>qvqlvesgggIvqpggslrlscaasgftfsnyananwvrqapgkglewvs<br>aihdnghtyypdsvkgrftisrdnskntlylqmnslraedtavyycarege<br>fgfmystlvfdswgqgtlvtvss (SEQ ID NO: 82)<br>MOR04974<br>VLK<br>diqmtqspsslsasvgdrvtitcrasqgissnlnwyqqkpgkapklliyaa<br>snlqsgpsrfsgsgsgtdftltisslq<br>pedfatyycqqyasprqtfgqgtkveikrt<br>(SEQ ID NO: 83)<br>VH<br>qvqlvesgggIvqpggslrlscaasgftfssygmswvrqapgkglewvs<br>girakqsgyatdyaapvkgrftisrdnskntlylqmnslraedtavyycarg<br>lgdyghhhglsgifdywgqgtlvtvss (SEQ ID NO: 84)<br>MOR04975<br>VLK<br>diqmtqspsslsasvgdrvtitcrasqgissnlnwyqqkpgkapklliyaa<br>snlqsgpsrfsgsgsgtdftltisslq<br>pedfatyycqqyefgiqtfgqgtkveikrt<br>(SEQ ID NO: 85)<br>VH<br>qvqlvesgggIvqpggslrlscaasgftfssygmswvrqapgkglewvs<br>girakqsgyatdyaapvkgrftisrdnskntlylqmnslraedtavyycarg<br>lgdyghhhglsgifdywgqgtlvtvss (SEQ ID NO: 86)<br>MOR04977<br>VLK<br>diqmtqspsslsasvgdrvtitcrasqgissnlnwyqqkpgkapklliyaa<br>snlqsgpsrfsgsgsgtdftltisslq<br>pedfatyycqqyssnpqtfgqgtkveikrt (SEQ ID NO: 87)<br>VH<br>qvqlvesgggIvqpggslrlscaasgftfssygmswvrqapgkglewvsf<br>iepkwrggathyaasvkgrftisrdnskntlylqmnslraedtavyycargl<br>gdyghhhglsgifdywgqgtlvtvss (SEQ ID NO: 88)<br>MOR04985<br>VLK<br>diqmtqspsslsasvgdrvtitcrasqgissnlnwyqqkpgkapklliyaa<br>snlqsgpsrfsgsgsgtdftltisslq<br>pedfavyycqqysdqsytfgqgtkveikrt<br>(SEQ ID NO: 89)<br>VH<br>qvqlvesgggIvqpggslrlscaasgftfssygmswvrqapgkglewvs<br>girakqsgyatdyaapvkgrftisrdnskntlylqmnslraedtavyycarg<br>lgdyghhhglsgifdywgqgtlvtvss (SEQ ID NO: 90) | WO2007134876A2 |
| BETA 1 | IgG; specific for mouse, rat, human beta 1 | CN104994874B<br>EP2938359A1 |
| Av | hybridoma line 271-14D9.F8, IgG1, kappa | Mitjans et al., J. Cell Science 108:2825-2838 (1995) |

TABLE 1-continued

Anti-AV, anti-AVB3, anti-A5, and anti-A5B1 Antibodies

| Antigen Specificity | Sequence, Deposit Number, or Other Information | Citation |
|---|---|---|
| Av | hybridoma line 271-20A9; IgG1, kappa | Mitjans et al., J. Cell Science 108:2825-2838 (1995) |
| Av | hybridoma line 271-23G5; IgG1, kappa | Mitjans et al., J. Cell Science 108:2825-2838 (1995) |
| Av | Immunogen Clone EPR 16800; IgG; Binds to recombinant fragment within Human Integrin alpha V aa 1-250; also mouse and rat | World Wide Web abcam.com/ integrin-alpha-v-antibody-epr16800-ab179475.html |
| AvB3 | 5 avB3-binding monoclonal abs (17E6, 10C4, 23C6, LM609, 69-6-5) were shown to bind to epitopes in the B-propeller domain (ligand binding). 4 are shown to bind the thigh domain (AMF7, M9, P2W7, P3G8). | Kamata et al., PLoS One 8(6): e66096 (2013) |

TABLE 2

Commercial Antibodies

| Antigen | Supplier | Species specificity | Isotype | Source |
|---|---|---|---|---|
| α5 | Sigma | Human | IgG2b | World Wide Web sigmaaldrich.com/catalog/product/mm/CBL497?lang=en&region=US&utm_medium=referral&utm_source=biocompare1&utm_campaign=biocompare_2017 |
| α5 | LifeSpan Biosciences | Human | IgG3 | World Wide Web lsbio.com/antibodies/anti-itga5-antibody-integrin-alpha-5-antibody-cd49e-antibody-wb-western-ls-c13705/14446?trid=247 |
| α5 | Sigma | Human | IgG3 | World Wide Web sigmaaldrich.com/catalog/product/mm/MAB1956Z?utm_source=biocompare1&utm_campaign=biocompare_2017&utm_medium=referral%C2%A0%20%C2%A0%C2%A0 |
| α5 | LifeSpan Biosciences | Human | IgG2b | World Wide Web lsbio.com/antibodies/anti-itga5-antibody-integrin-alpha-5-antibody-cd49e-antibody-flow-if-immunofluorescence-ls-c13678/14419?trid=247 |
| α5 | R&D | Human | IgG1 | World Wide Web rndsystems.com/products/human-integrin-alpha5-cd49e-antibody-238307_mab1864?utm_source=biocompare&utm_medium=referral&utm_campaign=product&utm_term=primaryantibodies |
| α5 | OriGene | Human | IgG2b | World Wide Web origene.com/catalog/antibodies/primary-antibodies/am32340pu-n/integrin-alpha-5-itga5-mouse-monoclonal-antibody-clone-id-clb-705 |

TABLE 2-continued

Commercial Antibodies

| Antigen | Supplier | Species specificity | Isotype | Source |
|---|---|---|---|---|
| α5β1 | Boster | Human, Mouse, Rat | | World Wide Web bosterbio.com/anti-integrin-alpha-5-picoband-trade-antibody-pb9254-boster.html?utm_source=listing%3Abiocompare&utm_medium=paid%2Blisting %2Bppc&utm_campaign=product %2Blist %3A#details |
| α5β1 | Sigma | Human | IgG3 | World Wide Web sigmaaldrich.com/catalog/product/mm/MAB2514?lang=en&region=US&utm_medium=referral%A0%20%A0%A0&utm_source=biocompare1&utm_campaign=biocompare2017 |
| α5β1 | Sigma | Human | IgG1 | World Wide Web sigmaaldrich.com/catalog/product/mm/MAB1969?lang=en&region=US&utm_medium=referral%A0%20%A0%A0&utm_source=biocompare1&utm_campaign=biocompare_2017 |
| α5β1 | Sigma | Human, Rat | IgG2c | World Wide Web sigmaaldrich.com/catalog/product/mm/MAB2575?lang=en&region=US&utm_medium=referral %A0%20%A0%A0&utm_source=biocompare1&utm_campaign=biocompare_2017 |
| α5β1 | Enzo Life Sciences | Human | IgG4k | World Wide Web enzolifesciences.com/product.php?pid=ENZ-ABS385 |
| α5β1 | Ab Online | Human, Monkey | IgG | World Wide Web antibodies-online.com/antibody/228615/anti-Integrin+alpha+5+beta+1+antibody/?utm_source=partner&utm_medium=biocompare&utm_campaign=non_sponsored&utm_content=primary_oem&utm_term=ABIN228615 |
| α5β1 | BD Biosciences | Human, Pig | IgG1 Kappa | World Wide Web bdbiosciences.com/us/p/555650?utm_source=biocompare&utm_medium=catalog&utm_campaign=biocomparecat |
| αv | Millipore Sigma | Human | IgG1 kappa | World Wide Web sigmaaldrich.com/catalog/product/mm/MABT207?lang=en&region=US&utm_medium=referral %A0%20%A0%A0&utm_source=biocompare1&utm_campaign=biocompare_2017 |
| αv | LifeSpan Biosciences | Human | IgG1 | World Wide Web lsbio.com/antibodies/anti-itgav-antibody-integrin-alpha-v-antibody-cd51-antibody-flow-wb-western-ls-c13739/14480?trid=247 |
| αv | Abcam | Human | IgG1 | World Wide Web abcam.com/Integrin-alpha-V-antibody-23C6-Low-endotoxin-Azide-free-ab185741.html?utm_source=biocompare&utm_medium=paid_referral&utm_term=1ry_3311_185741&utm_campaign=editorial |
| αv | OriGene | Human | IgG2a | World Wide Web origene.com/catalog/antibodies/primary-antibodies/am32337pu-n/cd51-itgav-mouse-monoclonal-antibody-clone-id-nki-m9-former-paf2a |

TABLE 2-continued

Commercial Antibodies

| Antigen | Supplier | Species specificity | Isotype | Source |
|---|---|---|---|---|
| αv | STEMCELL Technologies | Human | IgG2a kappa | World Wide Web stemcell.com/products/anti-human-cd51-antibody-clone-nki-m9.html |
| αv | Enzo Life Sciences | Human | IgG1 | World Wide Web enzolifesciences.com/product.php?pid=ALX-803-304 |

The invention will be further illustrated with the following non-limiting examples. These examples disclose, among other things, that a bispecific antibody construct that simultaneously binds and inhibits integrin alpha-V and integrin α5β1 is more efficacious than a pair of distinct antibodies, one of which targets the alpha-V integrin and the other of which targets the α5β1 integrin.

EXAMPLES

Example 1

A prototype bispecific, tetravalent antibody construct designated "ITGA5B1xAV" was designed with the format shown in FIG. 10, and was prepared by standard recombinant methods. The Fab portion was designed based on the variable domains of Abituzumab, and the scFv was designed based on the variable domains of Volociximab. Genes encoding the two amino acid sequences shown in FIG. 12A (heavy chain plus scFv) and FIG. 12B (light chain) were prepared and cloned into the expression vector via HindIII/NotI. Two plasmids were isolated and subjected to transient expression with 293 cells as the host. The supernatant was collected and the antibody purified using a protein A affinity column.

The bispecific antibody demonstrated enhanced potency in a range of cancer cell adhesion and migration assays. In addition, in the C4-2b prostate cancer line, the bispecific antibody construct reduced cell viability more potently than the monospecific antibodies alone and induced effects equivalent to those induced by the combination of the two monospecific antibodies, but did so at one-fifth the dose of the combination. In studies of endothelial cell migration induced by tumor-stromal cell interactions, the bispecific antibody is particularly potent in blocking endothelial cell migration and is superior to bevacizumab. Taken together, the below data indicate that this novel bispecific antibody has unique and potentbiological activity in a range of experimental cancer systems.

Other Antibodies: Other antibodies were sourced as follows: monoclonal α5, alpha-V (Millipore MAB1956Z and MABT207), heterodimeric α5b1: (Alpha5/beta1 7H5.4.2.8 hybridoma (ATCC No. PTA-7421)).

Cell migration assay: Cell migration assays were performed using a Boyden Chamber set up. A 24-well assay plate was prepared by adding 800 μL of chemoattractant underneath uncoated 8-micron pore transwell inserts (Corning 353097) and heated to 37° C. 25,000 cells (harvested in log-phase growth) were added from a homogenous cell suspension to the top of the well to a total volume of 200 pt. The assay was stopped after 24 hours at 37° C. by removal and washing of the membrane inserts with PBS and formalin (Fischer Scientific SF100-4) fixation of the cells for 15 minutes. Following another 3× PBS wash, cells were removed from the tops of the membranes using cotton tip swabs and were stained using calcein AM (ThermoFisher C1430). After drying, membranes were mounted onto microscope slides and cell counts were performed on 3-5 representative fields of a membrane using a 10× or 20× objective.

Cell adhesion assay: A 96-well plate was plated with 50 μL of adherent substrate in triplicate and incubated at 37° C. for 1 hour. Non-specific binding sites were blocked by incubating the wells with 1% BSA for 30 minutes at 37° C. After washing the wells 3× with PBS, 10,000 cells were harvested in log-phase growth and incubated for 20 minutes on ice with the indicated dose of integrin-neutralizing antibody, added in 100 μL of serum-free culture media to each well from a homogenous cell suspension. The plate was incubated for 60-90 minutes at 37° C. to allow establishment of adherence profiles. To remove non-adherent cells, the wells were gently washed 5× with PBS. Adherent cell counts were assayed using Cell Counting Kit 8 (CCK-8) reagent (Bimake).

Endothelial cell migration assay: hBM-MSCs (human bone-marrow derived mesenchymal stromal cells) were cultured at confluence for 24 hours in a 24-well format. 20,000 cancer cells were seeded into the wells and co-cultured overnight. Then, an assay for cell migration towards the co-culture was performed as described above, using 10,000 HUVECs (human umbilical vein endothelial cells).

Cell viability assay: The effect of bispecific ITGA5V neutralization on cell viability was monitored by cell viability assay using Cell Counting Kit-8 (CCK-8) (Bimake) cell viability reagent. Briefly, cells were incubated with designated ITG antibody concentration and then seeded in a 96-well microtiter plate with replications. Cell viability was measured with GloMax-Multi Microplate Reader (Promega) quantitatively by recording the absorbance at 450 nm. Percent cell viability (%) was calculated and shown as a ratio of absorbance in ITG antibody treated cells to absorbance in IgG control cells after subtracting the average absorbance of background.

Flow Cytometry: Cells with variable membrane integrin α5 and alpha-V expression were incubated with monoclonal α5 or alpha-V antibodies (Millipore MAB1956Z and MABT207), the bispecific antibody construct ITGA5B1xAV, or isotype control, for 1 hour at room temperature followed by 1 hour of incubation with a secondary-conjugated antibody, before being analyzed by flow cytometry.

Statistics: The mean fluorescent intensities (MFI) for the α5, alpha-V, and bispecific ITGA5B1xAV stained cell populations for each cell line were calculated from the flow cytometry data. Then a correlation coefficient between the sum of α5 and alpha-V MFIs and the bispecific ITGA5B1xAV was calculated.

The results indicate that, although integrin α5 blockade is sufficient to abrogate migration in PC-3 prostate cancer cells, blockade of both integrin α5 and integrin alpha-V is required to abrogate migration in DU-145 prostate cancer cells. As shown in FIGS. 1A and 1B, there is heterogeneity in prostate cancer cell interactions with the hBM-MSC secretome. PC-3 (FIG. 1A) and DU-145 (FIG. 1B) prostate cancer cells were pre-treated with 50 μg/mL of the indicated integrin neutralizing antibody or a matched isotype control (Iso), and then tested in either a migration assay (movement across an 8 μm pore polypropylene membrane for 24 hours) or adhesion assay (1 hour) to hBM-MSC conditioned media (CM). The antibodies targeting α5 and β1 integrins inhibited migration and adhesion of PC-3 cells, while the other antibodies tested, including an antibody targeting alpha-V, had no statistically significant effect (FIG. 1A). With DU-145 cells, blocking both α5 integrin and alpha-V integrin was required to neutralize adhesion and migration (FIG. 1B).

Figure 2B:
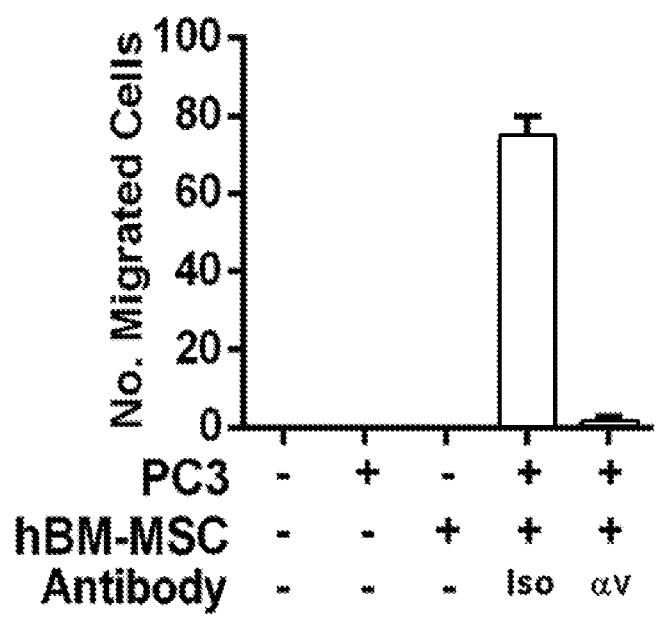

Endothelial cell migration is the earliest required phase of angiogenesis that can be studied in vitro. Using the endothelial cell migration assay described above, the role of α5 and alpha-V integrins in mediating these responses was studied in experiments with co-cultured PC-3 and hBM-MSCs. As shown in FIGS. 2A and 2B, the endothelial cells (HUVECs) exhibited a chemotactic response to PC-3-hBM-MSC co-cultures (see the fourth bar in each of FIGS. 2A and 2B) that was inhibited PC-3 α5 neutralization (FIG. 2A) or HUVEC alpha-V neutralization (FIG. 2B). Neutralization was performed by pre-treatment with 50 μg/mL of integrin neutralizing antibody or matched isotype control (Iso). Thus, endothelial cell migration induced by prostate cancer-hBM-MSC interaction is regulated by integrins α5 and alpha-V.

Figures 3A, 3B:
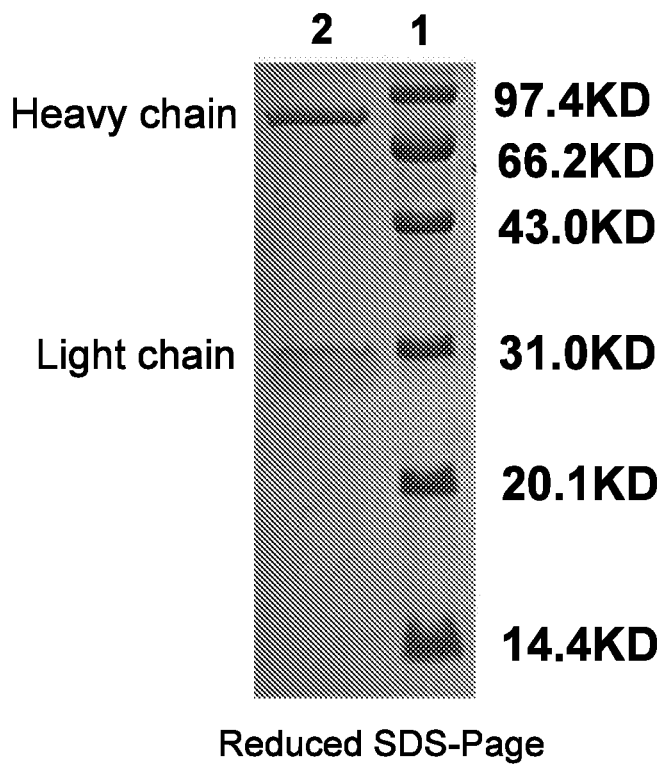
FIGS. 3A and 3B include data concerning the purity and binding of an ITGA5B1xAV bispecific antibody.

A bispecific antibody for α5β1 (obligate heterodimeric partners) and alpha-V (ITGA5B1xAV) was generated and its purity demonstrated by SDS-PAGE (FIG. 3A). To demonstrate binding specificity, flow cytometric binding studies were conducted with monoclonal α5, alpha-V, and bispecific ITGA5B1xAV across a panel of cell lines with variable integrin α5 and alpha-V expression density. The sum of integrin α5 and integrin alpha-V binding (MFI) was highly correlated with bispecific binding (correlation.9187; FIG. 3B).

Figure 4:
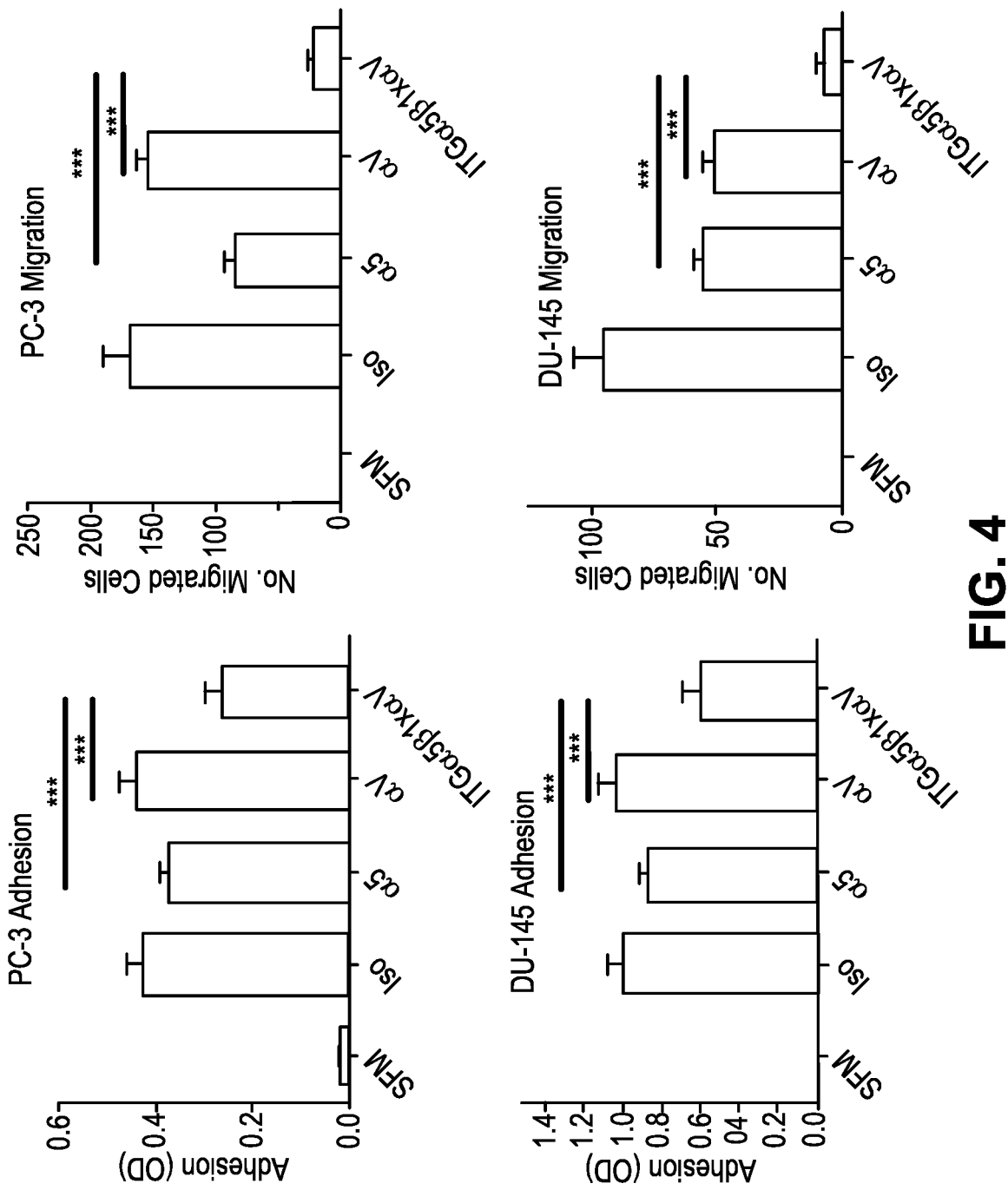
FIG. 4 is a panel of bar graphs mapping adherent and migrated PC-3 (top) and DU-145 cells (bottom) following antibody neutralization. Adhesion was assessed after one hour of co-culturing with hBM-MSC conditioned medium (CM) and migration was assessed after 24 hours. The α5 and alpha-V integrins were neutralized with 50 µg/ml of each of the indicated antibodies, and the bispecific antibody construct was found to be superior to either the anti-α5 or anti-alpha-V antibodies alone in inhibiting adhesion and migration. ***: $P \leq 0.001$. SFM=serum-free media. "Iso"=isotype control.
Figure 5:
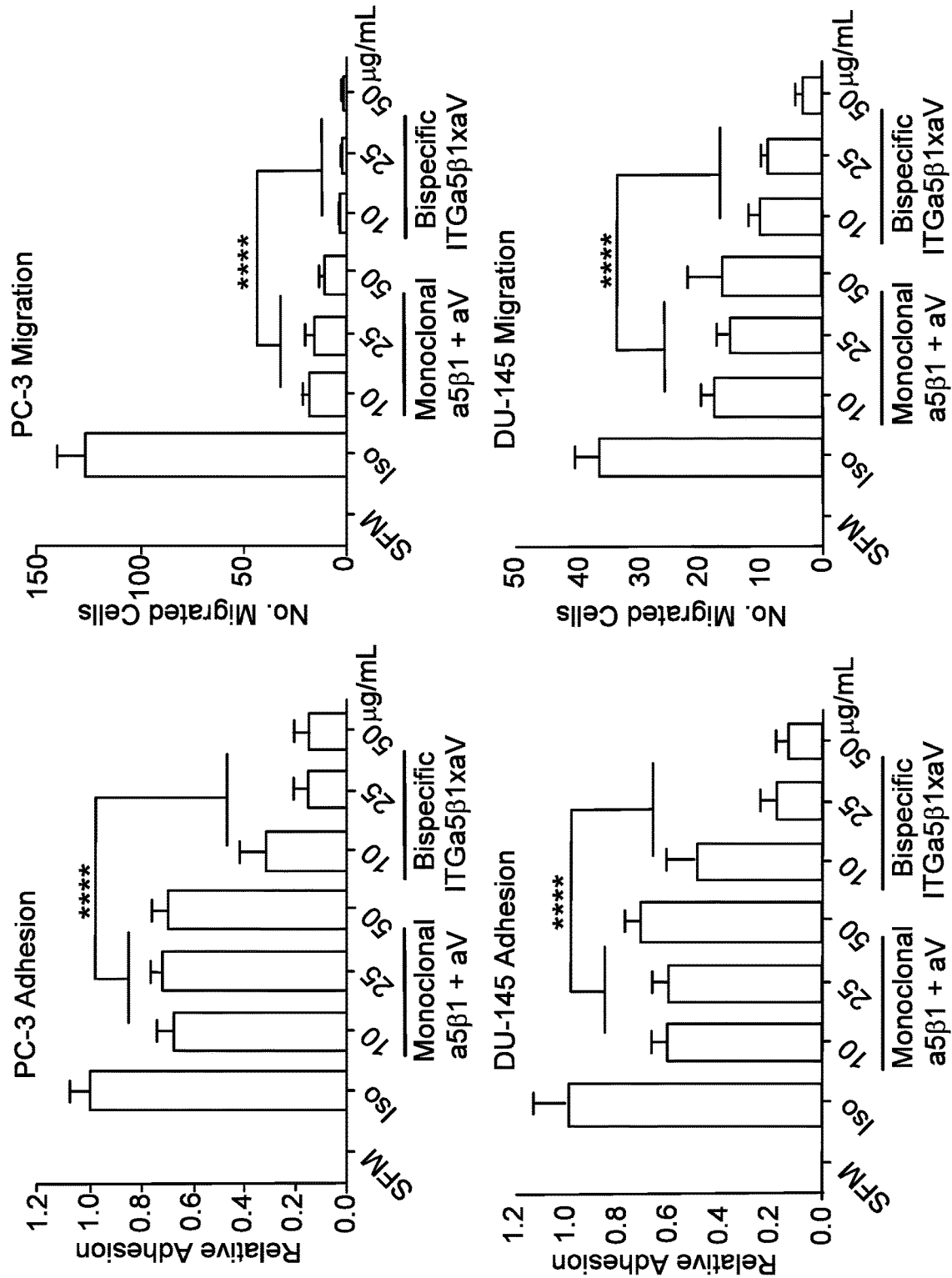
FIG. 5 is a panel of bar graphs displaying the results of migration and adhesion assays of prostate cancer cells (PC-3 cells, shown in the top two graphs and DU-145 cells, shown in the bottom two graphs). The integrins α5 and alpha-V were neutralized with the monoclonal and bispecific antibody constructs indicated. The bispecific antibody ITGa5β1xaV inhibited the adhesion and migration of both cell types more than the combined antibody treatment. The significance of the difference in the effect of the bispecific antibody compared to combination of monoclonal antibodies was calculated using one-way analysis of variance (ANOVA) with multiple comparisons between equivalent dose pairs amongst the two test groups. Significance shown is the p-value summary (GraphPad Prism). ****: $P \leq 0.0001$. SFM=serum-free medium. "Iso"=isotype control.

The bispecific antibody construct ITGA5B1xAV was found to be superior to either an integrin α5-neutralizing antibody or an integrin alpha-V neutralizing antibody in inhibiting prostate cancer cell adhesion and migration (see FIG. 4), and we have also found it to be superior to a combination (mixture) of integrin α5 and integrin alpha-V antibodies (see FIG. 5). See also FIGS. 6A and 6B, summarizing data showing that the bispecific antibody construct ITGA5B1xAV is superior to the combination of anti-integrin α5 and anti-integrin alpha-V antibodies in inhibiting endothelial cell migration in co-cultures of prostate cells and hBM-MSC cells.

Figure 7A:
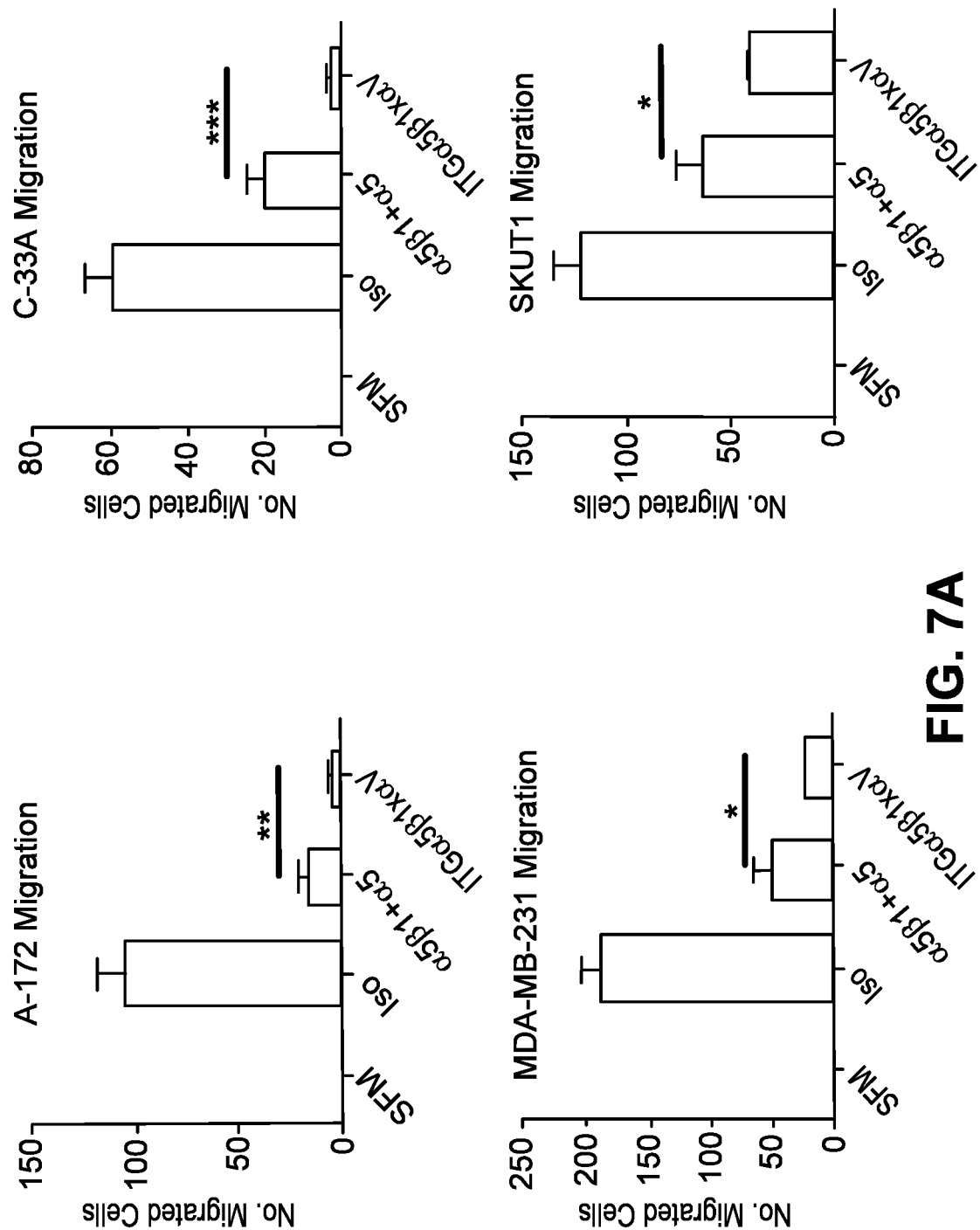
FIGS. 7A and 7B are a panel of bar graphs summarizing data from assays of non-prostate cancer cell migration (FIG. 7A; 24 hours) and adhesion (FIG. 7B; one hour) to hBM-MSC CM (conditioned medium). Neutralization was performed with 50 µg/mL of total antibody. The bispecific antibody construct was superior to the combination of anti-α5β1 and anti-alpha-V monoclonal antibodies at inhibiting migration and adhesion of a wide range of non-prostate cancer cells. * indicates $P \leq 0.05$. ** indicates $P \leq 0.01$. SFM=serum-free media. "Iso"=isotype control.
Figure 7B:
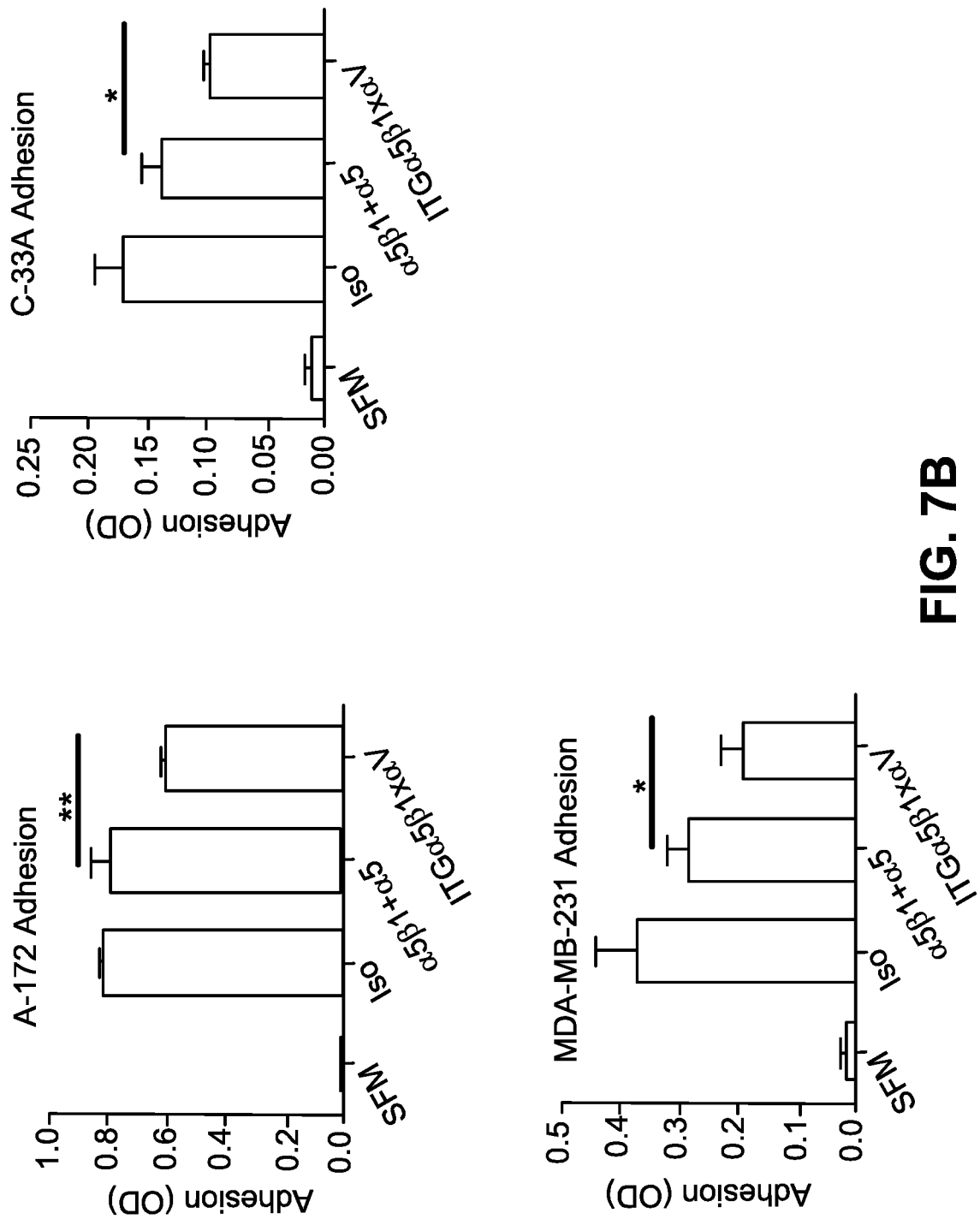

The bispecific antibody was also found to be superior to the combination of two monospecific antibodies that target the same integrins (aV and alpha-V) in neutralizing adhesion and migration in other cancer cell types, including the glioblastoma cell line A-172, the breast cancer cell line MDA-MB-2β1, the cervical cancer cell line C-33A, and the uterine cancer cell line SKUT1 (FIGS. 7A and 7B).

Figure 8A:
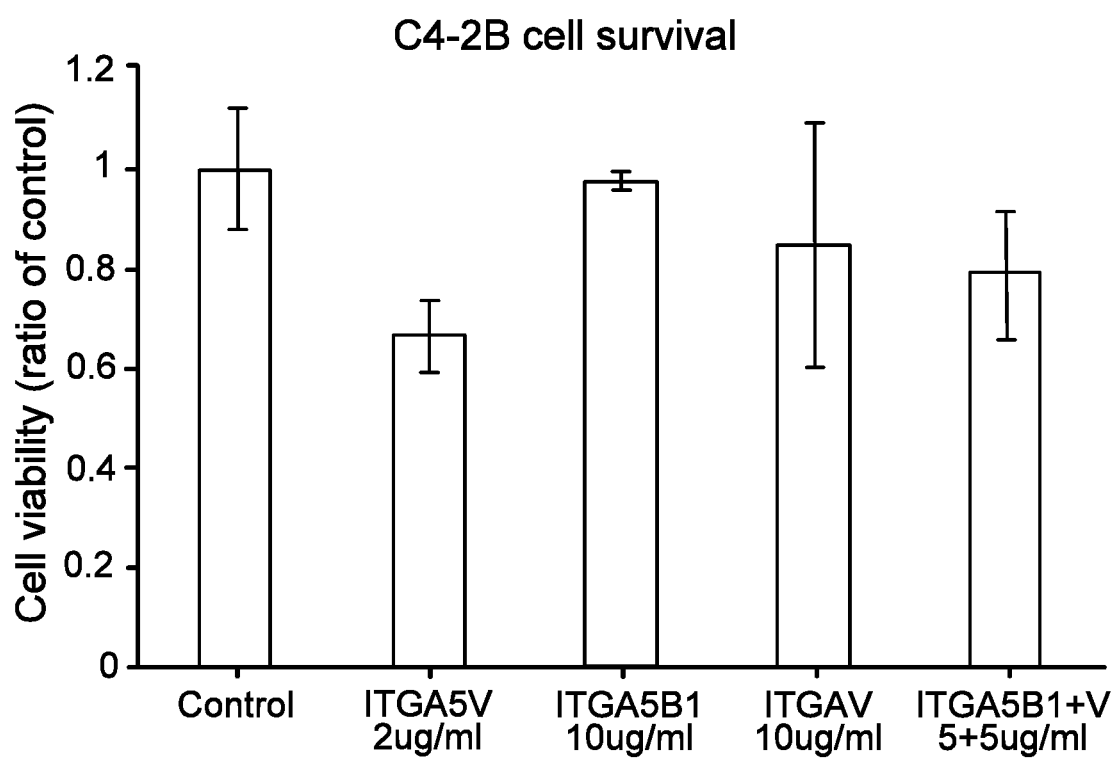
FIGS. 8A and 8B are a pair of bar graphs illustrating the results of an assay for cancer cell viability. The cells were exposed to the antibodies indicated, at the concentrations indicated. IgG is an isotype control; ITGA5 is an integrin α5 monospecific antibody; ITGB1 is an integrin beta 1 monospecific antibody; ITGB3 is an integrin beta 3 monospecific antibody; ITGAVB3 is an integrin alpha-V-beta 3 antibody.
Figure 8B:
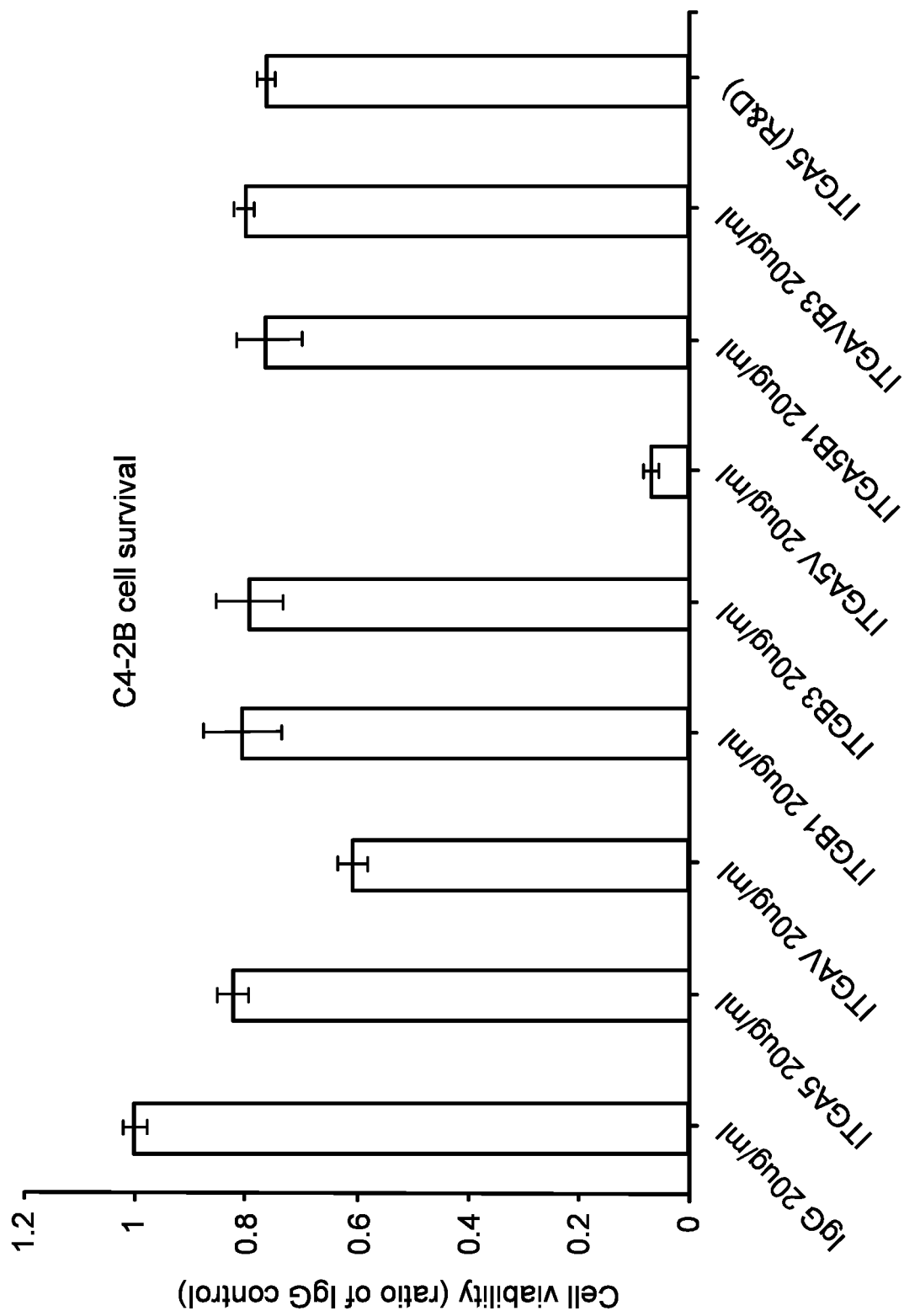

The bispecific antibody construct was more effective in inhibiting prostate cancer cell survival than either an anti-integrin α5 antibody, an anti-integrin alpha-V antibody, or those two monospecific antibodies used in combination. C4-2B cells were incubated with the bispecific antibody construct or with the anti-integrin α5 antibody and/or the anti-integrin alpha-V antibody, as indicated in FIGS. 8A and 8B. The antibodies were incubated with the cells at 4° C. for 30-60 minutes and were then seeded (in triplicate) into 96-well plates and maintained in a humidified 37° C. incubator with 5% $CO_2$ for 24-48 hours before performing the cell viability assay. The bispecific antibody construct was shown to be potent at one-fifth the concentration of the combination of monospecific antibodies targeting α5β1 and alpha-V integrin.

Figure 9:
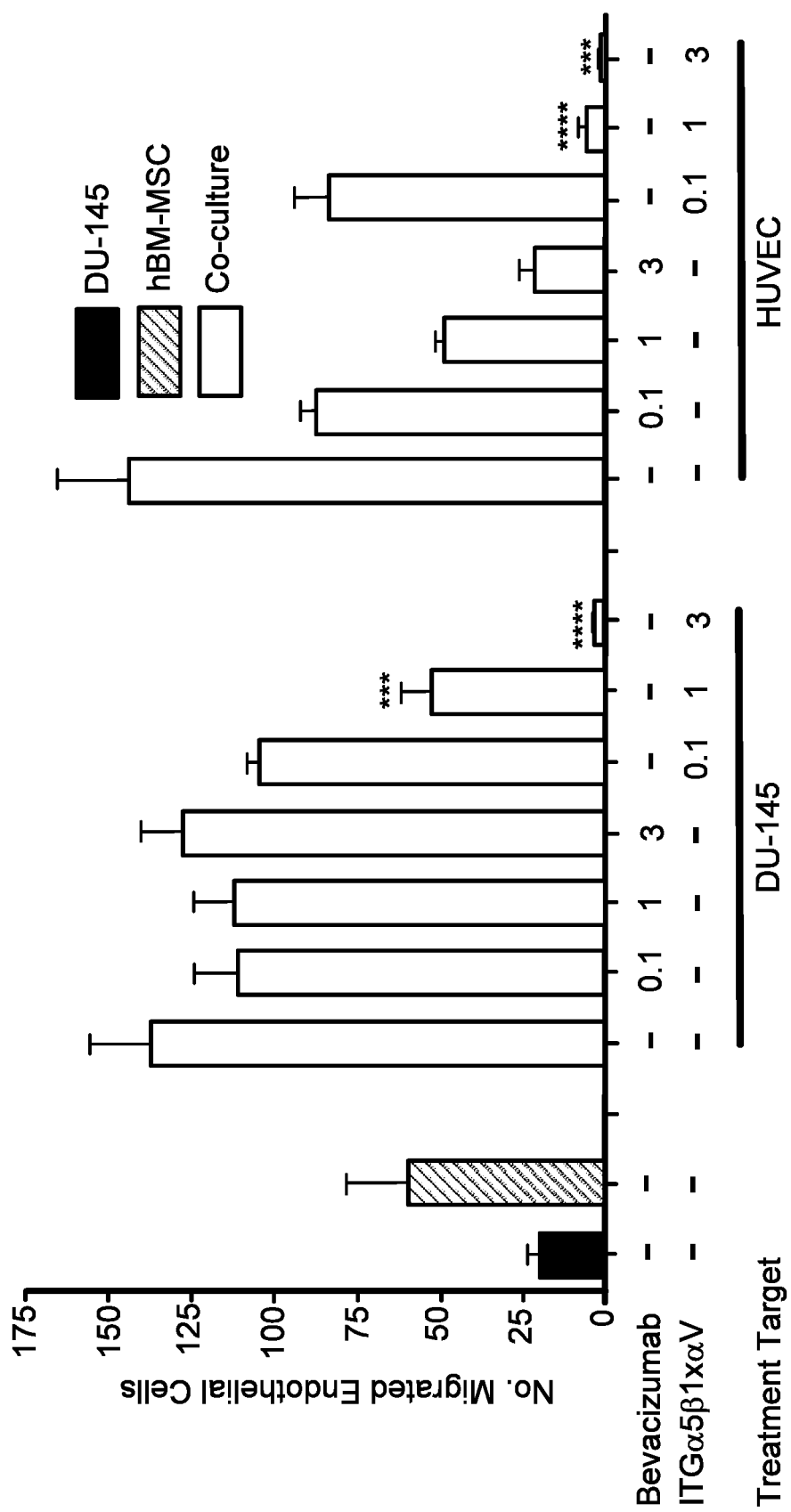
FIG. 9 is a bar graph showing the results of an assay in which HUVEC or DU-145 cells were treated with the indicated doses of bevacizumab or the bispecific antibody construct ITGA5B1xAV (doses in µg/mL) prior to assaying HUVEC migration to DU-145/hBM-MSC co-culture. Bispecific antibody treatment (1, 3 µg/mL) of either HUVEC or DU-145 was significantly more potent at reducing endothelial migration compared to bevacizumab. **: $P \leq 0.0001$, *: $P \leq 0.001$.

When the bispecific antibody construct was compared to bevacizumab, an antibody that targets VEGF, it was found that the bispecific antibody construct was superior to bevacizumab in inhibiting endothelial cell migration to prostate-cancer-hBM-MSC co-culture (FIG. 9). HUVEC or DU-145 cells were treated with the doses of the antibodies indicated in FIG. 9 prior to assaying HUVEC migration to DU145/hBM-MSC.

Example 2

The ability of the bispecific antibody ITGA5B1xAV to block adhesion, migration, cell survival and induction of endothelial migration in co-culture with stromal cells was compared to the ability of monospecific antibodies targeting α5 integrin (or its obligate α5β1 heterodimer) or integrin alpha v (or the αvβ3 heterodimer), both alone and in combination, to block those functions, using α5/αv co-expressing cells from diverse tumor types including prostate, breast, glioma, cervix, and uterine cancer.

Results: While combined α5 and αv neutralization with dual monospecific antibodies was superior to individual single agents in blocking adhesion, migration, and induction of endothelial chemotaxis across diverse tumor types that co-expressed α5 and αv integrins, the bispecific antibody ITGA5B1xAV was significantly superior to the combined monospecific antibodies in these assays (FIGS. 7A and 7B). In addition, a significant reduction in cell survival was noted in selected tumor types with ITGA5B1xAV (FIGS. 8A and 8B). Strikingly, ITGA5B1xAV was significantly more potent than bevacizumab in the inhibition of endothelial migration induced by tumor-stromal cell interactions (FIG. 9).

Targeting tumor, stromal and endothelial cells simultaneously with ITGA5B1xAV represents a potentially effective therapeutic strategy for targeting diverse mechanisms of progressive disease in the tumor microenvironment.

Example 3

The mechanism of action of the ITGA5B1xAV antibody was further explored by assessing the comparative fates of integrins on various cell types in vitro following treatment with the ITGA5B1xAV antibody, one of the individual monospecific antibodies, or a combination of the two monospecific antibodies.

Figure 15A:
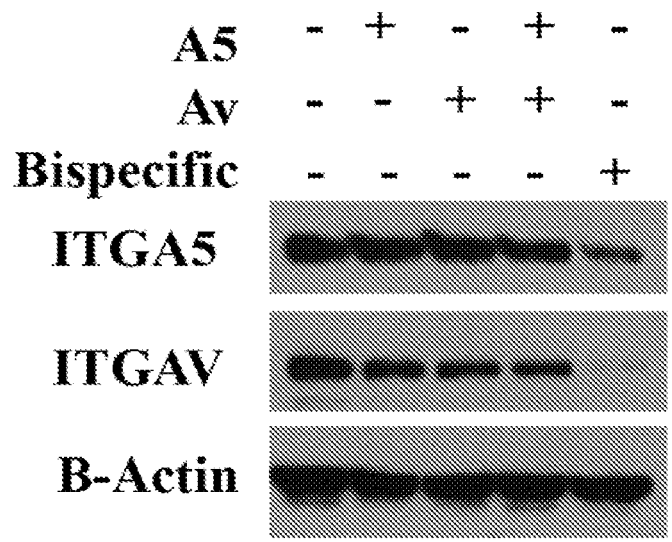
FIG. 15A is a Western blot showing the effect of antibody treatment on expression of three proteins in PC-3 cancer cells.
Figure 15B:
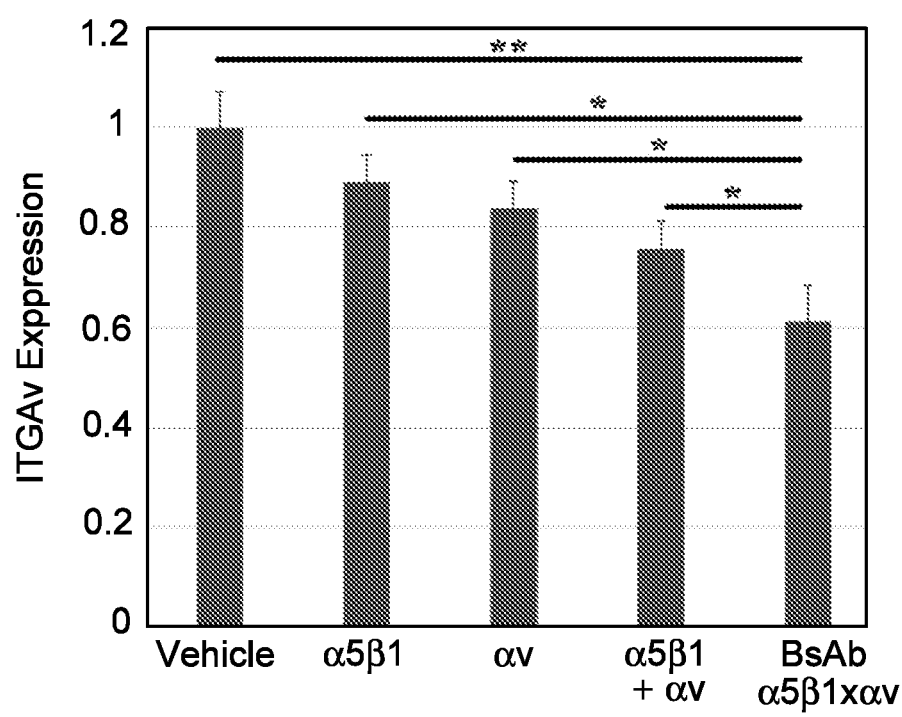
FIG. 15B is a bar graph quantifying the level of integrin av expression in PC-3 cancer cells after antibody treatment, normalized to vehicle.

PC-3 cells were treated with 10 μg/mL of a monospecific antibody, a combination of the monospecific antibodies, or ITGA5B1xAV for 20 minutes on ice before being seeded into 6-well plates. 48 h later, cells were harvested for Western blot or flow cytometry. FIG. 15A shows that treatment of PC-3 cancer cells with ITGA5B1xAV bispecific antibody construct results in stronger depletion of the target integrins compared to control antibodies, even in combination. Maximal reduction of AV expression by ITGA5B1xAV was confirmed by flow cytometry, with the quantification of the latter experiment shown in FIG. 15B.

Figure 16A:
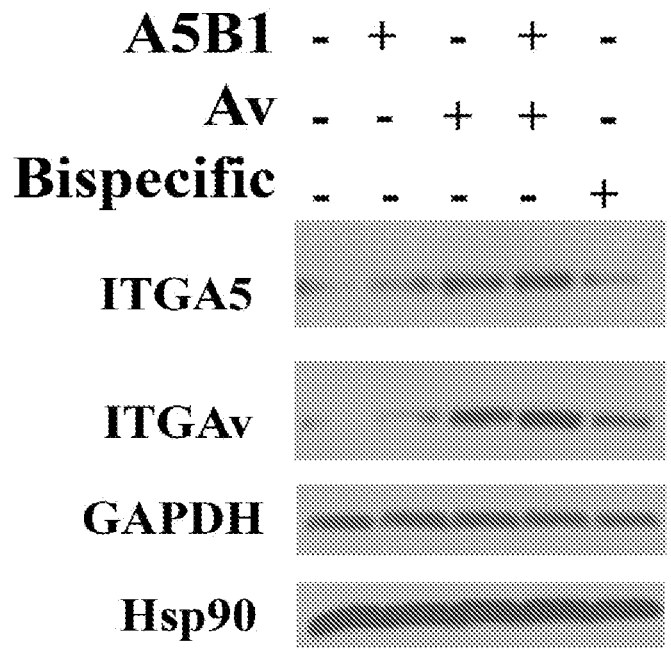
FIGS. 16A and 16B are Western blots showing the effect of antibody treatment on expression of four proteins in DU-145 and VCAP cancer cells.
Figure 16B:
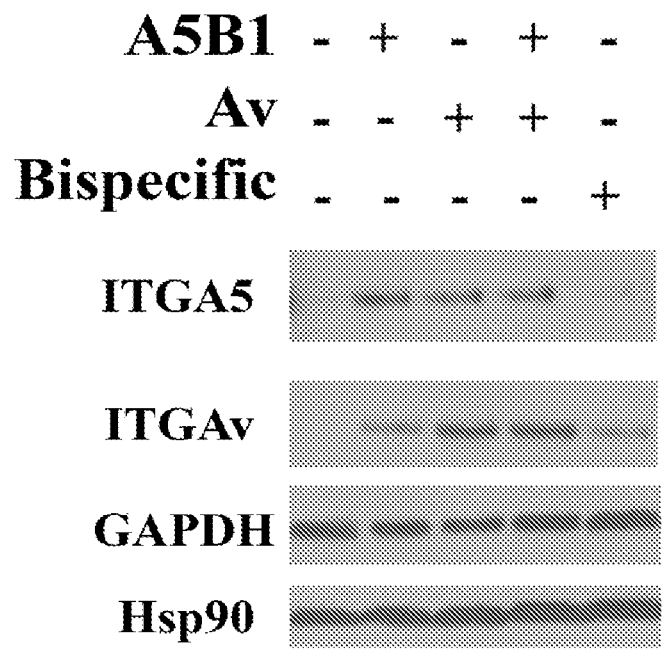

DU-145 and VCAP cancer cells were treated with 10 μg/mL of a monospecific antibody, a combination of the monospecific antibodies, or ITGA5B1xAV for 20 minutes on ice before being seeded into 6-well plates. 48 h later, cells were harvested for Western blot. In both DU-145 and VCAP cell types, a strong adaptive upregulation of one or both integrins is seen with monospecific antibodies alone and in combination; this upregulation is strongly mitigated with ITGA5B1xAV treatment (FIGS. 16A and 16B).

Figures 17A, 17B:
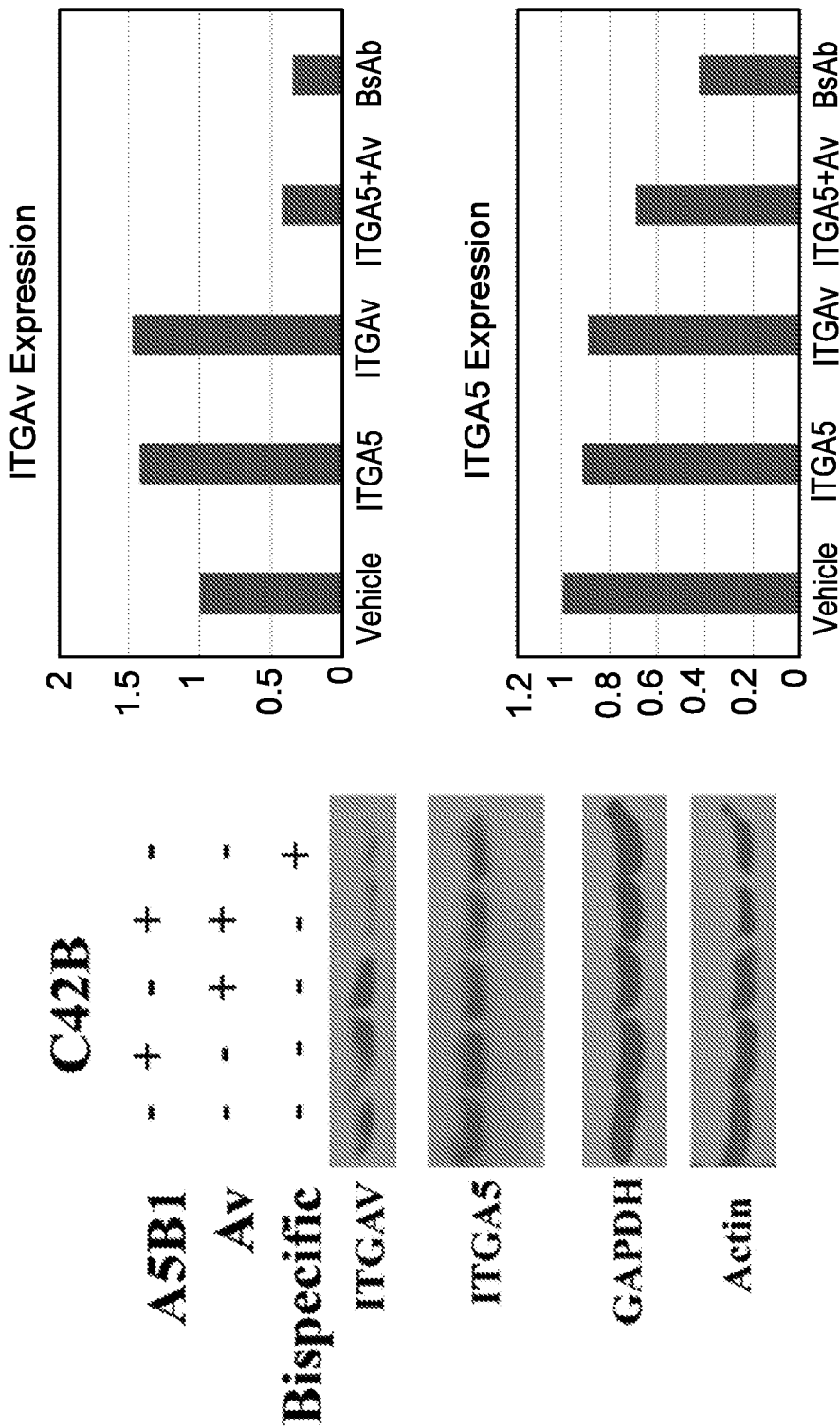
FIG. 17A is a Western blot showing the effect of antibody treatment on expression of four proteins in C42B cancer cells.
FIG. 17B is pair of bar graphs showing the effect of antibody treatment on relative expression of integrin αv and α5 in C42B cells.

C42B cancer cells were treated with 10 μg/mL of a monospecific antibody, a combination of the monospecific antibodies, or ITGA5B1xAV for 20 minutes on ice before being seeded into 6-well plates. 48 h later, cells were harvested for Western blot. In C42B cells, ITGA5B1xAV treatment maximally induces loss of integrin α5 expression and mitigates compensatory integrin aV upregulation (FIGS. 17A and 17B).

Figure 18A:
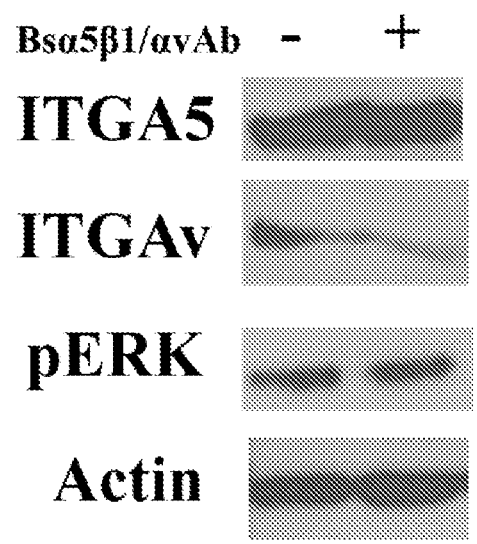
FIGS. 18A and 18B are Western blots showing the effect of antibody treatment on expression of various proteins in HUVEC endothelial cells.
Figure 18B:
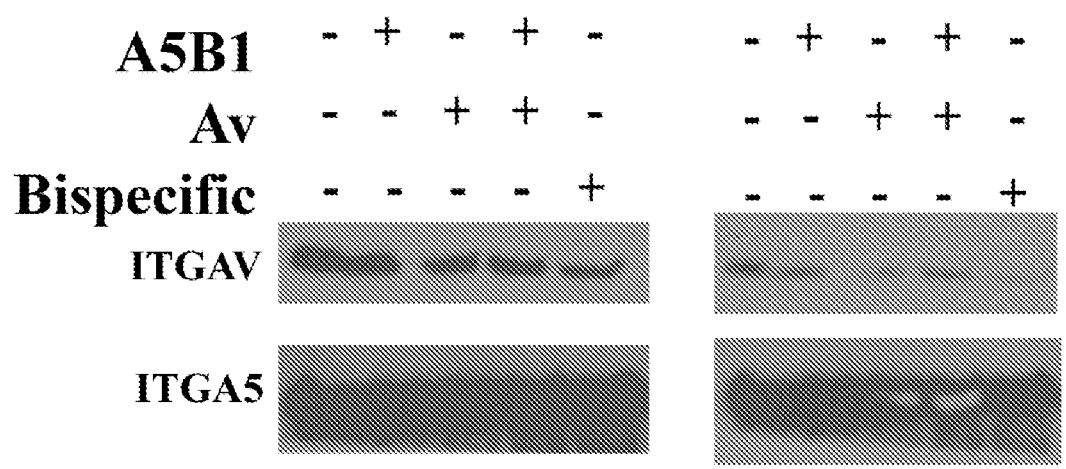

HUVEC endothelial cells were treated with or without 10 μg/mL of ITGA5B1xAV (FIG. 18A), or with 10 μg/mL of a monospecific antibody, a combination of the monospecific antibodies, or ITGA5B1xAV (FIG. 18B), for 20 minutes on ice before being seeded into 6-well plates. 48 h later, cells were harvested for Western blot. The data in FIGS. 18A and 18B show that, in HUVEC endothelial cells, ITGA5B1xAV treatment has specific and potent impact on integrin αv (and not integrin α5) depletion compared to monospecific and combination antibody therapy. These data suggest a mechanism of action relevant to control of pathological angiogenesis, in which integrin αv is known to play an important role in cooperation with integrin α5. These data are consistent with the experiments described above showing the superior potency and efficacy of ITGA5B1xAV on endothelial migration induced by tumor-stromal interactions, compared to monospecific and combination anti-integrin antibody blockade and to bevacizumab therapy.

Figure 19:
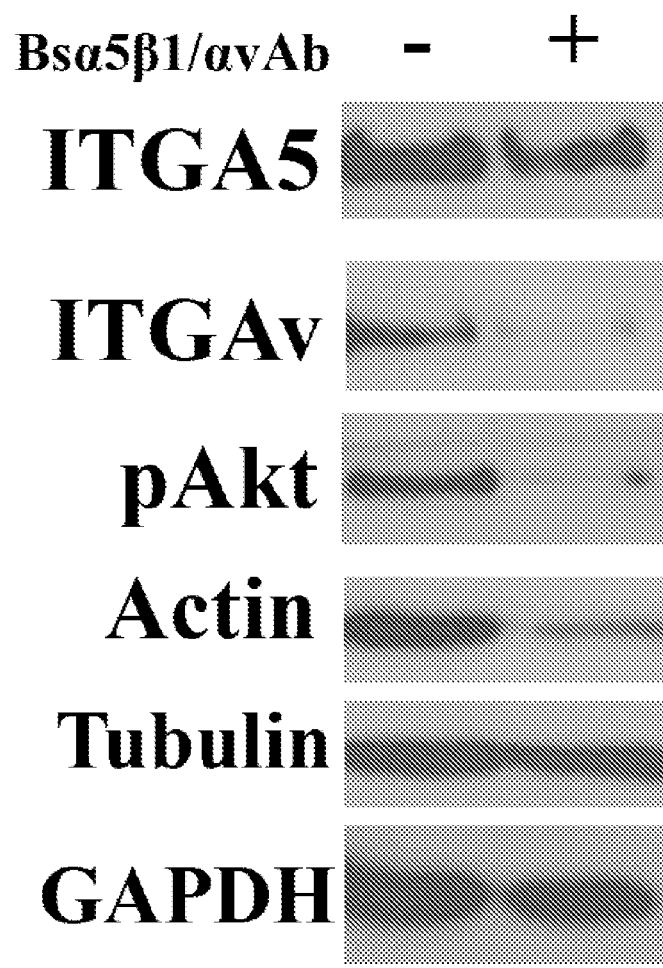
FIG. 19 is a Western blot showing the effect of antibody treatment on expression of various proteins in activated fibroblasts.

Activated fibroblasts were treated with or without 10 μg/mL of ITGA5B1xAV for 20 minutes on ice before being seeded into 6-well plates. 72 h later, cells were harvested for Western blot. Given the known functions of the target integrins in activated fibroblasts exhibiting alpha-smooth muscle actin expression, the impact of the bispecific antibody on integrin fate, α-smooth muscle actin expression, signaling, and cell viability was assessed. The data in FIG. 19 demonstrate that treatment with ITGA5B1xAV results in a strong downregulation of integrin αv and α5, loss of actin expression and blockade of Akt signaling in these cells, without loss of cell viability. These data suggest a possible reprogramming of activated fibroblasts by ITGA5B1xAV treatment. This would have implications for fibroblasts associated with cancer as well as other pathological fibrotic conditions in which αv signaling has been implicated, including scleroderma and related pathophysiological states such as chronic graft-versus-host disease.

What is claimed is:

1. A bispecific antibody comprising
(a) a first paratope that specifically binds an alpha-V integrin and comprises a light chain variable domain comprising the following CDR amino acid sequences: RASQDISNYLA (P1VLCDR1, SEQ ID NO:1), YTSKIHS (P1VLCDR2, SEQ ID NO:2), and QQGNTFPYT (P1VLCDR3, SEQ ID NO:3), and a heavy chain variable domain comprising the following CDR amino acid sequences: SFWMH (P1VHCDR1, SEQ ID NO:4), YINPRSGYTEYNEIFRD (P1VHCDR2, SEQ ID NO:5); and FLGRGAMDY (P1VHCDR3, SEQ ID NO:6); and
(b) a second paratope that specifically binds an α5 integrin and comprises a light chain variable domain comprising the following CDR amino acid sequences: TASSSVSSNYLH (P2VLCDR1, SEQ ID NO:7), STSNLAS (P2VLCDR2, SEQ ID NO:8), and HQYLRSPPT (P2VLCDR3, SEQ ID NO:9), and a heavy chain variable domain comprising the following CDR amino acid sequences: GFSLTDYGVH (P2VHCDR1, SEQ ID NO 10), VIWSDGSSTYN-SALKS (P2VHCDR2, SEQ ID NO 11), and HGTYYGMTTTGDALDY (P2VHCDR3, SEQ ID NO:12).

2. The bispecific antibody of claim 1, wherein
(a) the light chain variable domain of the first paratope further comprises framework regions (FRs) comprising at least one of the following FR amino acid sequences: DIQMTQSPSSLSASVGDRVTITC (P1VLFR1, SEQ ID NO:13), WYQQKPGKAPKLLIY (P1VLFR2, SEQ ID NO:14), GVPSRFSGSGSGTDYTFTISSLQPEDI-ATYYC (P1VLFR3, SEQ ID NO:15), FGQGTKVEIK (P1VLFR4, SEQ ID NO:16), or an amino acid sequence at least 80% identical to any of those four; or (b) the heavy chain variable domain of the first paratope further comprises FRs comprising at least one of the following FR amino acid sequences: QVQLQQSGAE-LAEPGASVKMSCKASGYTFS (P1VHFR1-1, SEQ ID NO:17), QVQLQQSGGELAKPGASVKVSCK-ASGYTFS (P1VHFR1-2, SEQ ID NO: 118), WVRQAPGQGLEWIG (P1VHFR2, SEQ ID NO.18), KATMTTDTSTSTAYMELSSLRSEDTAVYYCAS (P1VHFR3, SEQ ID NO:19), WGQGTTVTVSS (P1VHFR4, SEQ ID NO:20), or an amino acid sequence at least 80% identical to any of those four; or (c) the light chain variable domain of the second paratope further comprises FRs comprising at least one of the following FR amino acid sequences: QIVLTQSPAIM-SASLGERVTMTC (P2VLFR1, SEQ ID NO:21), WYQQKPGSAPNLWIY (P2VLFR2, SEQ ID NO:22), GVPARFSGSGSGTSYSLTISSMEAEDAATYYC (P2VLFR3, SEQ ID NO:23), FGGGTKLEIK (P2VLFR4, SEQ ID NO:24), or an amino acid sequence at least 80% identical to any of those four; or (d) the heavy chain variable domain of the second paratope further comprises FRs comprising at least one of the following FR amino acid sequences: QVQL-KESGPGLVAPSQSLSITCTIS (P2VHFR1, SEQ ID NO:25), WVRQPPGKGLEWLV (P2VHFR2, SEQ ID NO:26), RMTIRKDNSKSQVFLIMNSLQTDD-SAMYYCAR (P2VHFR3, SEQ ID NO:27), WGQGTSVTVSS (P2VHFR4, SEQ ID NO:28), or an amino acid sequence at least 80% identical to any of those four.

3. The bispecific antibody of claim 1, wherein the bispecific antibody comprises (i) an antigen binding fragment (Fab) portion that contains one of the two paratopes and (ii) a single-chain Fv (scFv) portion that contains the other paratope.

4. The bispecific antibody of claim 1, further comprising an Fc region.

5. The bispecific antibody of claim 2, further comprising an Fc region.

6. The bispecific antibody of claim 3, further comprising an Fc region.

7. The bispecific antibody of claim 1, wherein the bispecific antibody comprises
two polypeptides, each comprising an amino acid sequence at least 80% identical to SEQ ID NO: 63; and
two additional polypeptides, each comprising an amino acid sequence at least 80% identical to SEQ ID NO: 64.

8. The bispecific antibody of claim 4, wherein the bispecific antibody is at least partially humanized.

9. A pharmaceutical composition comprising the bispecific antibody of any one of claims 1-8 and a pharmaceutically acceptable carrier.

10. A method of treating cancer, the method comprising administering a therapeutically effective amount of the pharmaceutical composition of claim 9 to a cancer patient.

11. A method of treating a fibrotic condition, the method comprising administering a therapeutically effective amount of the pharmaceutical composition of claim 9 to a patient having a condition characterized by fibrosis.

12. A method of treating pathological angiogenesis, the method comprising administering a therapeutically effective amount of the pharmaceutical composition of claim 9 to a patient having a condition characterized by pathological angiogenesis.

* * * * *

SEQUENCE LISTING

```
<160> NUMBER OF SEQ ID NOS: 118

<210> SEQ ID NO 1
<211> LENGTH: 11
<212> TYPE: PRT
<213> ORGANISM: Artificial Sequence
<220> FEATURE:
<223> OTHER INFORMATION: synthetically generated peptide

<400> SEQUENCE: 1

Arg Ala Ser Gln Asp Ile Ser Asn Tyr Leu Ala
1               5                   10

<210> SEQ ID NO 2
<211> LENGTH: 7
<212> TYPE: PRT
<213> ORGANISM: Artificial Sequence
<220> FEATURE:
<223> OTHER INFORMATION: synthetically generated peptide

<400> SEQUENCE: 2

Tyr Thr Ser Lys Ile His Ser
1               5

<210> SEQ ID NO 3
<211> LENGTH: 9
<212> TYPE: PRT
<213> ORGANISM: Artificial Sequence
<220> FEATURE:
<223> OTHER INFORMATION: synthetically generated peptide

<400> SEQUENCE: 3

Gln Gln Gly Asn Thr Phe Pro Tyr Thr
1               5

<210> SEQ ID NO 4
<211> LENGTH: 5
<212> TYPE: PRT
```

```
<213> ORGANISM: Artificial Sequence
<220> FEATURE:
<223> OTHER INFORMATION: synthetically generated peptide

<400> SEQUENCE: 4

Ser Phe Trp Met His
1               5

<210> SEQ ID NO 5
<211> LENGTH: 17
<212> TYPE: PRT
<213> ORGANISM: Artificial Sequence
<220> FEATURE:
<223> OTHER INFORMATION: synthetically generated peptide

<400> SEQUENCE: 5

Tyr Ile Asn Pro Arg Ser Gly Tyr Thr Glu Tyr Asn Glu Ile Phe Arg
1               5                   10                  15

Asp

<210> SEQ ID NO 6
<211> LENGTH: 9
<212> TYPE: PRT
<213> ORGANISM: Artificial Sequence
<220> FEATURE:
<223> OTHER INFORMATION: synthetically generated peptide

<400> SEQUENCE: 6

Phe Leu Gly Arg Gly Ala Met Asp Tyr
1               5

<210> SEQ ID NO 7
<211> LENGTH: 12
<212> TYPE: PRT
<213> ORGANISM: Artificial Sequence
<220> FEATURE:
<223> OTHER INFORMATION: synthetically generated peptide

<400> SEQUENCE: 7

Thr Ala Ser Ser Ser Val Ser Ser Asn Tyr Leu His
1               5                   10

<210> SEQ ID NO 8
<211> LENGTH: 7
<212> TYPE: PRT
<213> ORGANISM: Artificial Sequence
<220> FEATURE:
<223> OTHER INFORMATION: synthetically generated peptide

<400> SEQUENCE: 8

Ser Thr Ser Asn Leu Ala Ser
1               5

<210> SEQ ID NO 9
<211> LENGTH: 9
<212> TYPE: PRT
<213> ORGANISM: Artificial Sequence
<220> FEATURE:
<223> OTHER INFORMATION: synthetically generated peptide

<400> SEQUENCE: 9

His Gln Tyr Leu Arg Ser Pro Pro Thr
1               5

<210> SEQ ID NO 10
<211> LENGTH: 10
```

```
<212> TYPE: PRT
<213> ORGANISM: Artificial Sequence
<220> FEATURE:
<223> OTHER INFORMATION: synthetically generated peptide

<400> SEQUENCE: 10

Gly Phe Ser Leu Thr Asp Tyr Gly Val His
1               5                   10

<210> SEQ ID NO 11
<211> LENGTH: 16
<212> TYPE: PRT
<213> ORGANISM: Artificial Sequence
<220> FEATURE:
<223> OTHER INFORMATION: synthetically generated peptide

<400> SEQUENCE: 11

Val Ile Trp Ser Asp Gly Ser Ser Thr Tyr Asn Ser Ala Leu Lys Ser
1               5                   10                  15

<210> SEQ ID NO 12
<211> LENGTH: 16
<212> TYPE: PRT
<213> ORGANISM: Artificial Sequence
<220> FEATURE:
<223> OTHER INFORMATION: synthetically generated peptide

<400> SEQUENCE: 12

His Gly Thr Tyr Tyr Gly Met Thr Thr Thr Gly Asp Ala Leu Asp Tyr
1               5                   10                  15

<210> SEQ ID NO 13
<211> LENGTH: 23
<212> TYPE: PRT
<213> ORGANISM: Artificial Sequence
<220> FEATURE:
<223> OTHER INFORMATION: synthetically generated peptide

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 14
<211> LENGTH: 15
<212> TYPE: PRT
<213> ORGANISM: Artificial Sequence
<220> FEATURE:
<223> OTHER INFORMATION: synthetically generated peptide

<400> SEQUENCE: 14

Trp Tyr Gln Gln Lys Pro Gly Lys Ala Pro Lys Leu Leu Ile Tyr
1               5                   10                  15

<210> SEQ ID NO 15
<211> LENGTH: 32
<212> TYPE: PRT
<213> ORGANISM: Artificial Sequence
<220> FEATURE:
<223> OTHER INFORMATION: synthetically generated peptide;

<400> SEQUENCE: 15

Gly Val Pro Ser Arg Phe Ser Gly Ser Gly Ser Gly Thr Asp Tyr Thr
1               5                   10                  15

Phe Thr Ile Ser Ser Leu Gln Pro Glu Asp Ile Ala Thr Tyr Tyr Cys
```

20                  25                  30

<210> SEQ ID NO 16
<211> LENGTH: 10
<212> TYPE: PRT
<213> ORGANISM: Artificial Sequence
<220> FEATURE:
<223> OTHER INFORMATION: synthetically generated peptide

<400> SEQUENCE: 16

Phe Gly Gln Gly Thr Lys Val Glu Ile Lys
1               5                  10

<210> SEQ ID NO 17
<211> LENGTH: 30
<212> TYPE: PRT
<213> ORGANISM: Artificial Sequence
<220> FEATURE:
<223> OTHER INFORMATION: synthetically generated peptide

<400> SEQUENCE: 17

Gln Val Gln Leu Gln Gln Ser Gly Ala Glu Leu Ala Glu Pro Gly Ala
1               5                  10                  15

Ser Val Lys Met Ser Cys Lys Ala Ser Gly Tyr Thr Phe Ser
            20                  25                  30

<210> SEQ ID NO 18
<211> LENGTH: 14
<212> TYPE: PRT
<213> ORGANISM: Artificial Sequence
<220> FEATURE:
<223> OTHER INFORMATION: synthetically generated peptide

<400> SEQUENCE: 18

Trp Val Arg Gln Ala Pro Gly Gln Gly Leu Glu Trp Ile Gly
1               5                  10

<210> SEQ ID NO 19
<211> LENGTH: 32
<212> TYPE: PRT
<213> ORGANISM: Artificial Sequence
<220> FEATURE:
<223> OTHER INFORMATION: synthetically generated peptide

<400> SEQUENCE: 19

Lys Ala Thr Met Thr Thr Asp Thr Ser Thr Ser Thr Ala Tyr Met Glu
1               5                  10                  15

Leu Ser Ser Leu Arg Ser Glu Asp Thr Ala Val Tyr Tyr Cys Ala Ser
            20                  25                  30

<210> SEQ ID NO 20
<211> LENGTH: 11
<212> TYPE: PRT
<213> ORGANISM: Artificial Sequence
<220> FEATURE:
<223> OTHER INFORMATION: synthetically generated peptide

<400> SEQUENCE: 20

Trp Gly Gln Gly Thr Thr Val Thr Val Ser Ser
1               5                  10

<210> SEQ ID NO 21
<211> LENGTH: 23
<212> TYPE: PRT
<213> ORGANISM: Artificial Sequence
<220> FEATURE:

<223> OTHER INFORMATION: synthetically generated peptide

<400> SEQUENCE: 21

Gln Ile Val Leu Thr Gln Ser Pro Ala Ile Met Ser Ala Ser Leu Gly
1               5                   10                  15

Glu Arg Val Thr Met Thr Cys
            20

<210> SEQ ID NO 22
<211> LENGTH: 15
<212> TYPE: PRT
<213> ORGANISM: Artificial Sequence
<220> FEATURE:
<223> OTHER INFORMATION: synthetically generated peptide

<400> SEQUENCE: 22

Trp Tyr Gln Gln Lys Pro Gly Ser Ala Pro Asn Leu Trp Ile Tyr
1               5                   10                  15

<210> SEQ ID NO 23
<211> LENGTH: 32
<212> TYPE: PRT
<213> ORGANISM: Artificial Sequence
<220> FEATURE:
<223> OTHER INFORMATION: synthetically generated peptide

<400> SEQUENCE: 23

Gly Val Pro Ala Arg Phe Ser Gly Ser Gly Ser Gly Thr Ser Tyr Ser
1               5                   10                  15

Leu Thr Ile Ser Ser Met Glu Ala Glu Asp Ala Ala Thr Tyr Tyr Cys
            20                  25                  30

<210> SEQ ID NO 24
<211> LENGTH: 10
<212> TYPE: PRT
<213> ORGANISM: Artificial Sequence
<220> FEATURE:
<223> OTHER INFORMATION: synthetically generated peptide

<400> SEQUENCE: 24

Phe Gly Gly Gly Thr Lys Leu Glu Ile Lys
1               5                   10

<210> SEQ ID NO 25
<211> LENGTH: 25
<212> TYPE: PRT
<213> ORGANISM: Artificial Sequence
<220> FEATURE:
<223> OTHER INFORMATION: synthetically generated peptide

<400> SEQUENCE: 25

Gln Val Gln Leu Lys Glu Ser Gly Pro Gly Leu Val Ala Pro Ser Gln
1               5                   10                  15

Ser Leu Ser Ile Thr Cys Thr Ile Ser
            20                  25

<210> SEQ ID NO 26
<211> LENGTH: 14
<212> TYPE: PRT
<213> ORGANISM: Artificial Sequence
<220> FEATURE:
<223> OTHER INFORMATION: synthetically generated peptide

<400> SEQUENCE: 26

Trp Val Arg Gln Pro Pro Gly Lys Gly Leu Glu Trp Leu Val

<210> SEQ ID NO 27
<211> LENGTH: 32
<212> TYPE: PRT
<213> ORGANISM: Artificial Sequence
<220> FEATURE:
<223> OTHER INFORMATION: synthetically generated peptide

<400> SEQUENCE: 27

Arg Met Thr Ile Arg Lys Asp Asn Ser Lys Ser Gln Val Phe Leu Ile
1               5                   10                  15

Met Asn Ser Leu Gln Thr Asp Asp Ser Ala Met Tyr Tyr Cys Ala Arg
            20                  25                  30

<210> SEQ ID NO 28
<211> LENGTH: 11
<212> TYPE: PRT
<213> ORGANISM: Artificial Sequence
<220> FEATURE:
<223> OTHER INFORMATION: synthetically generated peptide

<400> SEQUENCE: 28

Trp Gly Gln Gly Thr Ser Val Thr Val Ser Ser
1               5                   10

<210> SEQ ID NO 29
<211> LENGTH: 19
<212> TYPE: PRT
<213> ORGANISM: Artificial Sequence
<220> FEATURE:
<223> OTHER INFORMATION: synthetically generated peptide

<400> SEQUENCE: 29

Met Glu Leu Gly Leu Ser Trp Ile Phe Leu Leu Ala Ile Leu Lys Gly
1               5                   10                  15

Val Gln Cys

<210> SEQ ID NO 30
<211> LENGTH: 20
<212> TYPE: PRT
<213> ORGANISM: Artificial Sequence
<220> FEATURE:
<223> OTHER INFORMATION: synthetically generated peptide

<400> SEQUENCE: 30

Met Arg Val Pro Ala Gln Leu Leu Gly Leu Leu Leu Leu Trp Leu Pro
1               5                   10                  15

Gly Thr Arg Cys
            20

<210> SEQ ID NO 31
<211> LENGTH: 721
<212> TYPE: PRT
<213> ORGANISM: Artificial Sequence
<220> FEATURE:
<223> OTHER INFORMATION: synthetically generated peptide

<400> SEQUENCE: 31

Met Glu Leu Gly Leu Ser Trp Ile Phe Leu Leu Ala Ile Leu Lys Gly
1               5                   10                  15

Val Gln Cys Gln Val Gln Leu Gln Gln Ser Gly Gly Glu Leu Ala Lys
            20                  25                  30

Pro Gly Ala Ser Val Lys Val Ser Cys Lys Ala Ser Gly Tyr Thr Phe

```
            35                  40                  45
Ser Ser Phe Trp Met His Trp Val Arg Gln Ala Pro Gly Gln Gly Leu
 50                  55                  60
Glu Trp Ile Gly Tyr Ile Asn Pro Arg Ser Gly Tyr Thr Glu Tyr Asn
 65                  70                  75                  80
Glu Ile Phe Arg Asp Lys Ala Thr Met Thr Thr Asp Thr Ser Thr Ser
                 85                  90                  95
Thr Ala Tyr Met Glu Leu Ser Ser Leu Arg Ser Glu Asp Thr Ala Val
                100                 105                 110
Tyr Tyr Cys Ala Ser Phe Leu Gly Arg Gly Ala Met Asp Tyr Trp Gly
            115                 120                 125
Gln Gly Thr Thr Val Thr Val Ser Ser Ala Ser Thr Lys Gly Pro Ser
130                 135                 140
Val Phe Pro Leu Ala Pro Cys Ser Arg Ser Thr Ser Glu Ser Thr Ala
145                 150                 155                 160
Ala Leu Gly Cys Leu Val Lys Asp Tyr Phe Pro Glu Pro Val Thr Val
                165                 170                 175
Ser Trp Asn Ser Gly Ala Leu Thr Ser Gly Val His Thr Phe Pro Pro
            180                 185                 190
Ala Val Leu Gln Ser Ser Gly Leu Tyr Ser Leu Ser Ser Val Val Thr
        195                 200                 205
Val Pro Ser Ser Asn Phe Gly Thr Gln Thr Tyr Thr Cys Asn Val Asp
210                 215                 220
His Lys Pro Ser Asn Thr Lys Val Asp Lys Thr Val Glu Arg Lys Cys
225                 230                 235                 240
Cys Val Glu Cys Pro Pro Cys Pro Ala Pro Pro Val Ala Gly Pro Ser
                245                 250                 255
Val Phe Leu Phe Pro Pro Lys Pro Lys Asp Thr Leu Met Ile Ser Arg
            260                 265                 270
Thr Pro Glu Val Thr Cys Val Val Val Asp Val Ser His Glu Asp Pro
        275                 280                 285
Glu Val Gln Phe Asn Trp Tyr Val Asp Gly Val Glu Val His Asn Ala
290                 295                 300
Lys Thr Lys Pro Arg Glu Glu Gln Phe Asn Ser Thr Phe Arg Val Val
305                 310                 315                 320
Ser Val Leu Thr Val Val His Gln Asp Trp Leu Asn Gly Lys Glu Tyr
                325                 330                 335
Lys Cys Lys Val Ser Asn Lys Gly Leu Pro Ala Pro Ile Glu Lys Thr
            340                 345                 350
Ile Ser Lys Thr Lys Gly Gln Pro Arg Glu Pro Gln Val Tyr Thr Leu
        355                 360                 365
Pro Pro Ser Arg Glu Glu Met Thr Lys Asn Gln Val Ser Leu Thr Cys
370                 375                 380
Leu Val Lys Gly Phe Tyr Pro Ser Asp Ile Ala Val Glu Trp Glu Ser
385                 390                 395                 400
Asn Gly Gln Pro Glu Asn Asn Tyr Lys Thr Thr Pro Pro Met Leu Asp
                405                 410                 415
Ser Asp Gly Ser Phe Phe Leu Tyr Ser Lys Leu Thr Val Asp Lys Ser
            420                 425                 430
Arg Trp Gln Gln Gly Asn Val Phe Ser Cys Ser Val Met His Glu Ala
        435                 440                 445
Leu His Asn His Tyr Thr Gln Lys Ser Leu Ser Leu Ser Pro Gly Lys
450                 455                 460
```

Gly Gly Gly Gly Ser Gly Gly Gly Ser Gln Val Gln Leu Lys Glu
465                 470                 475                 480

Ser Gly Pro Gly Leu Val Ala Pro Ser Gln Ser Leu Ser Ile Thr Cys
            485                 490                 495

Thr Ile Ser Gly Phe Ser Leu Thr Asp Tyr Gly Val His Trp Val Arg
            500                 505                 510

Gln Pro Pro Gly Lys Gly Leu Glu Trp Leu Val Val Ile Trp Ser Asp
            515                 520                 525

Gly Ser Ser Thr Tyr Asn Ser Ala Leu Lys Ser Arg Met Thr Ile Arg
            530                 535                 540

Lys Asp Asn Ser Lys Ser Gln Val Phe Leu Ile Met Asn Ser Leu Gln
545                 550                 555                 560

Thr Asp Asp Ser Ala Met Tyr Tyr Cys Ala Arg His Gly Thr Tyr Tyr
            565                 570                 575

Gly Met Thr Thr Thr Gly Asp Ala Leu Asp Tyr Trp Gly Gln Gly Thr
            580                 585                 590

Ser Val Thr Val Ser Ser Gly Gly Gly Ser Gly Gly Gly Gly Ser
            595                 600                 605

Gly Gly Gly Gly Ser Gln Ile Val Leu Thr Gln Ser Pro Ala Ile Met
610                 615                 620

Ser Ala Ser Leu Gly Glu Arg Val Thr Met Thr Cys Thr Ala Ser Ser
625                 630                 635                 640

Ser Val Ser Ser Asn Tyr Leu His Trp Tyr Gln Gln Lys Pro Gly Ser
            645                 650                 655

Ala Pro Asn Leu Trp Ile Tyr Ser Thr Ser Asn Leu Ala Ser Gly Val
            660                 665                 670

Pro Ala Arg Phe Ser Gly Ser Gly Ser Gly Thr Ser Tyr Ser Leu Thr
            675                 680                 685

Ile Ser Ser Met Glu Ala Glu Asp Ala Ala Thr Tyr Tyr Cys His Gln
            690                 695                 700

Tyr Leu Arg Ser Pro Pro Thr Phe Gly Gly Gly Thr Lys Leu Glu Ile
705                 710                 715                 720

Lys

<210> SEQ ID NO 32
<211> LENGTH: 234
<212> TYPE: PRT
<213> ORGANISM: Artificial Sequence
<220> FEATURE:
<223> OTHER INFORMATION: synthetically generated peptide

<400> SEQUENCE: 32

Met Arg Val Pro Ala Gln Leu Leu Gly Leu Leu Leu Leu Trp Leu Pro
1               5                   10                  15

Gly Thr Arg Cys Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
            35                  40                  45

Ile Ser Asn Tyr Leu Ala Trp Tyr Gln Gln Lys Pro Gly Lys Ala Pro
        50                  55                  60

Lys Leu Leu Ile Tyr Tyr Thr Ser Lys Ile His Ser Gly Val Pro Ser
65              70                  75                  80

Arg Phe Ser Gly Ser Gly Ser Gly Thr Asp Tyr Thr Phe Thr Ile Ser
            85                  90                  95

```
Ser Leu Gln Pro Glu Asp Ile Ala Thr Tyr Tyr Cys Gln Gln Gly Asn
            100                 105                 110

Thr Phe Pro Tyr Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 33
<211> LENGTH: 11
<212> TYPE: PRT
<213> ORGANISM: Artificial Sequence
<220> FEATURE:
<223> OTHER INFORMATION: synthetically generated peptide

<400> SEQUENCE: 33

Arg Ala Ser Gln Ser Val Ser Ser Tyr Leu Ala
1               5                   10

<210> SEQ ID NO 34
<211> LENGTH: 7
<212> TYPE: PRT
<213> ORGANISM: Artificial Sequence
<220> FEATURE:
<223> OTHER INFORMATION: synthetically generated peptide

<400> SEQUENCE: 34

Asp Ala Ser Asn Arg Ala Thr
1               5

<210> SEQ ID NO 35
<211> LENGTH: 9
<212> TYPE: PRT
<213> ORGANISM: Artificial Sequence
<220> FEATURE:
<223> OTHER INFORMATION: synthetically generated peptide

<400> SEQUENCE: 35

Gln Gln Arg Ser Asn Trp Pro Leu Thr
1               5

<210> SEQ ID NO 36
<211> LENGTH: 6
<212> TYPE: PRT
<213> ORGANISM: Artificial Sequence
<220> FEATURE:
<223> OTHER INFORMATION: synthetically generated peptide

<400> SEQUENCE: 36

Ser Ser Ser Tyr Trp Gly
1               5
```

```
<210> SEQ ID NO 37
<211> LENGTH: 16
<212> TYPE: PRT
<213> ORGANISM: Artificial Sequence
<220> FEATURE:
<223> OTHER INFORMATION: synthetically generated peptide

<400> SEQUENCE: 37

Ser Ile Tyr Tyr Ser Gly Arg Asn Tyr Asn Asn Pro Ser Leu Lys Ser
1               5                   10                  15

<210> SEQ ID NO 38
<211> LENGTH: 15
<212> TYPE: PRT
<213> ORGANISM: Artificial Sequence
<220> FEATURE:
<223> OTHER INFORMATION: synthetically generated peptide

<400> SEQUENCE: 38

His Tyr Tyr Gly Ser Gly Ser Ser Tyr Tyr Tyr Asp Leu Asp
1               5                   10                  15

<210> SEQ ID NO 39
<211> LENGTH: 5
<212> TYPE: PRT
<213> ORGANISM: Artificial Sequence
<220> FEATURE:
<223> OTHER INFORMATION: synthetically generated peptide

<400> SEQUENCE: 39

Ser Tyr Ala Met His
1               5

<210> SEQ ID NO 40
<211> LENGTH: 17
<212> TYPE: PRT
<213> ORGANISM: Artificial Sequence
<220> FEATURE:
<223> OTHER INFORMATION: synthetically generated peptide

<400> SEQUENCE: 40

Val Ile Ser Phe Asp Gly Ser Asn Lys Asn Tyr Ala Asp Ser Val Lys
1               5                   10                  15

Gly

<210> SEQ ID NO 41
<211> LENGTH: 12
<212> TYPE: PRT
<213> ORGANISM: Artificial Sequence
<220> FEATURE:
<223> OTHER INFORMATION: synthetically generated peptide

<400> SEQUENCE: 41

Glu Tyr Trp Gly Thr Tyr Tyr Tyr Gly Met Asp Val
1               5                   10

<210> SEQ ID NO 42
<211> LENGTH: 6
<212> TYPE: PRT
<213> ORGANISM: Artificial Sequence
<220> FEATURE:
<223> OTHER INFORMATION: synthetically generated peptide

<400> SEQUENCE: 42

Ser Thr Tyr Ala Met His
1               5
```

<210> SEQ ID NO 43
<211> LENGTH: 17
<212> TYPE: PRT
<213> ORGANISM: Artificial Sequence
<220> FEATURE:
<223> OTHER INFORMATION: synthetically generated peptide

<400> SEQUENCE: 43

```
Val Ile Ser Tyr Asp Gly Ser Asn Lys Tyr Tyr Ala Asp Ser Val Lys
1               5                   10                  15

Gly
```

<210> SEQ ID NO 44
<211> LENGTH: 14
<212> TYPE: PRT
<213> ORGANISM: Artificial Sequence
<220> FEATURE:
<223> OTHER INFORMATION: synthetically generated peptide

<400> SEQUENCE: 44

```
Arg Glu Ser Pro Pro Ile Tyr Tyr Tyr Tyr Gly Met Asp Val
1               5                   10
```

<210> SEQ ID NO 45
<211> LENGTH: 10
<212> TYPE: PRT
<213> ORGANISM: Artificial Sequence
<220> FEATURE:
<223> OTHER INFORMATION: synthetically generated peptide

<400> SEQUENCE: 45

```
Gly Gly Gly Gly Ser Gly Gly Gly Gly Ser
1               5                   10
```

<210> SEQ ID NO 46
<211> LENGTH: 15
<212> TYPE: PRT
<213> ORGANISM: Artificial Sequence
<220> FEATURE:
<223> OTHER INFORMATION: synthetically generated peptide

<400> SEQUENCE: 46

```
Gly Gly Gly Gly Ser Gly Gly Gly Gly Ser Gly Gly Gly Gly Ser
1               5                   10                  15
```

<210> SEQ ID NO 47
<211> LENGTH: 721
<212> TYPE: PRT
<213> ORGANISM: Artificial Sequence
<220> FEATURE:
<223> OTHER INFORMATION: synthetically generated peptide

<400> SEQUENCE: 47

```
Met Glu Leu Gly Leu Ser Trp Ile Phe Leu Leu Ala Ile Leu Lys Gly
1               5                   10                  15

Val Gln Cys Gln Val Gln Leu Gln Gln Ser Gly Gly Glu Leu Ala Lys
                20                  25                  30

Pro Gly Ala Ser Val Lys Val Ser Cys Lys Ala Ser Gly Tyr Thr Phe
            35                  40                  45

Ser Ser Phe Trp Met His Trp Val Arg Gln Ala Pro Gly Gln Gly Leu
        50                  55                  60

Glu Trp Ile Gly Tyr Ile Asn Pro Arg Ser Gly Tyr Thr Glu Tyr Asn
65                  70                  75                  80
```

-continued

```
Glu Ile Phe Arg Asp Lys Ala Thr Met Thr Thr Asp Thr Ser Thr Ser
             85                  90                  95
Thr Ala Tyr Met Glu Leu Ser Ser Leu Arg Ser Glu Asp Thr Ala Val
            100                 105                 110
Tyr Tyr Cys Ala Ser Phe Leu Gly Arg Gly Ala Met Asp Tyr Trp Gly
            115                 120                 125
Gln Gly Thr Thr Val Thr Val Ser Ser Ala Ser Thr Lys Gly Pro Ser
130                 135                 140
Val Phe Pro Leu Ala Pro Cys Ser Arg Ser Thr Ser Glu Ser Thr Ala
145                 150                 155                 160
Ala Leu Gly Cys Leu Val Lys Asp Tyr Phe Pro Glu Pro Val Thr Val
                165                 170                 175
Ser Trp Asn Ser Gly Ala Leu Thr Ser Gly Val His Thr Phe Pro Pro
            180                 185                 190
Ala Val Leu Gln Ser Ser Gly Leu Tyr Ser Leu Ser Ser Val Val Thr
            195                 200                 205
Val Pro Ser Ser Asn Phe Gly Thr Gln Thr Tyr Thr Cys Asn Val Asp
            210                 215                 220
His Lys Pro Ser Asn Thr Lys Val Asp Lys Thr Val Glu Arg Lys Cys
225                 230                 235                 240
Cys Val Glu Cys Pro Pro Cys Pro Ala Pro Pro Val Ala Gly Pro Ser
                245                 250                 255
Val Phe Leu Phe Pro Pro Lys Pro Lys Asp Thr Leu Met Ile Ser Arg
                260                 265                 270
Thr Pro Glu Val Thr Cys Val Val Asp Val Ser His Glu Asp Pro
                275                 280                 285
Glu Val Gln Phe Asn Trp Tyr Val Asp Gly Val Glu Val His Asn Ala
            290                 295                 300
Lys Thr Lys Pro Arg Glu Glu Gln Phe Asn Ser Thr Phe Arg Val Val
305                 310                 315                 320
Ser Val Leu Thr Val Val His Gln Asp Trp Leu Asn Gly Lys Glu Tyr
                325                 330                 335
Lys Cys Lys Val Ser Asn Lys Gly Leu Pro Ala Pro Ile Glu Lys Thr
                340                 345                 350
Ile Ser Lys Thr Lys Gly Gln Pro Arg Glu Pro Gln Val Tyr Thr Leu
            355                 360                 365
Pro Pro Ser Arg Glu Glu Met Thr Lys Asn Gln Val Ser Leu Thr Cys
370                 375                 380
Leu Val Lys Gly Phe Tyr Pro Ser Asp Ile Ala Val Glu Trp Glu Ser
385                 390                 395                 400
Asn Gly Gln Pro Glu Asn Asn Tyr Lys Thr Thr Pro Pro Met Leu Asp
                405                 410                 415
Ser Asp Gly Ser Phe Phe Leu Tyr Ser Lys Leu Thr Val Asp Lys Ser
            420                 425                 430
Arg Trp Gln Gln Gly Asn Val Phe Ser Cys Ser Val Met His Glu Ala
            435                 440                 445
Leu His Asn His Tyr Thr Gln Lys Ser Leu Ser Leu Ser Pro Gly Lys
            450                 455                 460
Gly Gly Gly Gly Ser Gly Gly Gly Ser Gln Val Gln Leu Lys Glu
465                 470                 475                 480
Ser Gly Pro Gly Leu Val Ala Pro Ser Gln Ser Leu Ser Ile Thr Cys
                485                 490                 495
```

```
Thr Ile Ser Gly Phe Ser Leu Thr Asp Tyr Gly Val His Trp Val Arg
                500                 505                 510
Gln Pro Pro Gly Lys Gly Leu Glu Trp Leu Val Val Ile Trp Ser Asp
        515                 520                 525
Gly Ser Ser Thr Tyr Asn Ser Ala Leu Lys Ser Arg Met Thr Ile Arg
    530                 535                 540
Lys Asp Asn Ser Lys Ser Gln Val Phe Leu Ile Met Asn Ser Leu Gln
545                 550                 555                 560
Thr Asp Asp Ser Ala Met Tyr Tyr Cys Ala Arg His Gly Thr Tyr Tyr
                565                 570                 575
Gly Met Thr Thr Thr Gly Asp Ala Leu Asp Tyr Trp Gly Gln Gly Thr
            580                 585                 590
Ser Val Thr Val Ser Ser Gly Gly Gly Ser Gly Gly Gly Gly Ser
            595                 600                 605
Gly Gly Gly Gly Ser Gln Ile Val Leu Thr Gln Ser Pro Ala Ile Met
    610                 615                 620
Ser Ala Ser Leu Gly Glu Arg Val Thr Met Thr Cys Thr Ala Ser Ser
625                 630                 635                 640
Ser Val Ser Ser Asn Tyr Leu His Trp Tyr Gln Gln Lys Pro Gly Ser
                645                 650                 655
Ala Pro Asn Leu Trp Ile Tyr Ser Thr Ser Asn Leu Ala Ser Gly Val
            660                 665                 670
Pro Ala Arg Phe Ser Gly Ser Gly Ser Gly Thr Ser Tyr Ser Leu Thr
        675                 680                 685
Ile Ser Ser Met Glu Ala Glu Asp Ala Ala Thr Tyr Tyr Cys His Gln
    690                 695                 700
Tyr Leu Arg Ser Pro Pro Thr Phe Gly Gly Gly Thr Lys Leu Glu Ile
705                 710                 715                 720
Lys

<210> SEQ ID NO 48
<211> LENGTH: 234
<212> TYPE: PRT
<213> ORGANISM: Artificial Sequence
<220> FEATURE:
<223> OTHER INFORMATION: synthetically generated peptid

<400> SEQUENCE: 48

Met Arg Val Pro Ala Gln Leu Leu Gly Leu Leu Leu Leu Trp Leu Pro
1               5                   10                  15
Gly Thr Arg Cys Asp Ile Gln Met Thr Gln Ser Pro Ser Ser Leu Ser
            20                  25                  30
Ala Ser Val Gly Asp Arg Val Thr Ile Thr Cys Arg Ala Ser Gln Asp
        35                  40                  45
Ile Ser Asn Tyr Leu Ala Trp Tyr Gln Gln Lys Pro Gly Lys Ala Pro
    50                  55                  60
Lys Leu Leu Ile Tyr Tyr Thr Ser Lys Ile His Ser Gly Val Pro Ser
65                  70                  75                  80
Arg Phe Ser Gly Ser Gly Ser Gly Thr Asp Tyr Thr Phe Thr Ile Ser
                85                  90                  95
Ser Leu Gln Pro Glu Asp Ile Ala Thr Tyr Tyr Cys Gln Gln Gly Asn
            100                 105                 110
Thr Phe Pro Tyr Thr Phe Gly Gln Gly Thr Lys Val Glu Ile Lys Arg
        115                 120                 125
Thr Val Ala Ala Pro Ser Val Phe Ile Phe Pro Pro Ser Asp Glu Gln
```

```
                130                 135                 140
Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 49
<211> LENGTH: 124
<212> TYPE: PRT
<213> ORGANISM: Mus musculus

<400> SEQUENCE: 49

Gln Val Gln Leu Lys Glu Ser Gly Pro Gly Leu Val Ala Pro Ser Gln
1               5                   10                  15

Ser Leu Ser Ile Thr Cys Thr Ile Ser Gly Phe Ser Leu Thr Asp Tyr
            20                  25                  30

Gly Val His Trp Val Arg Gln Pro Pro Gly Lys Gly Leu Glu Trp Leu
        35                  40                  45

Val Val Ile Trp Ser Asp Gly Ser Ser Thr Tyr Asn Ser Ala Leu Lys
    50                  55                  60

Ser Arg Met Thr Ile Arg Lys Asp Asn Ser Lys Ser Gln Val Phe Leu
65                  70                  75                  80

Ile Met Asn Ser Leu Gln Thr Asp Asp Ser Ala Met Tyr Tyr Cys Ala
                85                  90                  95

Arg His Gly Thr Tyr Tyr Gly Met Thr Thr Gly Asp Ala Leu Asp
            100                 105                 110

Tyr Trp Gly Gln Gly Thr Ser Val Thr Val Ser Ser
        115                 120

<210> SEQ ID NO 50
<211> LENGTH: 124
<212> TYPE: PRT
<213> ORGANISM: Artificial Sequence
<220> FEATURE:
<223> OTHER INFORMATION: synthetically generated peptide

<400> SEQUENCE: 50

Gln Val Gln Leu Val Glu Ser Gly Pro Gly Leu Val Gln Pro Gly Gly
1               5                   10                  15

Ser Leu Arg Ile Ser Cys Ala Ile Ser Gly Phe Ser Leu Thr Asp Tyr
            20                  25                  30

Gly Val His Trp Val Arg Gln Ala Pro Gly Lys Gly Leu Glu Trp Leu
        35                  40                  45

Val Val Ile Trp Ser Asp Gly Ser Ser Thr Tyr Asn Ser Ala Leu Lys
    50                  55                  60

Ser Arg Met Thr Ile Ser Lys Asp Asn Ser Lys Ser Thr Val Tyr Leu
65                  70                  75                  80

Gln Met Asn Ser Leu Arg Ala Glu Asp Thr Ala Met Tyr Tyr Cys Ala
                85                  90                  95
```

Arg His Gly Thr Tyr Tyr Gly Met Thr Thr Thr Gly Asp Ala Leu Asp
            100                 105                 110

Tyr Trp Gly Gln Gly Thr Leu Val Thr Val Ser Ser
        115                 120

<210> SEQ ID NO 51
<211> LENGTH: 124
<212> TYPE: PRT
<213> ORGANISM: Artificial Sequence
<220> FEATURE:
<223> OTHER INFORMATION: synthetically generated peptide

<400> SEQUENCE: 51

Glu Val Gln Leu Val Glu Ser Gly Gly Gly Leu Val Gln Pro Gly Gly
1               5                   10                  15

Ser Leu Arg Ile Ser Cys Ala Ile Ser Gly Phe Ser Leu Thr Asp Tyr
            20                  25                  30

Gly Val His Trp Val Arg Gln Ala Pro Gly Lys Gly Leu Glu Trp Leu
        35                  40                  45

Val Val Ile Trp Ser Asp Gly Ser Ser Thr Tyr Asn Ser Ala Leu Lys
    50                  55                  60

Ser Arg Met Thr Ile Ser Lys Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg His Gly Thr Tyr Tyr Gly Met Thr Thr Thr Gly Asp Ala Leu Asp
            100                 105                 110

Tyr Trp Gly Gln Gly Thr Leu Val Thr Val Ser Ser
        115                 120

<210> SEQ ID NO 52
<211> LENGTH: 124
<212> TYPE: PRT
<213> ORGANISM: Artificial Sequence
<220> FEATURE:
<223> OTHER INFORMATION: synthetically generated peptide

<400> SEQUENCE: 52

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Asp Tyr
            20                  25                  30

Gly Val His Trp Val Arg Gln Ala Pro Gly Lys Gly Leu Glu Trp Val
        35                  40                  45

Ser Val Ile Trp Ser Asp Gly Ser Ser Thr Tyr Asn Ser Ala Leu Lys
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg His Gly Thr Tyr Tyr Gly Met Thr Thr Thr Gly Asp Ala Leu Asp
            100                 105                 110

Tyr Trp Gly Gln Gly Thr Leu Val Thr Val Ser Ser
        115                 120

<210> SEQ ID NO 53
<211> LENGTH: 124
<212> TYPE: PRT

<213> ORGANISM: Artificial Sequence
<220> FEATURE:
<223> OTHER INFORMATION: synthetically generated peptide

<400> SEQUENCE: 53

Glu Val Gln Leu Val Glu Ser Gly Gly Gly Leu Val Gln Pro Gly Gly
1               5                   10                  15

Ser Leu Arg Leu Ser Cys Ala Ile Ser Gly Phe Ser Leu Thr Asp Tyr
            20                  25                  30

Gly Val His Trp Val Arg Gln Ala Pro Gly Lys Gly Leu Glu Trp Leu
        35                  40                  45

Val Val Ile Trp Ser Asp Gly Ser Ser Thr Tyr Asn Ser Ala Leu Lys
    50                  55                  60

Ser Arg Met Thr Ile Ser Lys Asp Asn Ser Lys Ser Thr Val Tyr Leu
65                  70                  75                  80

Gln Met Asn Ser Leu Arg Ala Glu Asp Thr Ala Val Tyr Tyr Cys Ala
                85                  90                  95

Arg His Gly Thr Tyr Tyr Gly Met Thr Thr Thr Gly Asp Ala Leu Asp
            100                 105                 110

Tyr Trp Gly Gln Gly Thr Leu Val Thr Val Ser Ser
        115                 120

<210> SEQ ID NO 54
<211> LENGTH: 124
<212> TYPE: PRT
<213> ORGANISM: Artificial Sequence
<220> FEATURE:
<223> OTHER INFORMATION: synthetically generated peptide

<400> SEQUENCE: 54

Gln Val Gln Leu Val Glu Ser Gly Gly Gly Leu Val Gln Pro Gly Gly
1               5                   10                  15

Ser Leu Arg Ile Ser Cys Ala Ile Ser Gly Phe Ser Leu Thr Asp Tyr
            20                  25                  30

Gly Val His Trp Val Arg Gln Ala Pro Gly Lys Gly Leu Glu Trp Leu
        35                  40                  45

Val Val Ile Trp Ser Asp Gly Ser Ser Thr Tyr Asn Ser Ala Leu Lys
    50                  55                  60

Ser Arg Met Thr Ile Ser Lys Asp Asn Ser Lys Ser Thr Val Tyr Leu
65                  70                  75                  80

Gln Met Asn Ser Leu Arg Ala Glu Asp Thr Ala Met Tyr Tyr Cys Ala
                85                  90                  95

Arg His Gly Thr Tyr Tyr Gly Met Thr Thr Thr Gly Asp Ala Leu Asp
            100                 105                 110

Tyr Trp Gly Gln Gly Thr Leu Val Thr Val Ser Ser
        115                 120

<210> SEQ ID NO 55
<211> LENGTH: 109
<212> TYPE: PRT
<213> ORGANISM: Mus musculus

<400> SEQUENCE: 55

Gln Ile Val Leu Thr Gln Ser Pro Ala Ile Met Ser Ala Ser Leu Gly
1               5                   10                  15

Glu Arg Val Thr Met Thr Cys Thr Ala Ser Ser Ser Val Ser Ser Asn
            20                  25                  30

Tyr Leu His Trp Tyr Gln Gln Lys Pro Gly Ser Ala Pro Asn Leu Trp

```
                35                  40                  45
Ile Tyr Ser Thr Ser Asn Leu Ala Ser Gly Val Pro Ala Arg Phe Ser
         50                  55                  60
Gly Ser Gly Ser Gly Thr Ser Tyr Ser Leu Thr Ile Ser Ser Met Glu
 65                  70                  75                  80
Ala Glu Asp Ala Ala Thr Tyr Tyr Cys His Gln Tyr Leu Arg Ser Pro
                 85                  90                  95
Pro Thr Phe Gly Gly Gly Thr Lys Leu Glu Ile Lys Arg
                100                 105

<210> SEQ ID NO 56
<211> LENGTH: 109
<212> TYPE: PRT
<213> ORGANISM: Artificial Sequence
<220> FEATURE:
<223> OTHER INFORMATION: synthetically generated peptide

<400> SEQUENCE: 56

Asp Ile Gln Leu Thr Gln Ser Pro Ser Ser Met Ser Ala Ser Leu Gly
 1               5                  10                  15
Asp Arg Val Thr Met Thr Cys Thr Ala Ser Ser Ser Val Ser Ser Asn
                20                  25                  30
Tyr Leu His Trp Tyr Gln Gln Lys Pro Gly Lys Ala Pro Asn Leu Trp
             35                  40                  45
Ile Tyr Ser Thr Ser Asn Leu Ala Ser Gly Val Pro Ser Arg Phe Ser
         50                  55                  60
Gly Ser Gly Ser Gly Thr Asp Tyr Thr Leu Thr Ile Ser Ser Met Gln
 65                  70                  75                  80
Pro Glu Asp Phe Ala Thr Tyr Tyr Cys His Gln Tyr Leu Arg Ser Pro
                 85                  90                  95
Pro Thr Phe Gly Gln Gly Thr Lys Leu Glu Ile Lys Arg
                100                 105

<210> SEQ ID NO 57
<211> LENGTH: 109
<212> TYPE: PRT
<213> ORGANISM: Artificial Sequence
<220> FEATURE:
<223> OTHER INFORMATION: synthetically generated peptide

<400> SEQUENCE: 57

Asp Ile Gln Leu Thr Gln Ser Pro Ser Ser Leu Ser Ala Ser Val Gly
 1               5                  10                  15
Asp Arg Val Thr Met Thr Cys Thr Ala Ser Ser Ser Val Ser Ser Asn
                20                  25                  30
Tyr Leu His Trp Tyr Gln Gln Lys Pro Gly Lys Ala Pro Lys Leu Trp
             35                  40                  45
Ile Tyr Ser Thr Ser Asn Leu Ala Ser Gly Val Pro Ser Arg Phe Ser
         50                  55                  60
Gly Ser Gly Ser Gly Thr Asp Tyr Thr Leu Thr Ile Ser Ser Met Gln
 65                  70                  75                  80
Pro Glu Asp Phe Ala Thr Tyr Tyr Cys His Gln Tyr Leu Arg Ser Pro
                 85                  90                  95
Pro Thr Phe Gly Gln Gly Thr Lys Leu Glu Ile Lys Arg
                100                 105

<210> SEQ ID NO 58
<211> LENGTH: 109
```

```
<212> TYPE: PRT
<213> ORGANISM: Artificial Sequence
<220> FEATURE:
<223> OTHER INFORMATION: synthetically generated peptide

<400> SEQUENCE: 58

Asp Ile Gln Met Thr Gln Ser Pro Ser Ser Leu Ser Ala Ser Val Gly
1               5                   10                  15

Asp Arg Val Thr Ile Thr Cys Thr Ala Ser Ser Ser Val Ser Ser Asn
            20                  25                  30

Tyr Leu His Trp Tyr Gln Gln Lys Pro Gly Lys Ala Pro Lys Leu Leu
        35                  40                  45

Ile Tyr Ser Thr Ser Asn Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys His Gln Tyr Leu Arg Ser Pro
                85                  90                  95

Pro Thr Phe Gly Gln Gly Thr Lys Val Glu Ile Lys Arg
            100                 105

<210> SEQ ID NO 59
<211> LENGTH: 109
<212> TYPE: PRT
<213> ORGANISM: Artificial Sequence
<220> FEATURE:
<223> OTHER INFORMATION: synthetically generated peptide

<400> SEQUENCE: 59

Asp Ile Gln Leu Thr Gln Ser Pro Ser Ser Leu Ser Ala Ser Val Gly
1               5                   10                  15

Asp Arg Val Thr Ile Thr Cys Thr Ala Ser Ser Ser Val Ser Ser Asn
            20                  25                  30

Tyr Leu His Trp Tyr Gln Gln Lys Pro Gly Lys Ala Pro Lys Leu Trp
        35                  40                  45

Ile Tyr Ser Thr Ser Asn Leu Ala Ser Gly Val Pro Ser Arg Phe Ser
    50                  55                  60

Gly Ser Gly Ser Gly Thr Asp Tyr Thr Leu Thr Ile Ser Ser Leu Gln
65                  70                  75                  80

Pro Glu Asp Phe Ala Thr Tyr Tyr Cys His Gln Tyr Leu Arg Ser Pro
                85                  90                  95

Pro Thr Phe Gly Gln Gly Thr Lys Val Glu Ile Lys Arg
            100                 105

<210> SEQ ID NO 60
<211> LENGTH: 109
<212> TYPE: PRT
<213> ORGANISM: Artificial Sequence
<220> FEATURE:
<223> OTHER INFORMATION: synthetically generated peptide

<400> SEQUENCE: 60

Asp Ile Gln Leu Thr Gln Ser Pro Ser Ser Leu Ser Ala Ser Val Gly
1               5                   10                  15

Asp Arg Val Thr Met Thr Cys Thr Ala Ser Ser Ser Val Ser Ser Asn
            20                  25                  30

Tyr Leu His Trp Tyr Gln Gln Lys Pro Gly Lys Ala Pro Lys Leu Trp
        35                  40                  45

Ile Tyr Ser Thr Ser Asn Leu Ala Ser Gly Val Pro Ser Arg Phe Ser
```

```
            50                  55                  60
Gly Ser Gly Ser Gly Thr Asp Tyr Thr Leu Thr Ile Ser Ser Leu Gln
 65                  70                  75                  80

Pro Glu Asp Phe Ala Thr Tyr Tyr Cys His Gln Tyr Leu Arg Ser Pro
                 85                  90                  95

Pro Thr Phe Gly Gln Gly Thr Lys Val Glu Ile Lys Arg
            100                 105
```

<210> SEQ ID NO 61
<211> LENGTH: 2171
<212> TYPE: DNA
<213> ORGANISM: Artificial Sequence
<220> FEATURE:
<223> OTHER INFORMATION: synthetically generated oligonucleotide

<400> SEQUENCE: 61

| | | |
|---|---|---|
| gaattcgcca ccatggagct gggcctgtcc tggatcttcc tgctggccat cctgaagggc | 60 |
| gtgcagtgcc aggttcagct gcagcagtct ggaggagagc tggctaagcc tggagcttct | 120 |
| gtgaaggtga gctgtaaggc ttccggctac acctttagct ccttctggat gcactgggtg | 180 |
| cggcaggctc ctggacaggg actggagtgg attggatata tcaatcccccg gtccggctac | 240 |
| accgagtata atgagatctt tcgggataag gccaccatga ccaccgacac atccacctct | 300 |
| accgcttaca tggagctgag cagcctgagg tccgaggata cagctgtgta ttactgtgct | 360 |
| tcctttctgg gccggggcgc tatggactat ggggacaggg aaccaccgt gaccgtgtcc | 420 |
| tccaccaaag gtccttccgt gtttccccctg gccccttgct ccaggtccac ctccgagtcc | 480 |
| accgctgctc tgggatgcct ggtgaaagat tacttccccg agcccgtgac cgtgtcttgg | 540 |
| aatagtggcg ctctgaccag cggcgttcac accttccctg ctgttctgca gagctccgga | 600 |
| ctgtatagcc tgtccagcgt ggtgaccgtg ccttcctcca attttggcac ccagacctac | 660 |
| acctgtaatg tggatcacaa gcccagcaac accaaggtgg acaagaccgt ggagcggaag | 720 |
| tgttgtgtgg agtgtccccc atgtcccgct cctcctgtgg ctggaccttc cgtgtttctg | 780 |
| ttccccccaa agcccaagga taccctgatg atcagcagga cccctgaggt gacctgtgtg | 840 |
| gttgtggacg tgtcccacga ggaccctgaa gttcagttca attggtacgt ggatggcgtg | 900 |
| gacgtgcaca cgctaagac caagcctcgg gaggagcagt tcaacagcac ctttagggtg | 960 |
| gtgtccgtgt tgaccgtggt gcatcaggat tggctgaacg gcaaggagta caagtgcaag | 1020 |
| gtgtccaaca agggcctgcc cgctcctatt gagaagacca tcagcaagac caagggccag | 1080 |
| cccagagagc ctcaggtgta tactgccccc cctctagggg aggagatgac aaagaaccag | 1140 |
| gtgagcctga cctgtctggt gaagggattc tatccctccg atatcgccgt ggagtgggag | 1200 |
| tccaatggcc agcctgaaaa caactataag accaccccctc ctatgctgga tagcgatggc | 1260 |
| tccttttcc tgtacagcaa gctgaccgtg gataagagcc ggtggcagca gggaaatgtg | 1320 |
| ttttcctgtt ccgtgatgca cgaggctctg cacaaccact acacccagaa gagcctgagc | 1380 |
| ctgagccctg gaaagggagg aggaggaggc ggaggaagcc aggtgcagct gaaggagtct | 1440 |
| ggaccaggac tggtggctcc atctcagtct ctgtccatca cctgcaccat ctccggcttt | 1500 |
| tccctgaccg actatggcgt gcactgggtt aggcagcctc ctggaaaggg actggagtgg | 1560 |
| ttggtggtca tttggagcga tggcagctcc acctataact ccgctctgaa gagccggatg | 1620 |
| accatcagga aggacaacag caagagccag gtgttcctga tcatgaatag cctgcagacc | 1680 |
| gatgacagcg ccatgtacta ctgtgctagg cacggcacct attatggcat gaccaccacc | 1740 |

```
ggcgacgctt tggactactg gggacaggga accagcgtga cagtgtctag cggaggagga   1800
ggatctggcg gaggaggaag cggaggagga ggatctcaga tcgtgctgac ccagagccct   1860
gctatcatgt ccgcttctct gggcgagaga gtgaccatga cctgcacagc ttccagctcc   1920
gtgagctcta attacctgca ctggtatcag cagaagcctg gcagcgctcc aaacttgtgg   1980
atctatagca ccagcaatct ggccagcggc gtgcctgcta ggttttccgg atctggatct   2040
ggcaccagct actccctgac catcagctct atggaggccg aggatgctgc cacatactat   2100
tgtcaccagt atctgaggag ccccctacc tttggcggag aaccaaact ggagatcaag    2160 tgagcggccg c                                                        2171
```

<210> SEQ ID NO 62
<211> LENGTH: 723
<212> TYPE: DNA
<213> ORGANISM: Artificial Sequence
<220> FEATURE:
<223> OTHER INFORMATION: synthetically generated oligonucleotide

<400> SEQUENCE: 62

```
gaattcgcca ccatgcgggt gcccgcccag ctgctgggcc tgctgctgct gtggctgccc    60
ggcacccggt gcgacatcca gatgacccag agcccttcct ccctgtctgc ttctgtggga   120
gatcgggtga ccatcacctg cagagcttcc caggatatct ccaattacct ggcttggtat   180
caacagaagc ccggcaaggc tcctaagctg ttgatctact ataccagcaa gatccacagc   240
ggcgtgccct ccaggttttc tggatctgga tctggcaccg attaccactt taccatctcc   300
agcctgcagc ccgaggacat tgctacatac tactgccagc agggcaacac ctttccctac   360
accttcggcc agggcacaaa ggttgagatc aaggtggctg ctccttccgt gtttatcttc   420 cccccctagcg atgagcagct gaagtccgga accgcttccg ttgtgtgtct gctgaacaac   480
ttctatcccc gggaggccaa ggtgcagtgg aaagtggata acgccctgca gtccggcaac   540
tctcaggaat ctgtgaccga gcaggactcc aaggactcca catacagcct gagctccacc   600
ctgaccctgt ctaaggctga ctacgagaag cacaaggtgt acgcttgcga ggtgacccac   660
cagggattgt ctagccctgt gaccaagtcc ttcaatcggg gcgagtgctg aataagcggc   720
cgc                                                                 723
```

<210> SEQ ID NO 63
<211> LENGTH: 701
<212> TYPE: PRT
<213> ORGANISM: Artificial Sequence
<220> FEATURE:
<223> OTHER INFORMATION: synthetically generated peptide

<400> SEQUENCE: 63

```
Gln Val Gln Leu Gln Gln Ser Gly Gly Glu Leu Ala Lys Pro Gly Ala
1               5                   10                  15

Ser Val Lys Val Ser Cys Lys Ala Ser Gly Tyr Thr Phe Ser Ser Phe
            20                  25                  30

Trp Met His Trp Val Arg Gln Ala Pro Gly Gln Gly Leu Glu Trp Ile
        35                  40                  45

Gly Tyr Ile Asn Pro Arg Ser Gly Tyr Thr Glu Tyr Asn Glu Ile Phe
    50                  55                  60

Arg Asp Lys Ala Thr Met Thr Thr Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

-continued

```
Ala Ser Phe Leu Gly Arg Gly Ala Met Asp Tyr Trp Gly Gln Gly Thr
                100                 105                 110

Thr Val Thr Val Ser Ser Ala Ser Thr Lys Gly Pro Ser Val Phe Pro
            115                 120                 125

Leu Ala Pro Cys Ser Arg Ser Thr Ser Glu Ser Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Cys Val Glu Cys
210                 215                 220

Pro Pro Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Phe Arg Val Val Ser Val Leu Thr
290                 295                 300

Val Val His Gln Asp Trp Leu Asn Gly Lys Glu Tyr Lys Cys Lys Val
305                 310                 315                 320

Ser Asn Lys Gly Leu Pro Ala Pro Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys Gly Gly Gly Gly
        435                 440                 445

Ser Gly Gly Gly Gly Ser Gln Val Gln Leu Lys Glu Ser Gly Pro Gly
450                 455                 460

Leu Val Ala Pro Ser Gln Ser Leu Ser Ile Thr Cys Thr Ile Ser Gly
465                 470                 475                 480

Phe Ser Leu Thr Asp Tyr Gly Val His Trp Val Arg Gln Pro Pro Gly
                485                 490                 495

Lys Gly Leu Glu Trp Leu Val Val Ile Trp Ser Asp Gly Ser Ser Thr
            500                 505                 510
```

```
Tyr Asn Ser Ala Leu Lys Ser Arg Met Thr Ile Arg Lys Asp Asn Ser
            515                 520                 525

Lys Ser Gln Val Phe Leu Ile Met Asn Ser Leu Gln Thr Asp Asp Ser
        530                 535                 540

Ala Met Tyr Tyr Cys Ala Arg His Gly Thr Tyr Tyr Gly Met Thr Thr
545                 550                 555                 560

Thr Gly Asp Ala Leu Asp Tyr Trp Gly Gln Gly Thr Ser Val Thr Val
                565                 570                 575

Ser Ser Gly Gly Gly Gly Ser Gly Gly Gly Ser Gly Gly Gly Gly
            580                 585                 590

Ser Gln Ile Val Leu Thr Gln Ser Pro Ala Ile Met Ser Ala Ser Leu
        595                 600                 605

Gly Glu Arg Val Thr Met Thr Cys Thr Ala Ser Ser Ser Val Ser Ser
610                 615                 620

Asn Tyr Leu His Trp Tyr Gln Gln Lys Pro Gly Ser Ala Pro Asn Leu
625                 630                 635                 640

Trp Ile Tyr Ser Thr Ser Asn Leu Ala Ser Gly Val Pro Ala Arg Phe
                645                 650                 655

Ser Gly Ser Gly Ser Gly Thr Ser Tyr Ser Leu Thr Ile Ser Ser Met
            660                 665                 670

Glu Ala Glu Asp Ala Ala Thr Tyr Tyr Cys His Gln Tyr Leu Arg Ser
        675                 680                 685

Pro Pro Thr Phe Gly Gly Gly Thr Lys Leu Glu Ile Lys
690                 695                 700
```

```
<210> SEQ ID NO 64
<211> LENGTH: 214
<212> TYPE: PRT
<213> ORGANISM: Artificial Sequence
<220> FEATURE:
<223> OTHER INFORMATION: synthetically generated peptide

<400> SEQUENCE: 64

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Ala Trp Tyr Gln Gln Lys Pro Gly Lys Ala Pro Lys Leu Leu Ile
        35                  40                  45

Tyr Tyr Thr Ser Lys Ile His Ser Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln Gln Gly Asn Thr Phe Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 65
<211> LENGTH: 12
<212> TYPE: PRT
<213> ORGANISM: Artificial Sequence
<220> FEATURE:
<223> OTHER INFORMATION: synthetically generated peptide
<220> FEATURE:
<221> NAME/KEY: VARIANT
<222> LOCATION: (3)..(3)
<223> OTHER INFORMATION: S or T
<220> FEATURE:
<221> NAME/KEY: VARIANT
<222> LOCATION: (4)..(4)
<223> OTHER INFORMATION: S or P or T
<220> FEATURE:
<221> NAME/KEY: VARIANT
<222> LOCATION: (5)..(5)
<223> OTHER INFORMATION: Q or N
<220> FEATURE:
<221> NAME/KEY: VARIANT
<222> LOCATION: (7)..(7)
<223> OTHER INFORMATION: F or S
<220> FEATURE:
<221> NAME/KEY: VARIANT
<222> LOCATION: (8)..(8)
<223> OTHER INFORMATION: T or I
<220> FEATURE:
<221> NAME/KEY: VARIANT
<222> LOCATION: (10)..(10)
<223> OTHER INFORMATION: K or T
<220> FEATURE:
<221> NAME/KEY: VARIANT
<222> LOCATION: (12)..(12)
<223> OTHER INFORMATION: G or D or S

<400> SEQUENCE: 65

Thr Leu Xaa Xaa Xaa His Xaa Xaa Tyr Xaa Ile Xaa
1               5                   10

<210> SEQ ID NO 66
<211> LENGTH: 11
<212> TYPE: PRT
<213> ORGANISM: Artificial Sequence
<220> FEATURE:
<223> OTHER INFORMATION: synthetically generated peptide
<220> FEATURE:
<221> NAME/KEY: VARIANT
<222> LOCATION: (1)..(1)
<223> OTHER INFORMATION: L or I
<220> FEATURE:
<221> NAME/KEY: VARIANT
<222> LOCATION: (2)..(2)
<223> OTHER INFORMATION: N or T
<220> FEATURE:
<221> NAME/KEY: VARIANT
<222> LOCATION: (4)..(4)
<223> OTHER INFORMATION: D or H or S
<220> FEATURE:
<221> NAME/KEY: VARIANT
<222> LOCATION: (5)..(5)
<223> OTHER INFORMATION: G or S
<220> FEATURE:
<221> NAME/KEY: VARIANT
<222> LOCATION: (6)..(6)
<223> OTHER INFORMATION: S or L or T
<220> FEATURE:
<221> NAME/KEY: VARIANT

```
<222> LOCATION: (7)..(7)
<223> OTHER INFORMATION: H or Y
<220> FEATURE:
<221> NAME/KEY: VARIANT
<222> LOCATION: (8)..(8)
<223> OTHER INFORMATION: N or K or Q or I
<220> FEATURE:
<221> NAME/KEY: VARIANT
<222> LOCATION: (9)..(9)
<223> OTHER INFORMATION: K or T
<220> FEATURE:
<221> NAME/KEY: VARIANT
<222> LOCATION: (10)..(10)
<223> OTHER INFORMATION: G or A
<220> FEATURE:
<221> NAME/KEY: VARIANT
<222> LOCATION: (11)..(11)
<223> OTHER INFORMATION: D or S or V

<400> SEQUENCE: 66

Xaa Xaa Ser Xaa Xaa Xaa Xaa Xaa Xaa Xaa Xaa
1               5                   10

<210> SEQ ID NO 67
<211> LENGTH: 9
<212> TYPE: PRT
<213> ORGANISM: Artificial Sequence
<220> FEATURE:
<223> OTHER INFORMATION: synthetically generated peptide
<220> FEATURE:
<221> NAME/KEY: VARIANT
<222> LOCATION: (1)..(1)
<223> OTHER INFORMATION: G or A
<220> FEATURE:
<221> NAME/KEY: VARIANT
<222> LOCATION: (2)..(2)
<223> OTHER INFORMATION: S or A or Y
<220> FEATURE:
<221> NAME/KEY: VARIANT
<222> LOCATION: (3)..(3)
<223> OTHER INFORMATION: S or Y
<220> FEATURE:
<221> NAME/KEY: VARIANT
<222> LOCATION: (5)..(5)
<223> OTHER INFORMATION: S or A or Y
<220> FEATURE:
<221> NAME/KEY: VARIANT
<222> LOCATION: (6)..(6)
<223> OTHER INFORMATION: S or Y or T
<220> FEATURE:
<221> NAME/KEY: VARIANT
<222> LOCATION: (9)..(9)
<223> OTHER INFORMATION: V or I

<400> SEQUENCE: 67

Xaa Xaa Xaa Tyr Xaa Xaa Gly Tyr Xaa
1               5

<210> SEQ ID NO 68
<211> LENGTH: 10
<212> TYPE: PRT
<213> ORGANISM: Artificial Sequence
<220> FEATURE:
<223> OTHER INFORMATION: synthetically generated peptide
<220> FEATURE:
<221> NAME/KEY: VARIANT
<222> LOCATION: (6)..(6)
<223> OTHER INFORMATION: N or A
<220> FEATURE:
<221> NAME/KEY: VARIANT
<222> LOCATION: (9)..(9)
<223> OTHER INFORMATION: I or V

<400> SEQUENCE: 68
```

Gly Phe Thr Phe Ser Xaa Arg Trp Xaa Tyr
1               5                   10

<210> SEQ ID NO 69
<211> LENGTH: 19
<212> TYPE: PRT
<213> ORGANISM: Artificial Sequence
<220> FEATURE:
<223> OTHER INFORMATION: synthetically generated peptide
<220> FEATURE:
<221> NAME/KEY: VARIANT
<222> LOCATION: (7)..(7)
<223> OTHER INFORMATION: N or A or T
<220> FEATURE:
<221> NAME/KEY: VARIANT
<222> LOCATION: (8)..(8)
<223> OTHER INFORMATION: I or R
<220> FEATURE:
<221> NAME/KEY: VARIANT
<222> LOCATION: (12)..(12)
<223> OTHER INFORMATION: E or Q

<400> SEQUENCE: 69

Gly Ile Lys Thr Lys Pro Xaa Xaa Tyr Ala Thr Xaa Tyr Ala Asp Ser
1               5                   10                  15

Val Lys Gly

<210> SEQ ID NO 70
<211> LENGTH: 9
<212> TYPE: PRT
<213> ORGANISM: Artificial Sequence
<220> FEATURE:
<223> OTHER INFORMATION: synthetically generated peptide
<220> FEATURE:
<221> NAME/KEY: VARIANT
<222> LOCATION: (1)..(1)
<223> OTHER INFORMATION: L or V
<220> FEATURE:
<221> NAME/KEY: VARIANT
<222> LOCATION: (4)..(4)
<223> OTHER INFORMATION: M or K
<220> FEATURE:
<221> NAME/KEY: VARIANT
<222> LOCATION: (5)..(5)
<223> OTHER INFORMATION: R or K

<400> SEQUENCE: 70

Xaa Thr Gly Xaa Xaa Tyr Phe Asp Tyr
1               5

<210> SEQ ID NO 71
<211> LENGTH: 11
<212> TYPE: PRT
<213> ORGANISM: Artificial Sequence
<220> FEATURE:
<223> OTHER INFORMATION: synthetically generated peptide

<400> SEQUENCE: 71

Thr Leu Ser Ser Gln His Ser Thr Tyr Thr Ile
1               5                   10

<210> SEQ ID NO 72
<211> LENGTH: 15
<212> TYPE: PRT
<213> ORGANISM: Artificial Sequence
<220> FEATURE:
<223> OTHER INFORMATION: synthetically generated peptide

<400> SEQUENCE: 72

Leu Asn Ser Asp Ser Ser His Asn Lys Gly Ser Gly Ile Pro Asp

```
1               5                   10                  15
```

<210> SEQ ID NO 73
<211> LENGTH: 9
<212> TYPE: PRT
<213> ORGANISM: Artificial Sequence
<220> FEATURE:
<223> OTHER INFORMATION: synthetically generated peptide

<400> SEQUENCE: 73

```
Ala Ala Tyr Tyr Ala Tyr Gly Tyr Val
1               5
```

<210> SEQ ID NO 74
<211> LENGTH: 10
<212> TYPE: PRT
<213> ORGANISM: Artificial Sequence
<220> FEATURE:
<223> OTHER INFORMATION: synthetically generated peptide

<400> SEQUENCE: 74

```
Gly Phe Thr Phe Ser Ala Arg Trp Ile Tyr
1               5                   10
```

<210> SEQ ID NO 75
<211> LENGTH: 22
<212> TYPE: PRT
<213> ORGANISM: Artificial Sequence
<220> FEATURE:
<223> OTHER INFORMATION: synthetically generated peptide

<400> SEQUENCE: 75

```
Gly Ile Lys Thr Lys Pro Ala Ile Tyr Ala Thr Glu Tyr Ala Asp Ser
1               5                   10                  15

Val Lys Gly Arg Phe Thr
            20
```

<210> SEQ ID NO 76
<211> LENGTH: 9
<212> TYPE: PRT
<213> ORGANISM: Artificial Sequence
<220> FEATURE:
<223> OTHER INFORMATION: synthetically generated peptide

<400> SEQUENCE: 76

```
Leu Thr Gly Met Lys Tyr Phe Asp Tyr
1               5
```

<210> SEQ ID NO 77
<211> LENGTH: 108
<212> TYPE: PRT
<213> ORGANISM: Artificial Sequence
<220> FEATURE:
<223> OTHER INFORMATION: synthetically generated peptide

<400> SEQUENCE: 77

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Asn
            20                  25                  30

Leu Asn Trp Tyr Gln Gln Lys Pro Gly Lys Ala Pro Lys Leu Leu Ile
        35                  40                  45

Tyr Ala Ala Ser Asn Leu Gln Ser Gly Pro Ser Arg Phe Ser Gly Ser
    50                  55                  60
```

-continued

Gly Ser Gly Thr Asp Phe Thr Leu Thr Ile Ser Ser Leu Gln Pro Glu
65                  70                  75                  80

Asp Phe Ala Val Tyr Tyr Cys Gln Gln Tyr Ser Asp Gln Ser Tyr Thr
                85                  90                  95

Phe Gly Gln Gly Thr Lys Val Glu Ile Lys Arg Thr
            100                 105

<210> SEQ ID NO 78
<211> LENGTH: 126
<212> TYPE: PRT
<213> ORGANISM: Artificial Sequence
<220> FEATURE:
<223> OTHER INFORMATION: synthetically generated peptide

<400> SEQUENCE: 78

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ser Ser Ile Ser Tyr Ser Asp Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Gly Asp Tyr Gly His His Gly Leu Ser Gly Ile
            100                 105                 110

Phe Asp Tyr Trp Gly Gln Gly Thr Leu Val Thr Val Ser Ser
        115                 120                 125

<210> SEQ ID NO 79
<211> LENGTH: 109
<212> TYPE: PRT
<213> ORGANISM: Artificial Sequence
<220> FEATURE:
<223> OTHER INFORMATION: synthetically generated peptide

<400> SEQUENCE: 79

Asp Ile Glu Leu Thr Gln Pro Pro Ser Val Ser Val Ala Pro Gly Gln
1               5                   10                  15

Thr Ala Arg Ile Ser Cys Ser Gly Asp Ser Ile Gly Glu Gln Tyr Ala
            20                  25                  30

His Trp Tyr Gln Gln Lys Pro Gly Gln Ala Pro Val Leu Val Ile Tyr
        35                  40                  45

Asp Asp Asn Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gly Ser Tyr Thr Leu Thr Asn Thr Ala
                85                  90                  95

Ser Val Phe Gly Gly Gly Thr Lys Leu Thr Val Leu Gly
            100                 105

<210> SEQ ID NO 80
<211> LENGTH: 124
<212> TYPE: PRT
<213> ORGANISM: Artificial Sequence

```
<220> FEATURE:
<223> OTHER INFORMATION: synthetically generated peptide

<400> SEQUENCE: 80

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Asn Trp Val Arg Gln Ala Pro Gly Lys Gly Leu Glu Trp Val
        35                  40                  45

Ser Arg Ile Ser Tyr Ser Gly Ser Asp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Glu Phe Gly Phe Met Tyr Ser Thr Leu Val Phe Asp
            100                 105                 110

Ser Trp Gly Gln Gly Thr Leu Val Thr Val Ser Ser
        115                 120

<210> SEQ ID NO 81
<211> LENGTH: 109
<212> TYPE: PRT
<213> ORGANISM: Artificial Sequence
<220> FEATURE:
<223> OTHER INFORMATION: synthetically generated peptide

<400> SEQUENCE: 81

Asp Ile Glu Leu Thr Gln Pro Pro Ser Val Ser Val Ala Pro Gly Gln
1               5                   10                  15

Thr Ala Arg Ile Ser Cys Ser Gly Asp Ser Ile Gly Glu Gln Tyr Ala
            20                  25                  30

His Trp Tyr Gln Gln Lys Pro Gly Gln Ala Pro Val Leu Val Ile Tyr
        35                  40                  45

Asp Asp Asn Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Ser Ser Tyr Thr Ser Ser Asp Ala
                85                  90                  95

Ser Val Phe Gly Gly Thr Lys Leu Thr Val Leu Gly
            100                 105

<210> SEQ ID NO 82
<211> LENGTH: 123
<212> TYPE: PRT
<213> ORGANISM: Artificial Sequence
<220> FEATURE:
<223> OTHER INFORMATION: synthetically generated peptide

<400> SEQUENCE: 82

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Asn Trp Val Arg Gln Ala Pro Gly Lys Gly Leu Glu Trp Val
        35                  40                  45
```

```
Ser Ala Ile His Asp Asn Gly His Thr Tyr Tyr Pro Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Glu Gly Glu Phe Gly Phe Met Tyr Ser Thr Leu Val Phe Asp Ser
            100                 105                 110

Trp Gly Gln Gly Thr Leu Val Thr Val Ser Ser
            115                 120

<210> SEQ ID NO 83
<211> LENGTH: 108
<212> TYPE: PRT
<213> ORGANISM: Artificial Sequence
<220> FEATURE:
<223> OTHER INFORMATION: synthetically generated peptide

<400> SEQUENCE: 83

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Ser Ser Asn
                 20                  25                  30

Leu Asn Trp Tyr Gln Gln Lys Pro Gly Lys Ala Pro Lys Leu Leu Ile
             35                  40                  45

Tyr Ala Ala Ser Asn Leu Gln Ser Gly Pro Ser Arg Phe Ser Gly Ser
 50                  55                  60

Gly Ser Gly Thr Asp Phe Thr Leu Thr Ile Ser Ser Leu Gln Pro Glu
 65                  70                  75                  80

Asp Phe Ala Thr Tyr Tyr Cys Gln Gln Tyr Ala Ser Pro Arg Gln Thr
                 85                  90                  95

Phe Gly Gln Gly Thr Lys Val Glu Ile Lys Arg Thr
            100                 105

<210> SEQ ID NO 84
<211> LENGTH: 128
<212> TYPE: PRT
<213> ORGANISM: Artificial Sequence
<220> FEATURE:
<223> OTHER INFORMATION: synthetically generated peptide

<400> SEQUENCE: 84

Gln Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
                 20                  25                  30

Gly Met Ser Trp Val Arg Gln Ala Pro Gly Lys Gly Leu Glu Trp Val
             35                  40                  45

Ser Gly Ile Arg Ala Lys Gln Ser Gly Tyr Ala Thr Asp Tyr Ala Ala
 50                  55                  60

Pro Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Ala Arg Gly Leu Gly Asp Tyr Gly His His Gly Leu Ser
            100                 105                 110

Gly Ile Phe Asp Tyr Trp Gly Gln Gly Thr Leu Val Thr Val Ser Ser
            115                 120                 125
```

<210> SEQ ID NO 85
<211> LENGTH: 108
<212> TYPE: PRT
<213> ORGANISM: Artificial Sequence
<220> FEATURE:
<223> OTHER INFORMATION: synthetically generated peptide

<400> SEQUENCE: 85

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Asn
            20                  25                  30

Leu Asn Trp Tyr Gln Gln Lys Pro Gly Lys Ala Pro Lys Leu Leu Ile
        35                  40                  45

Tyr Ala Ala Ser Asn Leu Gln Ser Gly Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Tyr Glu Phe Gly Ile Gln Thr
                85                  90                  95

Phe Gly Gln Gly Thr Lys Val Glu Ile Lys Arg Thr
            100                 105

<210> SEQ ID NO 86
<211> LENGTH: 128
<212> TYPE: PRT
<213> ORGANISM: Artificial Sequence
<220> FEATURE:
<223> OTHER INFORMATION: synthetically generated peptide

<400> SEQUENCE: 86

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ser Gly Ile Arg Ala Lys Gln Ser Gly Tyr Ala Thr Asp Tyr Ala Ala
    50                  55                  60

Pro Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Gly Leu Gly Asp Tyr Gly His His His Gly Leu Ser
            100                 105                 110

Gly Ile Phe Asp Tyr Trp Gly Gln Gly Thr Leu Val Thr Val Ser Ser
        115                 120                 125

<210> SEQ ID NO 87
<211> LENGTH: 108
<212> TYPE: PRT
<213> ORGANISM: Artificial Sequence
<220> FEATURE:
<223> OTHER INFORMATION: synthetically generated peptide

<400> SEQUENCE: 87

Asp Ile Gln Met Thr Gln Ser Pro Ser Ser Leu Ser Ala Ser Val Gly
1               5                   10                  15

```
Asp Arg Val Thr Ile Thr Cys Arg Ala Ser Gln Gly Ile Ser Ser Asn
            20                  25                  30

Leu Asn Trp Tyr Gln Gln Lys Pro Gly Lys Ala Pro Lys Leu Leu Ile
        35                  40                  45

Tyr Ala Ala Ser Asn Leu Gln Ser Gly Pro Ser Arg Phe Ser Gly Ser
 50                  55                  60

Gly Ser Gly Thr Asp Phe Thr Leu Thr Ile Ser Ser Leu Gln Pro Glu
 65                  70                  75                  80

Asp Phe Ala Thr Tyr Tyr Cys Gln Gln Tyr Ser Ser Asn Pro Gln Thr
                85                  90                  95

Phe Gly Gln Gly Thr Lys Val Glu Ile Lys Arg Thr
            100                 105
```

<210> SEQ ID NO 88
<211> LENGTH: 128
<212> TYPE: PRT
<213> ORGANISM: Artificial Sequence
<220> FEATURE:
<223> OTHER INFORMATION: synthetically generated peptide

<400> SEQUENCE: 88

```
Gln Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ser Phe Ile Glu Pro Lys Trp Arg Gly Gly Ala Thr His Tyr Ala Ala
 50                  55                  60

Ser Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                85                  90                  95

Tyr Cys Ala Arg Gly Leu Gly Asp Tyr Gly His His His Gly Leu Ser
            100                 105                 110

Gly Ile Phe Asp Tyr Trp Gly Gln Gly Thr Leu Val Thr Val Ser Ser
        115                 120                 125
```

<210> SEQ ID NO 89
<211> LENGTH: 108
<212> TYPE: PRT
<213> ORGANISM: Artificial Sequence
<220> FEATURE:
<223> OTHER INFORMATION: synthetically generated peptide

<400> SEQUENCE: 89

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Asn
            20                  25                  30

Leu Asn Trp Tyr Gln Gln Lys Pro Gly Lys Ala Pro Lys Leu Leu Ile
        35                  40                  45

Tyr Ala Ala Ser Asn Leu Gln Ser Gly Pro Ser Arg Phe Ser Gly Ser
 50                  55                  60

Gly Ser Gly Thr Asp Phe Thr Leu Thr Ile Ser Ser Leu Gln Pro Glu
 65                  70                  75                  80

Asp Phe Ala Val Tyr Tyr Cys Gln Gln Tyr Ser Asp Gln Ser Tyr Thr
                85                  90                  95
```

Phe Gly Gln Gly Thr Lys Val Glu Ile Lys Arg Thr
            100                 105

<210> SEQ ID NO 90
<211> LENGTH: 128
<212> TYPE: PRT
<213> ORGANISM: Artificial Sequence
<220> FEATURE:
<223> OTHER INFORMATION: synthetically generated peptide

<400> SEQUENCE: 90

Gln Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ser Gly Ile Arg Ala Lys Gln Ser Gly Tyr Ala Thr Asp Tyr Ala Ala
    50                  55                  60

Pro Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Gly Leu Gly Asp Tyr Gly His His Gly Leu Ser
            100                 105                 110

Gly Ile Phe Asp Tyr Trp Gly Gln Gly Thr Leu Val Thr Val Ser Ser
        115                 120                 125

<210> SEQ ID NO 91
<211> LENGTH: 17
<212> TYPE: PRT
<213> ORGANISM: Artificial Sequence
<220> FEATURE:
<223> OTHER INFORMATION: synthetically generated peptide

<400> SEQUENCE: 91

Tyr Ile Asn Pro Arg Ser Gly Tyr Thr Glu Cys Asn Glu Ile Phe Arg
1               5                   10                  15

Asp

<210> SEQ ID NO 92
<211> LENGTH: 23
<212> TYPE: PRT
<213> ORGANISM: Artificial Sequence
<220> FEATURE:
<223> OTHER INFORMATION: synthetically generated peptide

<400> SEQUENCE: 92

Asp Ile Gln Leu Thr Gln Ser Pro Ser Ser Met Ser Ala Ser Leu Gly
1               5                   10                  15

Asp Arg Val Thr Met Thr Cys
            20

<210> SEQ ID NO 93
<211> LENGTH: 23
<212> TYPE: PRT
<213> ORGANISM: Artificial Sequence
<220> FEATURE:
<223> OTHER INFORMATION: synthetically generated peptide

<400> SEQUENCE: 93

```
Asp Ile Gln Leu Thr Gln Ser Pro Ser Ser Leu Ser Ala Ser Val Gly
1               5                   10                  15

Asp Arg Val Thr Met Thr Cys
            20
```

<210> SEQ ID NO 94
<211> LENGTH: 23
<212> TYPE: PRT
<213> ORGANISM: Artificial Sequence
<220> FEATURE:
<223> OTHER INFORMATION: synthetically generated peptide

<400> SEQUENCE: 94

```
Asp Ile Gln Met Thr Gln Ser Pro Ser Ser Leu Ser Ala Ser Val Gly
1               5                   10                  15

Asp Arg Val Thr Ile Thr Cys
            20
```

<210> SEQ ID NO 95
<211> LENGTH: 23
<212> TYPE: PRT
<213> ORGANISM: Artificial Sequence
<220> FEATURE:
<223> OTHER INFORMATION: synthetically generated peptide

<400> SEQUENCE: 95

```
Asp Ile Gln Leu Thr Gln Ser Pro Ser Ser Leu Ser Ala Ser Val Gly
1               5                   10                  15

Asp Arg Val Thr Ile Thr Cys
            20
```

<210> SEQ ID NO 96
<211> LENGTH: 23
<212> TYPE: PRT
<213> ORGANISM: Artificial Sequence
<220> FEATURE:
<223> OTHER INFORMATION: synthetically generated peptide

<400> SEQUENCE: 96

```
Asp Ile Gln Leu Thr Gln Ser Pro Ser Ser Leu Ser Ala Ser Val Gly
1               5                   10                  15

Asp Arg Val Thr Met Thr Cys
            20
```

<210> SEQ ID NO 97
<211> LENGTH: 15
<212> TYPE: PRT
<213> ORGANISM: Artificial Sequence
<220> FEATURE:
<223> OTHER INFORMATION: synthetically generated peptide

<400> SEQUENCE: 97

```
Trp Tyr Gln Gln Lys Pro Gly Lys Ala Pro Asn Leu Trp Ile Tyr
1               5                   10                  15
```

<210> SEQ ID NO 98
<211> LENGTH: 15
<212> TYPE: PRT
<213> ORGANISM: Artificial Sequence
<220> FEATURE:
<223> OTHER INFORMATION: synthetically generated peptide

<400> SEQUENCE: 98

```
Trp Tyr Gln Gln Lys Pro Gly Lys Ala Pro Lys Leu Trp Ile Tyr
1               5                   10                  15
```

<210> SEQ ID NO 99
<211> LENGTH: 15
<212> TYPE: PRT
<213> ORGANISM: Artificial Sequence
<220> FEATURE:
<223> OTHER INFORMATION: synthetically generated peptide

<400> SEQUENCE: 99

Trp Tyr Gln Gln Lys Pro Gly Lys Ala Pro Lys Leu Leu Ile Tyr
1               5                   10                  15

<210> SEQ ID NO 100
<211> LENGTH: 32
<212> TYPE: PRT
<213> ORGANISM: Artificial Sequence
<220> FEATURE:
<223> OTHER INFORMATION: synthetically generated peptide

<400> SEQUENCE: 100

Gly Val Pro Ser Arg Phe Ser Gly Ser Gly Ser Gly Thr Asp Tyr Thr
1               5                   10                  15

Leu Thr Ile Ser Ser Met Gln Pro Glu Asp Phe Ala Thr Tyr Tyr Cys
            20                  25                  30

<210> SEQ ID NO 101
<211> LENGTH: 32
<212> TYPE: PRT
<213> ORGANISM: Artificial Sequence
<220> FEATURE:
<223> OTHER INFORMATION: synthetically generated peptide

<400> SEQUENCE: 101

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 102
<211> LENGTH: 10
<212> TYPE: PRT
<213> ORGANISM: Artificial Sequence
<220> FEATURE:
<223> OTHER INFORMATION: synthetically generated peptide

<400> SEQUENCE: 102

Phe Gly Gln Gly Thr Lys Leu Glu Ile Lys
1               5                   10

<210> SEQ ID NO 103
<211> LENGTH: 10
<212> TYPE: PRT
<213> ORGANISM: Artificial Sequence
<220> FEATURE:
<223> OTHER INFORMATION: synthetically generated peptide

<400> SEQUENCE: 103

Phe Gly Gln Gly Thr Lys Val Glu Ile Lys
1               5                   10

<210> SEQ ID NO 104
<211> LENGTH: 25
<212> TYPE: PRT
<213> ORGANISM: Artificial Sequence
<220> FEATURE:
<223> OTHER INFORMATION: synthetically generated peptide

<400> SEQUENCE: 104

Gln Val Gln Leu Val Glu Ser Gly Pro Gly Leu Val Gln Pro Gly Gly
1               5                   10                  15

Ser Leu Arg Ile Ser Lys Ala Ile Ser
            20                  25

<210> SEQ ID NO 105
<211> LENGTH: 25
<212> TYPE: PRT
<213> ORGANISM: Artificial Sequence
<220> FEATURE:
<223> OTHER INFORMATION: synthetically generated peptide

<400> SEQUENCE: 105

Glu Val Gln Leu Val Glu Ser Gly Gly Gly Leu Val Gln Pro Gly Gly
1               5                   10                  15

Ser Leu Arg Ile Ser Cys Ala Ile Ser
            20                  25

<210> SEQ ID NO 106
<211> LENGTH: 25
<212> TYPE: PRT
<213> ORGANISM: Artificial Sequence
<220> FEATURE:
<223> OTHER INFORMATION: synthetically generated peptide

<400> SEQUENCE: 106

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 107
<211> LENGTH: 25
<212> TYPE: PRT
<213> ORGANISM: Artificial Sequence
<220> FEATURE:
<223> OTHER INFORMATION: synthetically generated peptide

<400> SEQUENCE: 107

Glu Val Gln Leu Val Glu Ser Gly Gly Gly Leu Val Gln Pro Gly Gly
1               5                   10                  15

Ser Leu Arg Leu Ser Cys Ala Ile Ser
            20                  25

<210> SEQ ID NO 108
<211> LENGTH: 25
<212> TYPE: PRT
<213> ORGANISM: Artificial Sequence
<220> FEATURE:
<223> OTHER INFORMATION: synthetically generated peptide

<400> SEQUENCE: 108

Gln Val Gln Leu Val Glu Ser Gly Gly Gly Leu Val Gln Pro Gly Gly
1               5                   10                  15

Ser Leu Arg Ile Ser Cys Ala Ile Ser
            20                  25

<210> SEQ ID NO 109
<211> LENGTH: 14
<212> TYPE: PRT
<213> ORGANISM: Artificial Sequence
<220> FEATURE:

<223> OTHER INFORMATION: synthetically generated peptide

<400> SEQUENCE: 109

Trp Val Arg Gln Ala Pro Gly Lys Gly Leu Glu Trp Leu Val
1               5                   10

<210> SEQ ID NO 110
<211> LENGTH: 14
<212> TYPE: PRT
<213> ORGANISM: Artificial Sequence
<220> FEATURE:
<223> OTHER INFORMATION: synthetically generated peptide

<400> SEQUENCE: 110

Trp Val Arg Gln Ala Pro Gly Lys Gly Leu Glu Trp Val Ser
1               5                   10

<210> SEQ ID NO 111
<211> LENGTH: 32
<212> TYPE: PRT
<213> ORGANISM: Artificial Sequence
<220> FEATURE:
<223> OTHER INFORMATION: synthetically generated peptide

<400> SEQUENCE: 111

Arg Met Thr Ile Ser Lys Asp Asn Ser Lys Ser Thr Val Tyr Leu Gln
1               5                   10                  15

Met Asn Ser Leu Arg Ala Glu Asp Thr Ala Met Tyr Tyr Cys Ala Arg
            20                  25                  30

<210> SEQ ID NO 112
<211> LENGTH: 32
<212> TYPE: PRT
<213> ORGANISM: Artificial Sequence
<220> FEATURE:
<223> OTHER INFORMATION: synthetically generated peptide

<400> SEQUENCE: 112

Arg Met Thr Ile Ser Lys Asp Asn Ser Lys Asn Thr Val Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 113
<211> LENGTH: 32
<212> TYPE: PRT
<213> ORGANISM: Artificial Sequence
<220> FEATURE:
<223> OTHER INFORMATION: synthetically generated peptide

<400> SEQUENCE: 113

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 114
<211> LENGTH: 32
<212> TYPE: PRT
<213> ORGANISM: Artificial Sequence
<220> FEATURE:
<223> OTHER INFORMATION: synthetically generated peptide

<400> SEQUENCE: 114

Arg Met Thr Ile Ser Lys Asp Asn Ser Lys Ser Thr Val Tyr Leu Gln

```
1               5                  10                 15
Met Asn Ser Leu Arg Ala Glu Asp Thr Ala Val Tyr Tyr Cys Ala Arg
                20                    25                  30
```

<210> SEQ ID NO 115
<211> LENGTH: 11
<212> TYPE: PRT
<213> ORGANISM: Artificial Sequence
<220> FEATURE:
<223> OTHER INFORMATION: synthetically generated peptide

<400> SEQUENCE: 115

```
Trp Gly Gln Gly Thr Leu Val Thr Val Ser Ser
1               5                  10
```

<210> SEQ ID NO 116
<211> LENGTH: 12
<212> TYPE: PRT
<213> ORGANISM: Artificial Sequence
<220> FEATURE:
<223> OTHER INFORMATION: synthetically generated peptide

<400> SEQUENCE: 116

```
Glu Arg Lys Cys Cys Val Glu Cys Pro Pro Cys Pro
1               5                  10
```

<210> SEQ ID NO 117
<211> LENGTH: 15
<212> TYPE: PRT
<213> ORGANISM: Artificial Sequence
<220> FEATURE:
<223> OTHER INFORMATION: synthetically generated peptide

<400> SEQUENCE: 117

```
Glu Pro Lys Ser Ser Asp Lys Thr His Thr Cys Pro Pro Cys Pro
1               5                  10                 15
```

<210> SEQ ID NO 118
<211> LENGTH: 30
<212> TYPE: PRT
<213> ORGANISM: Artificial Sequence
<220> FEATURE:
<223> OTHER INFORMATION: synthetically generated peptide

<400> SEQUENCE: 118

```
Gln Val Gln Leu Gln Gln Ser Gly Gly Glu Leu Ala Lys Pro Gly Ala
1               5                  10                 15
Ser Val Lys Val Ser Cys Lys Ala Ser Gly Tyr Thr Phe Ser
                20                    25                  30
```